US006716629B2

(12) United States Patent
Hess et al.

(10) Patent No.: US 6,716,629 B2
(45) Date of Patent: Apr. 6, 2004

(54) APPARATUS FOR ASSAY, SYNTHESIS AND STORAGE, AND METHODS OF MANUFACTURE, USE, AND MANIPULATION THEREOF

(75) Inventors: Robert A. Hess, Arlington, MA (US); John Linton, Lincoln, MA (US); Tanya S. Kanigan, Cambridge, MA (US); Colin Brenan, Marblehead, MA (US); Can Ozbal, Cambridge, MA (US)

(73) Assignee: BioTrove, Inc., Cambridge, MA (US)

( * ) Notice: Subject to any disclaimer, the term of this patent is extended or adjusted under 35 U.S.C. 154(b) by 0 days.

(21) Appl. No.: 09/975,496

(22) Filed: Oct. 10, 2001

(65) Prior Publication Data

US 2002/0094533 A1 Jul. 18, 2002

Related U.S. Application Data

(60) Provisional application No. 60/239,538, filed on Oct. 10, 2000, provisional application No. 60/268,894, filed on Feb. 14, 2001, and provisional application No. 60/284,710, filed on Apr. 18, 2001.

(51) Int. Cl.[7] .............................. C12N 5/02; C12M 1/36
(52) U.S. Cl. .................... 435/420; 435/410; 435/283.1; 435/286.1; 435/288.2
(58) Field of Search ................... 435/410, 420, 435/286.1, 288.2, 283.1

(56) References Cited

U.S. PATENT DOCUMENTS

| | | | |
|---|---|---|---|
| 3,997,396 A | * | 12/1976 | Delente ...................... 435/400 |
| 5,152,060 A | | 10/1992 | Schubert et al. |
| 5,175,209 A | | 12/1992 | Beattie et al. |
| 5,722,370 A | | 3/1998 | Koike et al. |
| 5,843,767 A | | 12/1998 | Beattie |
| 6,015,880 A | | 1/2000 | Baldeschwieler et al. |
| 6,027,873 A | | 2/2000 | Schellenberger et al. |
| 6,083,763 A | | 7/2000 | Balch |
| 6,103,479 A | * | 8/2000 | Taylor ......................... 435/7.2 |
| 6,136,592 A | | 10/2000 | Leighton |
| 6,306,578 B1 | | 10/2001 | Schellenberger et al. |
| 6,309,600 B1 | | 10/2001 | Hunter |
| 2002/0049196 A1 | | 4/2002 | Carpino et al. |

FOREIGN PATENT DOCUMENTS

| | | | |
|---|---|---|---|
| JP | 63107057 A | 5/1988 | |
| WO | WO 99/55461 | 11/1999 | |
| WO | WO 00/51735 | 9/2000 | ............. B01L/3/00 |
| WO | WO 00/56456 | 9/2000 | |
| WO | WO 01/38583 | 5/2001 | ............. C12Q/1/68 |
| WO | WO 01/61054 A3 | 8/2001 | ............. B01L/3/00 |
| WO | WO 01/61054 A2 | 8/2001 | ............. C12Q/1/68 |
| WO | WO 01/87335 | 11/2001 | ......... A61K/39/395 |

* cited by examiner

*Primary Examiner*—Padmashri Ponnaluri
*Assistant Examiner*—My-Chau T. Tran
(74) *Attorney, Agent, or Firm*—Fish & Richardson, P.C.

(57) ABSTRACT

The invention features methods of making devices, or "platens", having a high-density array of through-holes, as well as methods of cleaning and refurbishing the surfaces of the platens. The invention further features methods of making high-density arrays of chemical, biochemical, and biological compounds, having many advantages over conventional, lower-density arrays. The invention includes methods by which many physical, chemical or biological transformations can be implemented in serial or in parallel within each addressable through-hole of the devices. Additionally, the invention includes methods of analyzing the contents of the array, including assaying of physical properties of the samples.

10 Claims, 16 Drawing Sheets

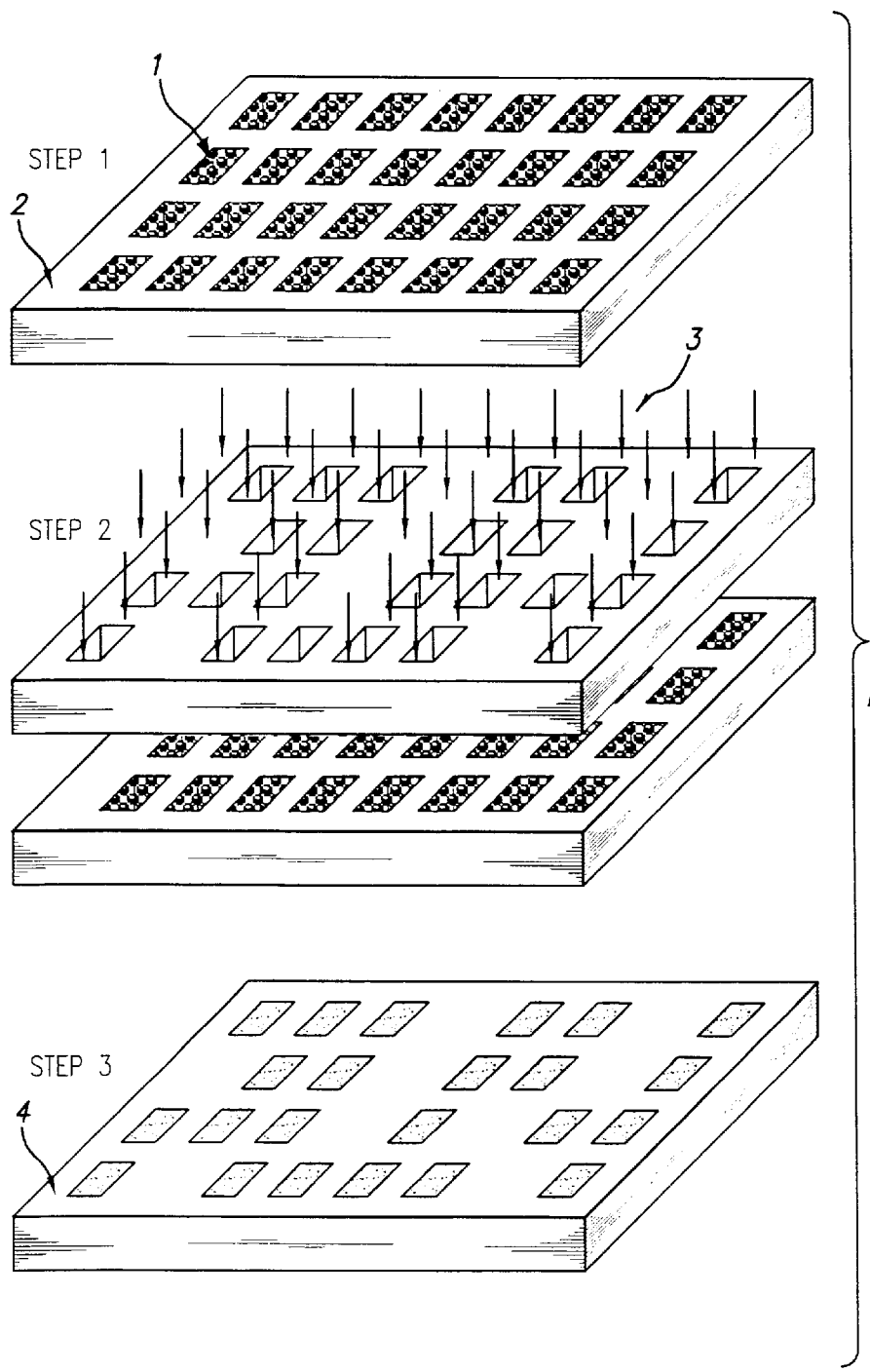

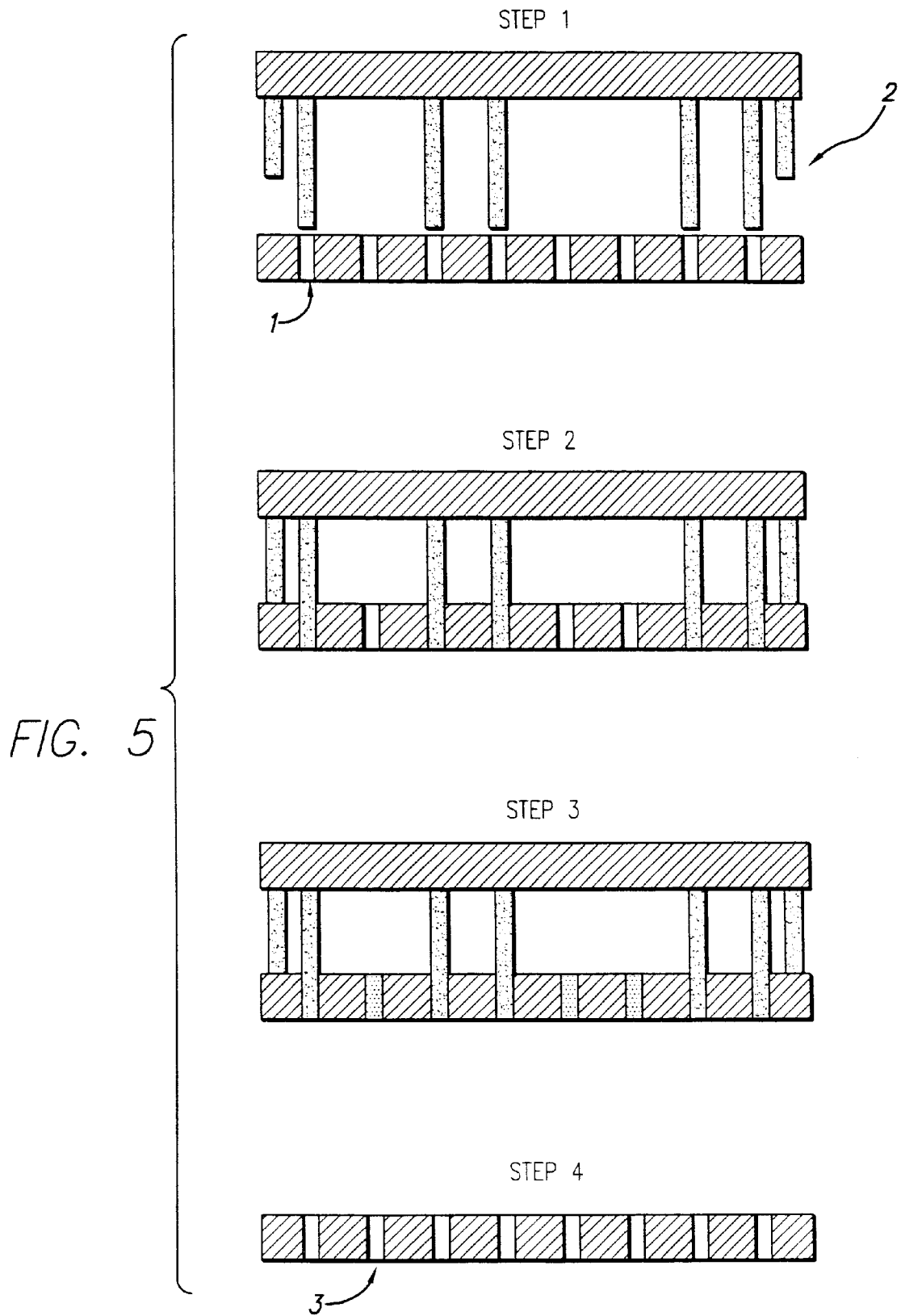

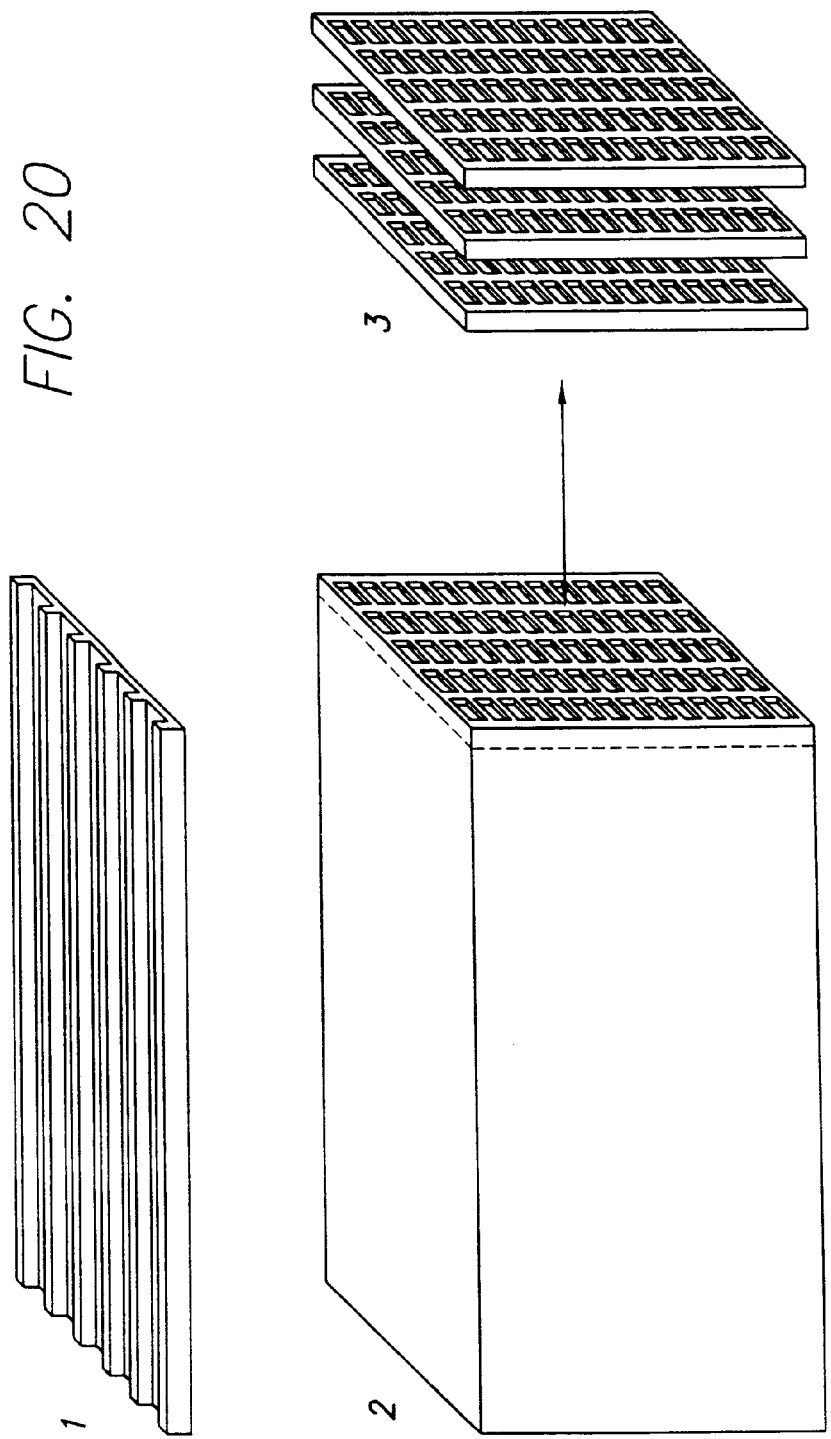

APPARATUS FOR ASSAY, SYNTHESIS AND STORAGE, AND METHODS OF MANUFACTURE, USE, AND MANIPULATION THEREOF

CROSS-REFERENCE TO RELATED APPLICATIONS

This application claims the benefit of U.S. Provisional Application No. 60/239,538, filed Oct. 10, 2000, U.S. Provisional Application No. 60/268,894, filed Feb. 14, 2001, and U.S. Provisional Application No. 60/284,710, filed Apr. 18, 2001, all of which are hereby incorporated by reference in their entirety.

FIELD OF THE INVENTION

This invention relates to devices for molecular synthesis, storage and screening, and other chemical, biochemical, biological, and physical experiments, and to methods of making, using, and manipulating the same.

BACKGROUND OF THE INVENTION

High throughput methods for creating and analyzing chemical and biochemical diversity play a vital role in technologies including drug discovery and development. Specific applications of high throughput methods include drug discovery, optimization of reaction conditions (e.g., conditions suitable for protein crystallization), genomics, proteomics, genotyping, polymorphism analysis, examination of RNA expression profiles in cells or tissues, sequencing by hybridization, and recombinant enzyme discovery.

Rapid, high throughput methods for synthesizing (e.g., using combinatorial chemistry methods) and screening large numbers of these compounds for biological and physicochemical properties are desired, for example, to increase the speed of discovery and optimization of drug leads.

Similarly, due in part to the large amount of sequence data from the human genome project, efforts are underway to rapidly obtain x-ray crystallography data for the protein products of many newly discovered genes. One of the rate limiting steps in this process is the search for appropriate solution conditions (e.g., pH, salt concentration) to cause protein crystallization. There is also a need to determine the function of each of the newly discovered genes (i.e., "functional genomics") and to map protein-protein interactions (i.e., "proteomics"). Given the large number of human genes, protein modifications, and protein binding partners, higher throughput methods are desired.

Another advance in biotechnology is the creation of surfaces with high-density arrays of biopolymers such as oligonucleotides or peptides. High-density oligonucleotide arrays are used, for example, in genotyping, polymorphism analysis, examination of RNA expression profiles in cells or tissues, and hybridization-based sequencing methods as described, for example, in U.S. Pat. Nos. 5,492,806, 5,525, 464, and 5,667,972 to Hyseq, Inc. Arrays containing a greater number of probes than currently provided are desirable.

The process of discovering and improving recombinant enzymes for industrial or consumer use has emerged as an important economic activity in recent years. A desire to discover very rare, activity-improving mutations has further stimulated the search for higher throughput screening methods. Such methods often require screening 100,000 to 1,000,000 members of a genetic library in parallel, and then rapidly detecting and isolating promising members for further analysis and optimization.

One of the challenges in the development of high throughput methods is that conventional liquid handling techniques such as pipetting, piezoelectric droplet dispensing, split pin dispensing, and microspritzing are generally unsuitable for rapidly loading or transferring liquids to or from plates of high density (e.g., plates having more than about 384 wells). For example, these techniques can cause substantial splashing, resulting, for example, in contamination of neighboring wells and loss of sample volume. Also, as the number of wells increases, the time necessary to reformat compounds from the previous generation of plates to the higher density plates generally increases, thus limiting the utility of higher density plates. Evaporation can also be problematic with times greater than a few seconds. Moreover, entrapped air bubbles can result in inconsistencies in the loading of small fluid volumes (e.g., less than about one microliter).

Significant bottlenecks in high throughput screening efforts include library storage, handling, and shipping. As the number of compounds in a library increases, the number of 96- or 384-well plates, and the total volume needed to store the libraries, also increases. For compounds that are stored in frozen solvent such as DMSO or water, thawing, dispensing, and refreezing pose the hazard of crystallization, precipitation, or degradation of some compounds, making it difficult to dispense accurate quantities in the future. Having samples stored in low-density plates requires a time consuming step of reformatting the samples into high-density plates before the high-density technology can be utilized.

SUMMARY OF THE INVENTION

The invention features methods of making devices, or "platens", having a high-density array of through-holes, as well as methods of cleaning and refurbishing the surfaces of the platens. The invention further features methods of making high-density arrays of chemical, biochemical, and biological compounds, having many advantages over conventional, lower-density arrays. The invention includes methods by which many physical, chemical or biological transformations can be implemented in serial or in parallel within each addressable through-hole of the devices. Additionally, the invention includes methods of analyzing the contents of the array, including assaying of physical properties of the samples.

In various embodiments, the reagents can be contained within the through-holes by capillary action, attached to the walls of the through-holes, or attached to or contained within a porous material inside the through-hole. The porous material can be, for example, a gel, a bead, sintered glass, or particulate matter, or can be the inner wall of a through-hole that has been chemically etched. In particular embodiments, the arrays can include individual molecules, complexes of molecules, viruses, cells, groups of cells, pieces of tissue, or small particles or beads. The members of the arrays can also, for example, function as transducers that report the presence of an analyte (e.g., by providing an easily detected signal), or they can function as selective binding agents for the retention of analytes of interest. Using these methods, arrays corresponding to a large plurality of human genes (e.g., using nucleic acid probes) can also be prepared.

On embodiment of the invention features a method of making a platen of a desired thickness having a plurality of through-holes. The method includes the steps of (a) providing a plurality (e.g., 2, 3, 5, 8, 10, 100, 1000 or more) of plates having upper and lower surfaces, wherein one or both of the upper and lower surfaces of at least some of said plurality of plates has continuous, substantially parallel grooves running the length of said surfaces; (b) bonding the upper surfaces of all but one of said plurality of plates to the lower surfaces of the other plates (i.e., the upper surface of the first plate is bonding to the lower surface of the second plate; the upper surface of the second plate is bonded to the lower surface of the third plate; and so on; the upper surface of the last plate is not bonded to anything else); and (c) if necessary to achieve the desired thickness, slicing the platen substantially perpendicularly to the through-holes, thereby creating a platen of a desired thickness having a plurality of through-holes. Step c) can optionally be repeated make a plurality of platens.

The plates can be made from any material that can be bonded (e.g., plastic, metal, glass, or ceramic), and each can have a thickness from, e.g., about 0.01 mm to 2.0 mm, preferably 0.1 mm to 1 mm; the grooves have a depth from, e.g., 0.005 mm to 2.0 mm (i.e., less than the thickness of the plates); and the grooves can have a width from, e.g., 0.1 mm to 1.0 mm.

The plates can be bonded in a configuration in which the grooves of one plate are substantially parallel to the grooves of each of the other plates, or can be bonded so that the grooves of certain plates are perpendicular to, or at acute angles to, the grooves of certain other plates.

In another embodiment, the invention features a device for the immobilization of probes, cells, or solvent. The device includes a platen (optionally having hydrophobic upper and lower surfaces) having a plurality of through-holes (e.g., from the upper surface to the lower surface), where at least some of the through-holes contain a porous material such as a gel (e.g., polyacrylamide), silica, sintered glass, or polymers for the immobilization of probes, cells, or solvent.

In still another embodiment, the invention features a method of making a platen having opposing hydrophobic surfaces and a plurality of hydrophilic through-holes. The method includes the steps of: (a) coating a plate with a material (e.g., gold, silver, copper, gallium arsenide. metal oxides, or alumina) that reacts with amphiphilic molecules (e.g., alkane thiols, alkanephosphates, alkane carboxylates); (b) forming through-holes in the plate (e.g., by microma-chining methods such as drilling, electrospark discharge machining (EDM), punching, stamping, or etching; and (c) treating (e.g., dipping or spraying) the plate with a solution or vapor of an amphiphilic molecule to provide a platen having hydrophobic coating on surfaces of the platen but not on the walls of the through-holes. The invention also includes the platens made by this method, as well as a method of regenerating the hydrophobic coating on the platen after use. This method includes the steps of: (a) removing residual hydrophobic coating, if any (e.g., by washing the platen with oxidant, reductant, acid, base, or detergent, or by heating, electropolishing, irradiating, or burning); and (b) treating the platen with a solution or vapor of an amphiphilic molecule to regenerate the hydrophobic coating.

In yet another embodiment, the invention features a method of selectively making a coating on the surfaces of a platen having a plurality of through-holes. The method includes the steps of: (a) selectively coating the surfaces of the platen with a material that reacts with amphiphilic molecules; and (b) treating the platen with a solution or vapor of an amphiphilic molecule to regenerate the hydro-phobic coating.

Still another embodiment of the invention features a platen having two opposing surfaces and a plurality of through-holes extending between the surfaces. The surfaces have different chemical properties relative to the walls of the through-holes, such that the walls and surfaces can be independently functionalized. For example, the walls can be coated with gold (e.g., by coating the entire platen, including both the walls and the opposing surfaces with gold, and then electropolishing the surfaces to remove the gold therefrom), allowing the walls to be rendered hydrophobic upon treat-ment with alkane thiols. Conversely, the surfaces (but not the walls) could be coated with metal oxides so that alkane-phosphates can be bound thereto.

In another embodiment, the invention features a method of making a plastic platen of a desired thickness, having through-holes. The method features the steps of: a) potting a plurality of capillaries (e.g., glass or plastic capillaries) in the through-holes of a stack of platens comprising at least two platens having through holes; b) separating adjacent platens by a distance equal to the desired thickness; c) injecting a plastic-forming material into the space between the separated platens; d) forming (e.g., heat-setting or curing) the plastic; and e) slicing at the interface between the platens and the plastic to form the chips. The plastic-forming material can be, for example, a photo-, thermo-, or chemical-curable material such as a UV-curable material, e.g., poly-methylmethacrylate (PMMA), polystyrene, or epoxy, and the forming step can entail exposing the material to ultra-violet light; or the plastic-forming material can be a molten thermoplastic material and the forming step can involve cooling the material.

In still another embodiment, the invention features a method of making a plastic chip of a desired thickness, having through-holes. The method features the steps of: a) potting a plurality of fibers or wires in the through-holes of a stack of platens comprising at least two platens having through holes; b) separating adjacent platens by a distance equal to the desired thickness; c) injecting a plastic-forming material into the space between the separated platens; d) forming the plastic; e) withdrawing the fibers or wires from the plastic to form through-holes; and f) slicing at the interface between the platens and the plastic to form the chips.

Still another embodiment of the invention is a method of creating a chemical array. The method includes the steps of: a) providing a platen having a plurality of through-holes and two opposing surfaces; b) applying a mask to one or both surfaces of the platen to block at least some of the through-holes, while leaving other through-holes open; c) exposing a surface of the platen to a reagent (e.g., e.g., a liquid, a gas, a solid, a powder, a gel, a solution, a suspension such as a slurry, a cell culture, a virus preparation, or electromagnetic radiation; e.g., by spraying the platen with a solution or suspension of the reagent, or by condensing, pouring, depositing, or dipping the reagent onto the platen) so that the reagent enters at least one of the open through-holes; and d) repeating steps b) and c) (e.g., at least once, generally at least three times; for creation of nucleic acid arrays, the steps can be repeated four times the length of the desired nucleic acid chains; for creation of protein arrays, the steps can be repeated twenty times the length of the desired peptide chains) with at least one different mask and at least one different reagent to create a chemical array. The masks can be reusable or disposable, and can be applied mechanically (e.g., robotically) or manually. The mask can, in some cases, initially include the reagent (e.g., absorbed onto or contained within it). The mask can be flexible or rigid, for example, and can be made of a polymer, an elastomer, paper, glass, or a semiconductor material. The mask can, for example, include mechanical valves, pin arrays (e.g., posts, pistons, tubes, plugs, or pins), or gas jets. In some cases, the "applying" step forms a hermetic seal between the mask and the platen. The mask can also be translated (e.g., moved between the repetitions of the method) to expose different through-holes. In some cases, the mask has co-registration pins and holes such that alignment of pins and holes in the mask register with the through-holes in the platen. In these cases, multiple masks can be made part of a flexible tape, and the multiple masks are registered with the through-holes of the platen by advancing the tape (e.g., the masks can be on a spool, ribbon, or roll, and can be advanced in a manner analogous to the advancing of film in a camera). Arrays created by any of these methods are also considered to be an aspect of the invention.

In yet another embodiment, the invention features a method of creating a chemical array. The method includes the steps of: a) providing a platen having a plurality of through-holes and two opposing surfaces; b) applying a mask that has one or more reagents on its surface to one or both surfaces of the platen to transfer the reagent from the mask to at least some of the through-holes; and c) repeating step b) with at least one different mask and at least one different reagent to create a chemical array.

The invention also features a method for separating samples within a chemical array in a platen. The method includes the steps of a) providing a platen having a plurality of through-holes and two opposing surfaces; b) electrophoretically transporting a charged reagent into at least some of the through-holes by placing the platen into an electrophoresis apparatus containing the reagent and applying an electric field parallel to the through-holes; and c) repeating step b) with at least one different reagent to create a chemical array.

In still another embodiment, the invention features a method of creating a spatially addressable array. The method includes the following steps: a) providing a platen having a spatially addressable plurality of discrete through-holes each having an inner wall, wherein said platen has opposing hydrophobic surfaces; and b) covalently or non-covalently immobilizing at least one reagent or probe on the inner walls of at least some of the through-holes or on a bead contained within at least one of the through-holes to form a spatially addressable array. In this method, the through-holes can be either non-communicating (i.e., the contents of adjacent through-holes do not mix with each other) or selectively communicating (i.e., the walls of at least some of the through-holes act as semi-permeable membranes) through-holes. In some cases, the method can also include the step of: c) flowing reagents (e.g., monomers, wash solutions, catalysts, terminators, denaturants, activators, polymers, cells, buffer solutions, luminescent and chromatogenic substrate solutions, beads, heated or cooled liquids or gases, labelled compounds, or reactive organic molecules) into or through a predetermined subset of the through holes.

Yet another embodiment of the invention is a method of creating a stochastic array. The method includes a) providing a platen having a plurality of through-holes; and b) applying each of a plurality of reagents to the through-holes in a random or semi-random manner (e.g., spatially random or random with respect to distribution of reagents) to create a stochastic array. The "applying" step can include, for example, providing a plurality of dispensing devices addressing at least some of the through-holes, dispensing different combinations of reagent solutions (e.g., as solutions, neat, or in suspension) into each through-hole, and repositioning the dispensing devices at least once to address a different set of through-holes. In this case, the method can also involve dispensing a fluid that is immiscible with the reagent solutions into at least one through-hole.

In another embodiment, the invention features a method of identifying combinations of reagents having a biological, chemical or physical property of interest. The method involves, for example, the use of radiolabelled probes, or the measurement of chemiluminescence. The method features the steps of: a) creating a stochastic array using the above method; b) assaying the stochastic array for combinations having a property of interest; and c) identifying the reagents that have the property of interest. Non-limiting examples of properties of interest include catalysis (see, e.g., Weinberg et al., *Current Opinion in Solid State & Materials Science*, 3:104–110 (1998)); binding affinity for a particular molecule (see, e.g., Brandts et al., *American Laboratory* 22:3041 (1990); or Weber et al., *J. Am. Chem. Soc.* 16:2717–2724 (1994)); ability to inhibit particular chemical and biochemical reactions; thermal stability (see, e.g., Pantaliano et al., U.S. Pat. Nos. 6,036,920 and 6,020,141); luminescence (see, e.g., Danielson et al., *Nature* 389:944–948 (1997)); crystal structure (see, e.g., Hindeleh et al., *Journal of Materials Science* 26:5127–5133 (1991)); crystal growth rate; diastereoselectivity (see, e.g., Burgess et al., *Angew. Chem.* 180:192–194 (1996)); crystal quality or polymorphism; surface tension; (see, e.g., Erbil, *J. Phys. Chem. B.*, 102:9234–9238 (1998)); surface energy (see, e.g., Leslot et al., *Phys. Rev. Lett.* 65:599–602 (1990)); electromagnetic properties (see, e.g., Briceno et al., *Science* 270:273–275 (1995); or Xiang et al., *Science* 268:1738–1740 (1995)); electrochemical properties (see, e.g., Mallouk et al., Extended Abstracts; Fuel Cell seminar: Orlando, Fla., 686–689 (1996)); and optical properties (see, e.g., Levy et al., *Advanced Materials* 7:120–129 (1995)); toxicity, antibiotic activity, binding, and other biological properties; fluorescence and other optical properties; and pH, mass, binding affinity, and other chemical and physical properties.

In another embodiment yet, the invention features a method of loading a platen having a plurality of through-holes, where the platen has opposing surfaces (e.g., the surfaces are hydrophobic and the through-holes have hydrophilic walls). The method includes the steps of: a) dipping the platen into a liquid sample (e.g., a neat liquid, a solution, a suspensions, or a cell culture) that includes a sample to be loaded into the through-holes, thereby loading at least some of the through-holes with the sample; and b) passing the platen through a liquid that has an affinity for the surfaces of the platen but that is immiscible with the liquid sample, thereby cleaning the surface of the platen of excess sample mixture (e.g., by adding, on top of the sample mixture, the immiscible liquid, where the liquid has a lower density than the sample mixture (e.g., mineral oil); and removing the platen from the sample mixture through the liquid; device comprising a barrier between the sample and the liquid).

The invention also features another method of loading a platen having a plurality of through-holes, where the platen has opposing surfaces. The method includes: a) dipping the platen into a liquid sample comprising a sample to be loaded into the through-holes, thereby loading at least some of the through-holes with the sample; and b) contacting the platen with a liquid that has an affinity for the surfaces of the platen but is immiscible with the liquid sample, thereby cleaning the surface of the platen of excess sample mixture.

The invention also features a method of maintaining the viability of an aerobic organism in a platen having a plurality of through-holes. The method includes the steps of: a) loading the aerobic organism (e.g., a cell or an embryo) into at least some of the through-holes of the platen, and b) submerging the platen into a gas permeable liquid. The organism can be, for example, in a fluid such as a growth medium, in which case the gas permeable liquid should be immiscible with the fluid. The method can also include assaying one or more physical properties of the aerobic organism. The gas permeable liquid can be, for example, a fluorocarbon such as perfluorodecalin, a silicone polymer, or a monolayer (e.g., a monolayer of a lipid or high molecular weight alcohol.

In another embodiment still, the invention features a method of mixing volatile samples with other samples (whether volatile or non-volatile). The method include the steps of: a) providing a platen having a plurality of through-holes; b) optionally loading some or all of the through-holes with one or more non-volatile samples (if any); c) loading at least some of the through-holes of the platen with one or more volatile samples to allow the samples in each through-hole to mix with other samples in the same through-hole; and d) submerging the platen in a liquid immiscible with the volatile samples, where steps b), c) and d) can be performed in any order. In preferred embodiments, step d) is performed prior to introduction of volatile samples. The samples to be mixed can be initially provided in two separate platens that are contacted while submerged in said immiscible liquid to allow mixing. The immiscible liquid can be, for example, a fluorocarbon, a silicone polymer, mineral oil, or an alkane.

The invention also features a method of mixing an array of samples. The method entails: a) providing a platen having a plurality of through-holes, wherein at least some of the through holes are loaded with a first sample or set of samples; b) providing a substantially flat surface comprising an array of a second sample or set of samples, wherein the second sample or set of samples on the flat surface can be registered (e.g., the second sample or set of samples can be arranged in a spatial pattern that allows it to line up with at least some of the through-holes of the platen) with the sample in the platen; c) registering the platen with the array of the second sample or set of samples on the flat surface; and d) contacting the platen with the flat surface, wherein the sample in the platen is aligned with the sample on the flat surface. This method can be used, for example, to avoid cross-contamination; also, registering and contacting can be done simultaneously. In some cases, either the first or second sample or set of samples can include one or more probes. The method can also include the further step of analyzing a physical property (such as fluorescence or other optical properties, pH, mass, binding affinity; e.g., using radiolabelled probes and film, chemiluminescence) of a sample contained in the platen. In some cases, the flat surface can also include a hydrophobic pattern matching the pattern of the platen array (e.g., to prevent cross-contamination).

In another embodiment, the invention features a method for transferring a reagent or probe to a receptacle (e.g., into a bottle, a tube, another platen, a microtiter plate, or a can) from a specific through-hole of a platen comprising a plurality of through-holes. The method includes the steps of: a) placing the platen over the receptacle; and b) applying a burst of gas, liquid, solid, or a pin (e.g., a piston, a tube, a post, a plug) to the specific through-hole to transfer the reagent or probe into the receptacle. The burst of gas, liquid, or solid can be generated, for example, with a syringe, or by depositing a photodynamic or photothermal material (carbon black, plastic explosives, water droplets) in or above the through-hole, and then exposing the photodynamic or photothermal material to a laser beam of frequency and intensity suitable to activate the photodynamic or photothermal material.

In another embodiment, the invention features a device for filling or draining through-holes in a platen having a plurality of through-holes. The device includes: a) a holder adapted to accept the platen; b) a nozzle having an aperture of a suitable size to inject a sample into a single through-hole in said platen; and c) a valve that controls a flow of a sample through said nozzle, wherein the holder and nozzle can move with respect to each other. The nozzle can be, for example, positioned so as to contact the platen (or not). The device can optionally include a microplate (e.g., a microtiter plate) positioned to receive samples from the platen, as well as a computer that can control the valve and control the positions of the holder and nozzle (and, optionally, the microplate) relative to one other. The optional microplate, the holder, and the nozzle can, in some cases, be moved independently of each other in at least two dimensions. Alternatively, the nozzle can be held in a single position while the holder and nozzle can be moved independently of each other in at least two dimensions.

In another embodiment, the invention features a method of analyzing the kinetics of one or more reactions occurring in at least one of the through holes of a platen. The method includes: a) providing a first platen having a plurality of through-holes, wherein the through-holes are loaded with a first sample or set of samples; b) introducing the platen into a detection device; c) introducing a second platen having a plurality of through-holes into the detection device, wherein the through holes are loaded with sample or reagent; d) registering and contacting the platens such that contents of the through-holes of said first platen can mix with contents of corresponding through-holes of said second platen; and e) detecting a change in a physical property of the contents of at least some of the through-holes over time.

In another embodiment, the invention features a method of analyzing a physical property of a sample in an array. The method includes the steps of: a) providing a platen having a plurality of through-holes, where the through-holes are loaded with a sample; b) placing the platen between two partially transmitting mirrors; c) illuminating the samples through one of the mirrors (e.g., with a laser, atomic lamp, or other light source, including white light sources); and d) detecting optical output from the sample. Optionally, mirrors that reflect at only one wavelength and transmit at all others can be used, and non-linear optical effects can also be observed. The "imaging" step can involve, for example, measuring light emanating from the array or measuring light emitted from the mirror opposite from the illumination source. The platen can also be placed within a laser cavity, and an optical gain medium can be positioned between the two mirrors.

The invention also features a method of measuring sample output from an array. The method includes the steps of: a) providing a platen having a plurality of through-holes, wherein the through-holes are loaded with sample; b) introducing the sample into an array of capillaries; c) eluting the samples through the capillaries using pulse pressure, creating a non-continuous flow; d) spotting the eluting samples onto a surface that is moving relative to the capillaries (e.g., a web, a tape, a belt, or a film), wherein the spots are discrete and no mixing of the samples occurs; and e) analyzing a physical property of the spots.

The invention also features a method of storing a plurality of samples in an assay-ready, high-density format. The method includes the steps of a) providing a platen having a plurality of through-holes; b) loading the through-holes with the samples (e.g., small molecules) dissolved in a mixture comprising two solvents, a first solvent having a low vapor pressure (e.g., dimethyl sulfoxide (DMSO)) and a second solvent having a higher vapor pressure relative to the first solvent (e.g., ethanol; preferably, both solvents are inert and are able to dissolve the sample); and c) evaporating the second solvent to result in a plurality of samples in first solvent (preferably as films on the walls of the through-holes). The volume of the first solvent in each solution can be, for example, less than about 25 nl (e.g., less than 10 nl, 1 nl, 250 pl, 100 pl, or even less than about 25 pl; e.g., a "microdroplet"). In some embodiments, the sample dissolved in the first solvent forms a film on the wall of a through-hole.

The invention features a method of forming a high throughput assay. The method includes: a) providing a platen having a plurality of through-holes, wherein at least some of the through-holes contain a sample dissolved in a solvent having a low vapor pressure (such as a array of samples prepared for storage according to the above method); b) cooling the platen to a temperature sufficient to freeze the dissolved sample, c) dipping the platen into a solution comprising a reagent, wherein the temperature of the solution is less than the freezing point of the sample, but greater than the freezing point of the reagent solution, d) removing the platen from the reagent solution, and e) warming the platen to a temperature greater than the freezing point of the sample. The reagent solution can be, for example, an aqueous solution.

Yet another embodiment of the invention features a filtration device, having first and second platens, each having a plurality of through-holes, and a semi-permeable membrane. The platens are aligned such that the through-holes of the first platen are substantially aligned with the through-holes of the second platen and the membrane is sandwiched in between the two platens. Optionally, the platens can have hydrophobic surfaces. The semi-permeable membrane can be, for example, a nitrocellulose membrane, or can include a layer of cells.

A "spatially addressable through-hole" has a position and dimensions that are known to a high degree of certainty (e.g., relative to a reference position on the device). The degree of certainty is sufficient that the through-holes of two platens placed one on top of the other can align, allowing reagents to transfer in a parallel fashion. The degree of certainty is also sufficient such that a sample in any given through-hole can be retrieved by a robotic device that knows only the position in which that hole should be found relative to a reference point on the device. The term "planar array of through-holes" refers to an array of through-holes on a platen such as that described in PCT application WO99/34920.

A "reagent" is a chemical compound, a gas, a liquid, a solid, a powder, a solution, a gel, a bead, or electromagnetic radiation.

The term "probe" or "chemical probe" refers to a chemical, biological, mechanical, or electronic structure that detects a specific analyte by a specific binding or catalytic event. The binding or catalytic event can be transduced into a signal readable by an operator. One type of chemical probe is an affinity probe (e.g., a specific nucleic acid that binds to another nucleic acid). Examples of mechanical probes include a cantilever that has a ligand immobilized on its surface and a material whose properties (e.g., strain, inertia, surface tension) change in response to a chemical or biological event.

The term "chemical detection event" refers to a chemical reaction between molecule(s) of interest and probe molecule(s) that in turn produces a signal that can be observed by an operator. For example, the hydrolysis of fluorescein di-β-galactoside by the enzyme β-galactosidase, to produce the fluorescent molecule fluorescein, is a chemical detection event. In some cases, the chemical detection event can involve a series of chemical reactions triggered by an initial interaction of analyte and probe (e.g., activation of a signal transduction pathway in a probe cell by the binding of a ligand to a surface receptor).

The term "linker molecule" means a molecule that has a high affinity for or covalently links to the surface of a platen or bead. The linker molecule can have a spacer segment such as a carbon chain, and can also have a functional group at its end to enable attachment of probe molecules covalently or with high affinity.

The term "immobilized" means substantially attached at the molecular level (i.e., through a covalent or non-covalent bond or interaction).

The term "photocleavable compound" refers to a compound that contains a moiety that, when exposed to light, dissociates into multiple independent molecules.

The term "small molecule" refers to a molecule having a mass less than about 3000 daltons.

The term "hybridization" refers to complementary, specific binding of two or more molecules (e.g., nucleic acids) to one another.

"Solid phase synthesis" refers to a chemical synthesis process in which at least one of the starting materials in the synthesis reaction is attached to a solid material such as a polymer bead, a gelatinous resin, a porous solid, or a planar surface.

The term "blotter" refers to a material capable of capturing excess liquids by absorption.

The term "bead" means a small particle, generally less than about 1 mm (e.g., less than about 100 $\mu$m) in any dimension, with the ability to have reagents attached to its surface or stored in its interior. A bead can be made from one or more of a variety of materials, including organic polymers, glass, and metals. The reagent is typically attached to the bead by chemical reaction with a reactive functional group such as a carboxyl, silanol, or amino group on its surface. Reagents can, for example, be confined to the bead by covalent chemical attachment or by physical adsorption to the bead surface. The bead shape can be nearly spherical, irregularly shaped, or of an intermediate shape.

The term "stringency" refers to the degree to which non-specific molecular interactions are disrupted during a washing step.

The term "electrophoretic washing" refers to the removal of non-specifically bound, ionic molecules from a probe by applying an electric field.

"Specific interactions" are interactions between two molecules resulting from a unique three-dimensional structure of at least one of the molecules involved. For example, enzymes have specific interactions with transition state analogues due to their evolution toward stabilizing reaction intermediates.

The term "micro-plate" refers to a collection plate used to transfer the contents of the through-holes of an array, where no cross contamination of the through-holes occurs in the transfer.

The term "micro-droplet" means a drop of liquid having a volume of 50 nl or less (e.g., less than about 50 nl, 25 nl, 10 nl, 5 nl, 1 nl, 500 pl, 250 pl, 100 pl, 50 pl, or less).

The term "physical properties" means any measurable property of an object or system, including electrical, magnetic, optical, thermal, mechanical, biological, nuclear, and chemical properties.

The new methods have numerous advantages. For example, the new methods allow optimization of processes in a parallel manner. For instance, synthesis of a particular molecular species often requires tedious quantitative investigation of different synthetic methods with a view towards optimizing product yield. Using the new methods, process parameters can be varied on a through-hole-by-through-hole basis in the array, and the product analyzed to determine the protocol best suited for high yield synthesis.

Another advantage of the invention over conventional arrays of chemical probes on a planar substrate is that each chemical detection event takes place in a physically isolated container (i.e., the through-hole), allowing amplification of the signal by catalysis (e.g., releasing detectable molecules into the solution contained in each through-hole). Such detectable molecules include, for example, fluorescent products of a fluorogenic enzyme substrate, and chromogenic products of a chromogenic substrate. Physical isolation of samples retained in the array also prevents cross-contamination by eliminating lateral communication between the through-holes.

Another advantage of the invention is that each through-hole can have a precise and known spatial location in the array. Each through-hole is then spatially addressable, thereby facilitating the insertion and removal of liquids from each through-hole, the analysis of the contents of each through-hole, and the alignment of multiple arrays for highly parallel transfer of reagents.

Another advantage of the invention is that the relative volumes of the members of two arrays can be easily adjusted by changing the depth of one array with respect to the other.

Still another advantage of the invention is that substances that bind to chemical probes contained in the through-hole array can easily be recovered as distinct samples for further analysis. For example, the bound contents of the well can be eluted onto a planar substrate for analysis by matrix-assisted laser desorption and ionization (MALDI) or surface-enhanced laser desorption and ionization (SELDI) mass spectrometry, or nuclear magnetic resonance (NMR) spectroscopy. Alternatively, the contents of the through-hole can be electro sprayed directly from the through-hole into a mass spectrometer. The contents of the through-hole can also be crystallized and analyzed with x-ray or electron diffraction techniques (e.g., to determine crystal structure). This aspect of the invention allows for sensitive detection of unlabelled analytes.

Yet another advantage of the invention is that the samples can be introduced or removed from the platen by electrophoresis, as the through-holes can allow for conduction of an electric field.

Another advantage of the invention is that samples are accessible from both sides of the platens. This means, for example, that samples can be removed from the platens by applying pressure, an air or gas stream, or an explosive charge to a through-hole of interest and then collecting the material from the opposing face of the platen. Alternately, samples can be sucked out of the platen without creating a vacuum. Thus, the volume of the samples in not limited by the current state-of-the-art microfluidics techniques, and a minimum quantity of fluid is lost upon the collection of the sample. A pressure can be applied, for example, in the form of a solid pin (acting, e.g., as a piston), or in the form of a burst of inert gas. Another implication of this advantage is that it is relatively easy to perform electrospray ionization mass spectrometry directly from the platen. Simultaneous measurement of luminescence from two spectrally distinct luminescent probes located in the microchannel array can be performed in either a trans- or epi-illumination optical configuration, including, for example, a light source, an optical filter, and a CCD camera. Optical signals can be collected from both sides of the platen simultaneously.

The numerous samples contained in the platen can be rapidly transferred to a flat surface or membrane, facilitating processes such as SELDI mass spectrometric analysis and growth of bacterial cells (e.g., cells contained in the through-holes), to form individual colonies for storage and further analysis. Transfer from a planar material to the array can also be accomplished, as in electroblotting from a polyacrylamide 2-D protein gel into the array.

Advantageously, the surface area of the liquid exposed to the environment is minimized by the high aspect ratio geometry, thus limiting evaporation.

Still another advantage of the new methods is that the sample contained in a given through-hole constitutes a small thermal mass and can, therefore, reach thermal equilibrium quickly and uniformly. The fact is relevant, for example, to synthetic methods that involve heating and/or cooling steps (e.g., replication of nucleic acids using the polymerase chain reaction, PCR).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 4 is an illustration of a method for producing a mask by use of UV curable epoxy.

FIG. 5 is an illustration of a method for producing a mask by use of an array of pins having a precision fit into a matching array of through-holes.

FIG. 20 is an illustration of a method of manufacturing a platen having a plurality of through-holes and two opposing surfaces, by bonding together multiple grooved surfaces.

DETAILED DESCRIPTION OF THE INVENTION

The invention provides methods of creating, storing, and screening diverse chemical and biological compositions, each contained in a through-hole that traverses a platen, as well as methods for making and using platens. In certain embodiments, the methods include transmitting reagents to a selected group of holes in a dense array of through-holes. Additional rounds of reagent transmission are provided as needed. The invention also provides for placing a series of masks over a planar array of through-holes and flowing reagents through the masks to build a defined pattern of probes or reagents such that the contents of each through-hole can be known. In an alternate embodiment, the invention provides distributing probe-holding particles, such as beads or cells, into the array of through-holes. Such probes include, but are not limited to, nucleic acids, peptides, small molecules, and chemical sensing cells. Uses of the arrays include screening of genetic libraries, producing and screening compound libraries for discovery of pharmaceutical leads, optimization of reaction conditions, gene expression analysis, clinical diagnostics, genomics, functional genomics, pharmacogenomics, structural genomics, proteomics, production and optimization of industrial catalysts, chemical genetics, identification of suitable conditions for reactions (e.g., conditions suitable for protein crystallization), genotyping, polymorphism analysis, examination of RNA expression profiles in cells or tissues, sequencing by hybridization, and recombinant enzyme discovery.

Figure 1:
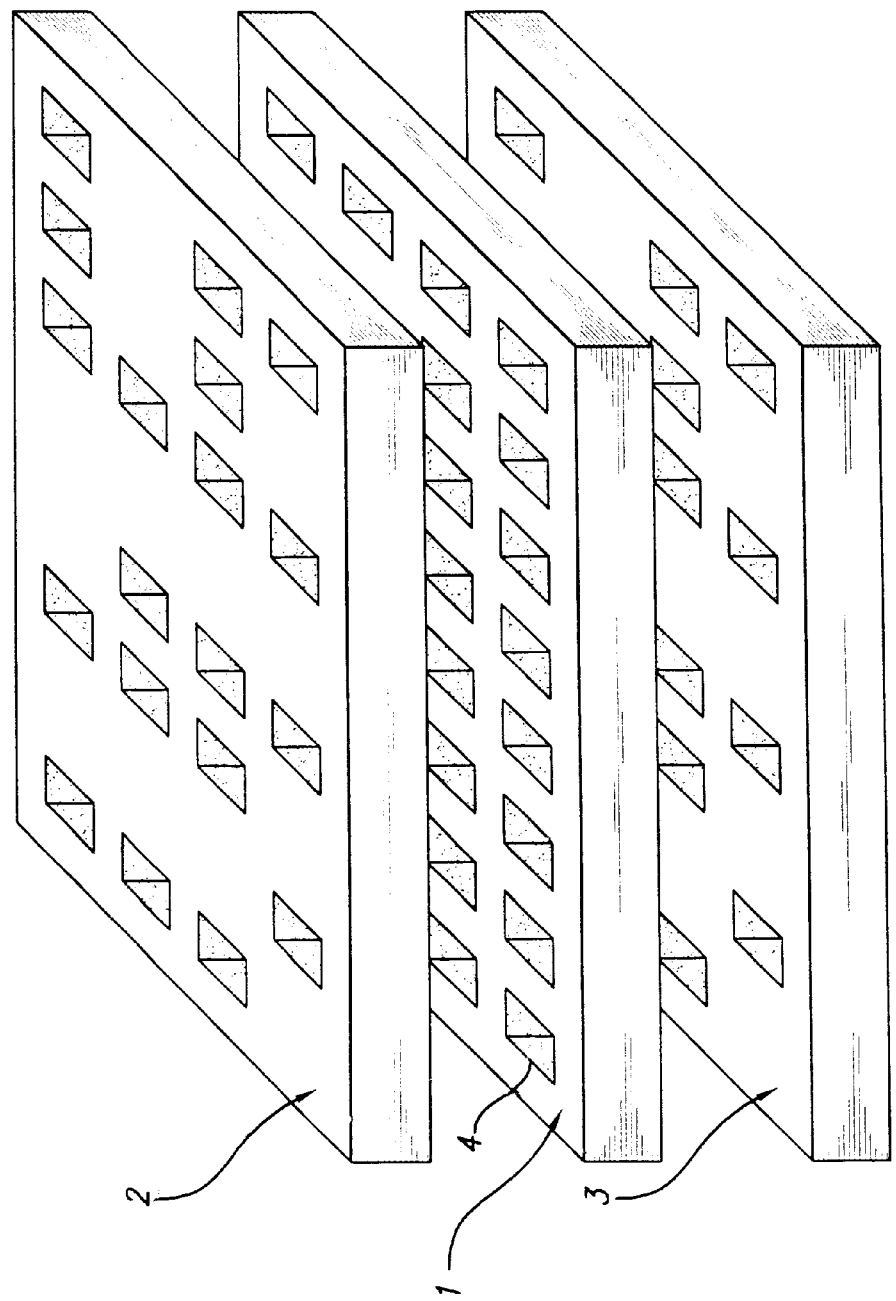
FIG. 1 is an exploded top corner view of a platen with top and bottom masks.

A platen having a high-density array of through-holes in accordance with one embodiment of the present invention is illustrated in FIGS. 1 (top view) and 2 (cross-sectional side view). The platen can be made of silicon or other rigid materials, such as metal, glass, or plastic. The platen material can be chemically inert, or can be rendered so by appropriate surface treatments.

Referring to FIG. 1, each through-hole has a square cross-section, although circular or rectangular cross-sections can alternatively be used. The diameter of each through-hole is less than 1 mm (e.g., less than about 600 $\mu$m, 300 $\mu$m, 100 $\mu$m, 10 $\mu$m, 1 $\mu$m, or 100 nm), typically 200–250 $\mu$m, and the depth of the platen can be 10–2000 $\mu$m or more, generally about 250–1000 $\mu$m.

Greater depths can be achieved using a bundle of glass capillaries. Alternatively, platens having greater depths can achieved by bonding together multiple surfaces having parallel grooves, creating a long three dimensional object having through-holes running throughout the length of the object. This object can be subsequently sliced horizontally, allowing flexibility in the depth of the through-holes. The result is the ability to use arrays with compatible positions of through-holes, wherein the depths of the through-holes can vary from array to array.

For spatial addressability, center-to-center spacing of through-holes should be fairly precise. Hole-to-hole spacing depends on the dimension of the through-holes within the platen. The though-holes can be arranged in regular rows and columns, hexagonal arrays, or other configurations (e.g., groupings of through-holes into smaller sub-arrays). Multiple platens can be fabricated with the same arrangement of through-holes so that the pattern is reproducible, and each through-hole can be identified by its own address within the array.

When three platens having through-holes are stacked, the total volume of a single channel (i.e., three through-holes stacked) is typically ~100 nl. Using this volume as an example, if the entire channel were filled from a dense yeast cell culture (~$10^7$/ml), each channel would thus contain approximately $10^3$ yeast cells. Based on a yeast cell volume of 70 $\mu$m$^3$, the maximum number of cells per 100 nl channel is on the order of $10^6$. A minimum of 100 cells per microchannel can be adequate to compensate for cell-to-cell variability of yeast cell response to the bioassays. However, this volume can vary depending not only on the diameter of the through-holes, but on the depth of the through-holes. This ability to vary the volume of samples allows flexibility, enabling the use of a wider variety of materials, concentrations, and reaction conditions.

Optional features such as binary identification codes, or holes and grooves for indexing and alignment, can also be incorporated into each platen.

I. Methods of Making Devices Having Arrays of Through-holes

Fabrication of an Array of Through-holes by Casting in Resin

Conventional technologies for manufacturing high-density through-hole arrays include micro-machining, electrospark discharge machining (EDM), or chemical etching. Alternatively, the arrays can be cast in a polymer or resin. A casting mold can be designed such that the inner diameter of the mold will be equal to or larger than the final outer diameter of the array device. The depth of the casting mold can be as little as 0.5 mm for a single array, or 1 meter or longer. In the case where a long block of resin is cast, the resin can be cross-sectioned into slices of desired thickness and the surfaces can be polished or smoothed. The through-holes can be defined in the cast by several methods. Solid wire, fiber, or an array of pins of the desired geometry and diameter can be arranged within the casting mold. If necessary, the wire, fiber or pins can be immobilized in place with the use of one or more positioning jigs within the casting mold. The chemistries of the wire, fiber, or pins must be chosen such that they will not form a permanent bond with the resin or polymer as it solidifies, so that they can be pulled out to produce the through-holes. For example, the fibers may be ethyleneterephthalate and the resin is polymethylmethacrylate (PMMA). Alternatively, the surfaces of the wire, fiber, or pins can be coated with a release agent such as an oil, a fluoropolymer, water, or a polymerization inhibitor that will facilitate the removal of the wire, fiber, or pins from the cast resin or polymer once the final curing, setting, or polymerization is complete.

In an alternate system, the through-holes can be defined by positioning an array of hollow tubing or capillaries within the casing mold. The hollow tubes can be immobilized within the casting mold in a positioning jig. Use of tubing of different internal diameter results in an array with through-holes of different diameters. The chemistry of the hollow tubes and polymer will ideally be chosen such that a permanent bond will form between the outside hollow tube and the resin or polymer that is cast. The inner surface of the hollow tubes will then make up the through-holes of the array. The hollow tubes can be made of glass or fused silica, a polymer, or a metal.

The chemistry of the resin or polymer that is cast can be selected such that the surface of the array device is of a desired hydrophobic or hydrophilic character. The chemistry of casting resins, such as acrylate or polystyrene, can be modified with hydrophobic groups to result in an array with the desired surface chemistry. Alternatively, the surface chemistry of the array device can be modified with standard techniques after slicing and polishing. In addition, the chemical or physical properties of the polymer can be modified by the addition of other materials. For example, to control the electrical conductivity of the device, particles of a conductive metal can be mixed into the resin or polymer prior to casting the mold to confer conductivity to the device. Generally, the more metal particles that are mixed with the resin or polymer prior to casting, the greater the conductivity of the devices will be.

Additives to the resin or polymer can be used to improve the sensitivity of optical imaging of the array. For example, metal particles can be added to make the material between the through-holes. The metal particles enable light to scatter, causing a fluorescent signal generated by a probe in a through-hole to reflect toward the detector and to prevent cross-talk of signals. Alternatively, carbon black may be added to make the material, preventing cross-talk and minimizing signal from light scattered off the surface of the array. More preferably, a combination of a light scattering agent such as titanium dioxide and a light absorbing agent, such as carbon black are added to the resin or polymer to achieve maximum optical density between the holes.

Using hollow tubes in the casting mold to form through-holes allows the chemical properties of the tubes to be varied according to the needs of the application. Tubes manufactured from a biologically inert polymer (e.g., polyetheretherketone (PEEK) or poly(tetrafluoroethylene) (PTFE)) are desirable for some applications. Alternatively, fused silica tubing can be used to form the through-holes. The interior surface of the fused silica can be derivatized prior to casting, allowing for virtually any level of desired hydrophilicity or hydrophobicity. A metal or alloy tubing can also be used to form the through-holes of the array. Metal tubing can be coated to make it biocompatible. For example, metals can be coated with thin layers of gold and the gold surfaces can be readily coated with a variety of reagents possessing thiol moieties.

The inner surfaces of the tubes or capillaries can, for example, be coated with materials that facilitate the use of the resulting slices as a probe array. For instance, each tube or capillary can be coated with a different nucleic acid probe, so that when the block of resin is sliced, the resulting platens can be used as genosensors. Alternatively, the probes can be immobilized on a porous material contained in the capillaries.

Once a block is cast from the desired resin or polymer, it can be sliced to an appropriate thickness to form a platen having an array of through-holes. In certain embodiments, the thickness of the platen ranges from 0.2 to 25.0 mm. However, using this technique, arrays of through-holes can be manufactured having the same length as the casting mold that is used. If desired, casts that are many meters in length can be prepared. Standard techniques for producing silicon wafers by slicing and polishing silicon ingots in the semiconductor industry can be directly applied to the manufacture of an array of through-holes. Flowing a coolant through the through-holes in the cast array while slicing can prevent heat buildup that could otherwise melt the polymer or degrade coatings or probes inside the holes. Examples of coolants include cold water, cold aqueous ethylene glycol, and cold isopropanol.

If solid wires are arranged in the cast and the resulting block is then sliced, the wires can be eroded by electrodeposition onto a plate in an electrochemical cell or by chemical degradation such as by placing the slice in concentrated nitric acid to give an array of through-holes. The slices can be bonded to a metal sheet, the polymer eroded, and the slices used as an electrode for production of through-hole arrays by sink-EDM. The polymer can be eroded by chemical means, melted, or burned off.

Method of Making an Array by Stacking and Bonding Multiple Grooved Surfaces

One method of manufacturing an array of through-holes is to stack and bond together grooved plates having upper and lower surfaces, creating a three-dimensional array. (See Fig. 20 (1)–(2).) Any number of materials can be used to manufacture the array of through-holes including, but not limited to, silicon, glass, plastics, resins, or metals. Depending on the material used, grooves can be machined into the individual surfaces using a variety of techniques (for example, micro-machining, chemical etching, embossing, or stamping). The depth and width of each groove determines the dimensions of the through-holes in the completed platens and can be machined according to the desired specifications.

A precise layering or stacking of the grooved plates into a three-dimensional array can be accomplished with the use of an external or internal jig into which each surface is precisely placed. Alternatively, registration devices, (for example notches, posts, tongues, etc.) can be precisely integrated into each surface to facilitate accurate stacking. After stacking the individual grooved surfaces, they are bonded together in a permanent manner. The use of traditional adhesives to bond the plates together is a disfavored approach because excess adhesive can migrate into the grooves and result in the blockage of some of the through-holes. A preferred method for the bonding process is the use of a combination of elevated temperature and pressure, resulting in a fusion of the chosen materials. In some cases, one or both surfaces of the grooved platens are coated with a material (for example, gold) that, upon the application of an appropriate amount of temperature and pressure, diffuses into the surfaces and results in a permanent bond. The grooved plates can be made from materials that include a thermoplastic, a ceramic, a glass or a metal such as silicon.

In a preferred embodiment, the width of each of the grooved plates is equivalent to the width of the final platen of through-holes, but the length of each grooved plate is much larger than the desired thickness of the final platen of through-holes. This results in a three-dimensional array of through-holes that is much thicker than required. Individual platens of through-holes can then be precisely cut from this thick block to the desired specification. (See e.g., Fig. 20 (2)–(3).) The platens can further require polishing after they have been cut in order to yield an optically flat surface. The required surface chemistries are then be applied to the platens. An advantage of this method of manufacturing is the creation of platens with straight-walled through-holes that are much deeper than those made using traditional micro-machining technology.

Minor misalignments in the stacking of the individual grooved plates can result in small imperfections in the registration of the through-holes in the final platens. This can interfere with operations using the platens of through-holes (for example, stacking of two or more platens to initiate massively parallel reaction). However, even if minor errors in positional registration exist, adjacent slices cut from each thick array of through-holes will be a near-perfect match and the required stacking operations can be accomplished.

Formation of a Silicon Oxide Layer

In one embodiment, a dense array of through-holes is produced in a silicon wafer. A silicon oxide layer is created uniformly on all surfaces of the array by heating the silicon array in a furnace to a temperature high enough to cause oxidation. Oxygen and/or humidity levels in the furnace can be raised above the ambient to speed oxidation process (see, e.g., Atalla et al., *The Bell System Technical Journal*, pp. 749–783, May 1959). The silicon oxide layer is advantageous because it enables the application of various chemical surface treatments to the array surfaces. Examples of surface treatments are found in *Immobilized Affinity Ligand Techniques* (Hermanson et al, Academic Press, San Diego, 1992) and technical literature available from United Chemical Technologies, Inc., Bristol, Pa. Use of silicon oxide provides and additional advantage, allowing the optical reflectivity of the surfaces to be controlled by adjusting the thickness of the silicon oxide film (see, e.g., *Principles of Optics*, M. Born & E. Wolf, Pergamon Press, 1980, pages 59–66).

II. Methods of Modifying the Surfaces of Array Devices and Walls of Through-holes The surfaces of the through-hole arrays can be modified in various ways (e.g., to change their physical and chemical properties). Types of surface modification can include, but are not limited to, the application of polymer coatings, deposition of metals, chemical derivitization, and mechanical polishing.

Selectively Modifying the Surface Chemistry of Array Faces: In order to prevent aqueous solutions from adhering to array surfaces and cross-communication between the various through-holes during loading and other manipulations, it is desirable to coat the surfaces of the platen with a hydrophobic coating. It is also desirable to coat the inner surfaces of the through-holes with a hydrophilic coating so that they retain fluids. The inner coating can further be blocked, preventing non-specific binding, or derivatized with affinity ligands. This combination of hydrophobic surfaces and hydrophilic through-holes prevents aqueous solutions from adhering to the surfaces of the array while allowing instantaneous loading of the through-holes.

Generally, a platen having a dense array of through-holes is produced in silicon and coated in silicon oxide by oxidation. The platen is then cleaned, removing organic materials, by soaking in a mixture of hydrogen peroxide and sulfuric acid, or other caustic solvent cleaning solution. This treatment results in clean silicon oxide with a high surface energy. Hydrophobic coatings produced using this method are stable under high humidity and they can be used repeatedly.

The top and bottom faces of the arrays are made hydrophobic through exposure to vapor from a solution containing an appropriate silanizing agent (such as polydimethylsiloxane sold as Glassclad 216 by United Chemical Technologies, Inc.) in a volatile solvent. The silanizing agent reacts with the hydroxyl and silanol groups on the array surface and creates covalent bonds to hydrophobic alkyl groups. Selective modification of the surface chemistry can be achieved by selection of alternative silanizing agents.

In one surface modification method, a positive pressure of inert gas is applied to the surface of the platen opposite the surface being treated. The positive pressure within the through-holes prevents the silanizing vapor from reaching the interior through-holes. Silanizing agents suitable for rendering glassy surfaces hydrophobic include alkyltrichlorosilanes and alkyltrimethoxysilanes, many of which are commercially available.

In another method, a first platen is made from silicon, and then oxidized. A second silicon platen is produced with identical size and alignment holes, but without through-holes. The through-hole array platen is placed on top of the solid platen on the stacking jig such that each through-hole becomes a well. The jig and plates are then treated with a surface-modifying chemical reagent. The air trapped at the bottom of the wells prevents the fluid from entering the wells. After sufficient time for the reaction to occur, the plate is removed from solution, dried, and heat-treated if appropriate. The backing is removed, the array is flipped over, and the process repeated, coating the second surface.

Yet another method for creating hydrophobic exterior surfaces is to place the array on a matching array of pins such that each single pin narrowly passes through its corresponding through-hole. This array of pins can be the electrode used to create the array of through-holes using sink EDM. Next a coating of a hydrophobic polymer such as polypropylene or Teflon is deposited on the exposed surfaces using gas phase deposition method such as evaporative vapor deposition. The array of through-holes is removed from the matching pin array, inverted, and the coating process is repeated to cover the opposite surface.

Another method for producing hydrophobic coatings on the platen surfaces involves coating platen surfaces with a metal such as gold (then exposing the arrays to a chemical that selectively reacts with the metal, but not with the uncoated through-hole surfaces. For example electron beam vapor deposition can be used to coat the outer surfaces of a platen containing a plurality of through-holes with gold, other metal or semi-conductor. Electron beam vapor deposition will preferentially deposit the gold on surfaces normal to the beam direction. The gold-coated surface can then react with alkane thiols to attach a hydrophobic alkyl groups (Z. Hou et al., *Langmuir*, 14:3287–3297, 1998). The inner surfaces of the through-holes that are not coated with gold will remain hydrophilic. Alkane thiols are also reactive towards other materials including silver, copper and gallium arsenide (Y Xia and G. M. Whitesides, *Annu. Rev. Mater. Sci.*, 28: 153–84, 1998). Amphiphiles besides alkane thiols can be chemically reacted to other inorganic solid materials to produce hydrophobic coatings. Examples of such coatings include, but are not limited to, alkanephosphates on metal oxides (D. Brovelli et al., *Langmuir*, 15:4324–4327, 1999 and R. Hofer et al., *Langmuir*, 17: 4014–4020, 2001), and alkane carboxylates on alumina (P. E. Laibinis et al., *Science*, 245: 845, 1989).

Selectively Modifying the Surface Chemistry of Through-Hole Surfaces

In one method, multiple, identical through-hole arrays are prepared, aligned, and stacked. A chemical reagent is passed through the continuous channels formed by the stacked arrays. The reagent can be a solution, a suspension, a liquid, a vapor, or fine powder. The stack of arrays is then washed, dried, and heated, as appropriate for the particular coating. The stack of chips is then physically separated from one another and the arrays on the top and bottom of the stack ("sacrificial arrays") are discarded.

Another method for selectively coating through-hole surfaces involves using a robot to position a fine needle or an array of fine needles proximal to the entrance of each through-hole. Chemical surface-modifying reagents can then be delivered through this needle/capillary directly into individual holes In another method, all surfaces of a silicon through-hole array are chemically modified. The array faces are then mechanically polished to restore the original surface character. The array faces can then be coated again.

In still another method, the array faces are coated with a material that is inert towards the desired surface-modifying chemicals, and then the entire array is exposed to it. For example, a gold coating can be applied to both faces of an oxidized silicon through-hole array by electron beam deposition. The array can then be submerged in a solution of chemical reagent such as a silanizing reagent that reacts selectively with the siliceous through-hole surfaces.

In another method, the inner and outer surfaces of a through-hole array are coated by filling the holes with a removable, impermeable material. For example, the interior surfaces of the through-holes in an array can be protected by filling them with a solid that can later be removed. Examples of such a solid include a wax, a plastic, a frozen oil, ice, dry ice, or a polymer such as poly(ethylene-glycol). In one example, the through-holes are filled, excess material removed from the surface of the platen, and the surface coated, leaving the interiors uncoated. Methods for removing excess materials include scraping, sanding, polishing, dissolving with a solvent, melting or burning. The solid material in the interior of the through-holes can be removed under similar conditions. The interiors of the through-holes can then be selectively coated or modified.

Derivatizing Through-Hole Surfaces

In many cases it is desirable to immobilize probes on the inner walls of all, some, or one of the through-holes. There are many techniques for covalently attaching probes to glass or plastic surfaces (see, e.g., *Immobilized Affinity Ligand Techniques*, Hermanson et al., Academic Press, 1992). Those methods useful for glass can also be used for the oxidized surfaces of a silicon substrate. For example, the inner walls of the holes in an oxidized silicon through-hole array can be reacted with g-glycidoxypropyl trimethoxysilane in the presence of acid and heated to provide a glycerol coating. This glycerol coating can then be covalently linked to peptide or nucleic acid probes.

Rendering the Inner Walls Porous: The inner wall of a through-hole can be made porous by chemical etching following the procedure as outlined by Wei et al. (*Nature*, 399:243–246, 1999). The larger area of the porous region increases surface area and thus the amount of chemical reagent attached to the through-hole inner wall. When used for synthetic transformation, the increased reagent loading of porous through-holes increases yield. When used for detection, the increased reagent loading increases sensitivity. Furthermore, the material between adjacent through-holes can be made porous allowing for communication between through-holes by liquids or gases. This method can be useful for the controlled delivery of reagents stored in adjacent through-holes, allowing mixing of reagents and reactions to occur. All or part (e.g., just the middle portion) of the through-hole can be made porous.

Polymer Scaffolding for Protein and Cell Immobilization in a Platen

The interior walls of the through-holes of the platen can be derivatized to allow covalent or non-covalent attachment of proteins or cells. Any signal arising from the protein or cell thus attached is then confined to the perimeter of the well, unless the signal is enzymatically amplified, as in an ELISA assay. Even if amplified in this way, however, the signal may be weakened, for example, by low analyte concentration. In the case of cell attachment, because the wells are bottomless, cells can attach only to the interior walls and can grow upwards in two dimensions. An alternative to passive protein adsorption and covalent attachment to the walls of the array through-holes is the introduction of a three-dimensional hydrophilic scaffold such as a hydrophilic linear, gel or foam polymer filling activated for protein coupling or capable of protein or cell entrapment within the well.

Covalent Attachment of Proteins to Polymer-filled Through-holes of the Platen

Because the interior surface of the through-holes is hydrophilic, a hydrophilic or water soluble pre-polymer can easily be loaded into the wells of the platen and the polymerization reaction can be initiated by a change in temperature or pH or by the addition of initiator. Protein coupling can be carried out during polymerization, provided that the polymerization conditions do not affect protein structure and function. Alternatively, protein coupling can be carried out after polymerization. Proteins can be coupled using any of a variety of reactions, including reactions of free amines, free carboxylic acid groups, and free sulfide groups. Reactions that form isourea linkages, diazo linkages, or peptide bonds are among those typically used to couple proteins to surfaces, but any aqueous based polymer reaction that is easily controlled can be used. Examples of polymers scaffolds include dextran and polyamides.

Dextran is a polysaccharide polymer that is very hydrophilic. The sugar residues of dextran contain hydroxyl groups, which can be chemically activated for covalent bond formation. Hydroxyl groups also form hydrogen bonds with water molecules, and thereby create an aqueous environment in the support. When activated with an aldehyde, dextran can be easily coupled with proteins via amine groups (e.g., using sodium cyanoborohydride). When activated with hydrazide, dextran can be coupled with proteins via aldehyde or carboxyl groups using 1-ethyl-3-(3-dimethylaminopropyl carbodiimide hydrochloride) (EDC). However, use of dextran for certain applications is limited by its susceptibility to microbial attack.

An alternative method for covalent immobilization of proteins or enzymes is through various derivatized polyamides, such as Nylon®. Polyamides are best suited for the immobilization of high molecular weight substrates. Chemically, many polyamides are thermoplastic polymers with high mechanical strength, superficial hardness, and resistance to abrasive conditions caused by the intermolecular hydrogen bond interactions established between the amide groups of parallel chains. These characteristics make polyamides useful for immobilized enzymes, because they provide a favorable hydrophilic microenvironment to support both catalytic activity and enzyme structure. Proteins covalently attached to a polymer scaffold are amenable to conventional biochemical assays such as ELISAs, binding assays, and activity assays.

Encapsulation of Proteins (or Cells)

Both proteins and cells can be immobilized by encapsulation within a web, matrix, or pores of semipermeable membranes, gels, or foams. Encapsulation of cells requires special consideration of the following factors: diffusion of materials within and through the support; non-toxicity of the starting materials and of the polymer to cells; and physical properties such as optical clarity, temperature stability, flexibility, and resistance to chemical and microbial attack. The support is preferably resilient and flexible, capable of hydrogen bonding, and resistant to proteolysis and hydrolysis.

Given an appropriate scaffold, mammalian cells can be cultured in three dimensions in a platen through-hole, enabling both the performance of many types of cell-based assays and the potential for imaging of cells within the through-hole using confocal techniques. Examples of types of assays that can be carried out include reporter gene assays, cell growth assays, apoptosis assays, and assays involving events occurring at the cell surface or within the cytoplasmic region (e.g., measurements of calcium efflux from the endoplasmic reticulum). Such assays are useful for functional studies of chemical and biological libraries. Examples of materials amenable to encapsulation include Poly-(2-hydroxyethyl methacrylate) (poly-HEMA) gel, Poly (carbamoyl sulfonate) (PCS) hydrogels, and Phosphorylated polyvinyl alcohol (PVA) gel.

Poly-(2-hydroxyethyl methacrylate), "poly-HEMA," gel has superior mechanical properties, temperature tolerance, and resistance to microbial attack than many natural polymers (e.g., gelatin, agarose, carrageenan, cellulose, and albumin). Poly-HEMA gels can be used for entrapment of both proteins and cells. The process of biocatalyst immobilization in poly-HEMA hydrogels generally allows for high retention of immobilized enzyme activity, well-controlled porosity (e.g., to ensure sufficient mass transfer of reactants and products), and good chemical resistance. Poly-HEMA hydrogels also protect entrapped proteins and cells from bacterial degradation, by resisting bacteria entry into the gel support. Additionally, Poly-HEMA hydrogels can retain a large quantity of water, providing a microenvironment that approximates in vivo conditions.

Poly(carbamoyl sulfonate), "(PCS) hydrogels," afford adjustable gelation time, high mechanical stability, and resistance to microbial attack. PCS hydrogels also have a high degree of flexibility, which can be exploited for filtering or expelling samples.

Phosphorylated polyvinyl alcohol, "phosphorylated PVA" gels can be used to immobilize cells of bacteria or yeast. These gels are economical, nontoxic, durable and support a high cell viability. Applications using phophorylated PVA gels are limited by their poor gas permeability.

Fiberglass Chip

A through-hole array having holes filled with fibers can be created in a simple and inexpensive manner. Examples of useful fibers include fiberglass filters, mesh glass fiber filters, and polymer filters such as Nylon® and polyethersulfone. These materials can be surface modified for specific interactions prior to fusing.

In one method, a sheet of loose fiberglass mesh is fused between through-holes of an array. The fusion can be achieved by pressing the fiberglass against a through-hole array created from silicon or other suitable metal that has been heated to a temperature sufficient to fuse the fiberglass, and then removing the array. Non-reactive lubricants such as graphite or molybdenum grease can be used to aid in the separation of the heated array and fiberglass arrays. Alternately, the fiberglass sheet can be pressed between two, aligned, heated through-hole arrays.

The resulting fiberglass array can be treated to make the regions between the porous holes hydrophobic. Such treatment can be accomplished by blowing gas through the array while exposing the opposing face to a silanizing vapor. The porous areas in the resulting fiberglass array can be used for immobilizing probes such as nucleic acids or peptides with the advantage of very high surface areas for attachment, ease of flow through the array and the optical transparency of glass.

An alternate method for producing the fiberglass arrays is to inject or cause a polymerization of a thermoplastic material in the space between the desired holes, for example, by using a printing technique to deposit a polymer, epoxy, monomer, or polymerization initiator, or by photo-initiating polymerization or curing in the desired areas using one or more photomasks.

Growing Porous Glass in the Through-holes

Another method for producing an array of through-holes containing a porous material is to machine an array by an appropriate method such as EDM and then to grow material in the array. Porous glass can be introduced into the array by using pressure to force a mixture of potassium silicate mixed with formamide into the array and then baking for several hours. An array of capillaries that is fused or embedded in a binding agent can be filled with porous glass by this method and then sectioned with a cooled sectioning saw to create multiple, thin platens of porous-glass filled through-hole arrays. By including particles such as porous silica or polymer beads in the potassium silicate mix, the affinity properties and porosity of the material can be adjusted as desired.

III. Methods of Loading Array Devices with Samples

Synthesis of an Array by Masking

Certain methods feature applying at least one mask to a platen, or an aligned stack of such platens, such that, when a reagent is applied to the mask, the reagent communicates with only the through-holes selected by the mask. In particular embodiments, the reagent can be selected from an aqueous solution, an organic solution, a dry powder, a gel, a gas, or an electromagnetic radiation (e.g., heat, light, X-rays, ultraviolet radiation, a magnetic field). Methods for introducing reagents through the mask and into the array include applying a mechanical or optical pressure to the reagent reservoir, diffusion, and electrophoresis. Measures to prevent cross-contamination of neighboring wells include placing a second, identical mask on the face of the platen opposite the face to which the reagent is applied, and using a blotter to absorb excess liquid flowing through the through-holes. The masks and arrays can be held together by electrostatic, magnetic, or gravitational forces, or by applied pressure (e.g., by applying a clamp to the periphery of the stacked platens). Masks and arrays can be separated when liquid fills the through-holes by application of electrostatic, magnetic, or gravitational forces, or by application of a negative pressure to the stacked platens. Stacks of platens can optionally be dried to facilitate separation.

The liquid samples in the through-holes can be subdivided by placing an empty array beneath a filled array or array stack, and then applying positive or negative pressure to force a portion of the liquid into the empty array. A small (typically less than 100 $\mu$m) air gap is maintained between the filled array and the empty array to facilitate the physical separation of the two arrays after the fluid transfer is complete.

Through repetitive cycles of adding masks, introducing reagents, and optionally washing the array, a defined pattern of chemicals can be created in the through-holes of the platen by using solution phase chemistry.

Figure 2:
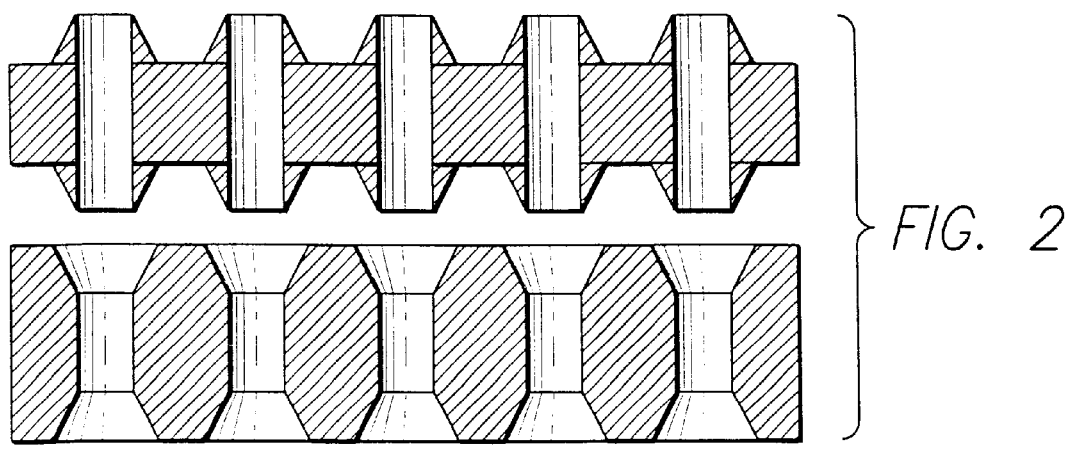
FIG. 2 is a cross-sectional view of an interlocking array system.

By first derivatizing the inner surfaces of the through-holes with a linker molecule that contains a free functional group, the inner surface of each hole can be coated with a member of a library of molecules. The patterned through-hole array is then used to analyze chemical information. As described above for solution phase systems, repeatedly adding masks, introducing reagents, and washing the array, can result in a defined pattern of chemicals attached to the linker molecules in the through-holes. FIG. 1 is an illustration of this process. A platen (1) having through-holes with derivatized inner surfaces (4) is brought into contact with a mask (2) configured such that only select through-holes in the platen communicate with the reagents to which the masked platen is exposed. In this embodiment, two identical masks (2,3) are placed in contact with the top and bottom surfaces of the platen so as to prevent fluid from entering the covered through-holes. Preferably, the masks and platen are flat and polished (e.g., to an optical finish) so that they create an airtight seal when contacted. Alternatively, the mask or platen, or both, can be coated with a soft polymer or gasket-forming material to facilitate sealing, or the mask and platen surfaces can be manufactured with contoured surfaces such that one fits into the other to form a large contacting surface area. The contoured surfaces can also provide alignment features that can aid in co-alignment of through-holes in the masks and platens. One example of an interlocking array design is shown in cross-section in FIG. 2, where the through-hole arrays are contoured to have opposing and matching geometrical features. The requisite geometrical features can be obtained, for example, by patterned chemical etching or micromilling.

Similar approaches can be applied to the manufacture of a system having two masks with a platen sandwiched in between. The mask-platen sandwich can then be loaded with a reagent, such that the reagent enters into the open (i.e., non-masked) through-holes. After the reagent has reacted with the linker molecules located inside the through-holes, the excess reagent can be washed from the sandwich, and the process can be repeated with a new reagent. The mask can then be removed and a new mask applied, or the synthesized material can be removed from each through-hole.

Another embodiment uses only one mask to block one end of the through-hole with an airtight seal. The air trapped in the through-hole prevents liquid from entering into the through-hole.

In another embodiment, a porous material derivatized with a linker molecule having a free functional group is in each through-hole and members of a library of chemical probes are attached to the linker molecules. Alternatively, the inner surfaces of the through-holes are made porous (e.g., by etching with hydrofluoric acid), and the library of probes is attached. Containment of probes within the porous polymer or surface (i.e., as opposed to immobilization of library members on the inner surface of the through-hole) increases the density of library molecules in each through-hole.

For chemical synthesis, a porous polymer derivatized with a linker molecule having a free functional group can be inserted into the through-hole. By repeatedly adding masks, introducing reagents, and, optionally, washing the array, a defined pattern of chemicals attached to the linker molecules can be created in the through-holes. Containment of linker molecules within the porous polymer increases the density of synthesized molecules in each through-hole.

A similar synthetic procedure can be used with a molecular library immobilized inside a porous through-hole surface.

Mask Production Methods

An embodiment of the invention provides for producing a mask by use of a through-hole array substantially identical to the array used for synthesis or analysis. In one embodiment, a mask can be fabricated from metal, dielectric (glass, polymer) or semiconductor (e.g., silicon, germanium, gallium arsenide). Inertial drilling is a suitable manufacturing process for fabrication of masks in polymers, glass or metals. Patterned chemical etching processes, such as deep reactive ion etching (DRIE), provide another suitable manufacturing process for fabrication of masks in semiconductors and dielectrics such as glass. Electrospark discharge machining (EDM) is another suitable manufacturing process for fabrication of masks in conductive materials (e.g. conductive semiconductors and metals).

Another embodiment of the invention, shown in FIG. 4, provides for producing a mask by use of a through-hole array substantially identical to the array used for synthesis or analysis. A solution (1) is added to each hole of a through-hole array (2) such that the solution contains a molecule or mixture of molecules that polymerize upon irradiation (Step 1). The solution could be for example, an aqueous solution of polymer and a photo-reactive molecule that produces free-radical initiators of polymerization when irradiated with ultraviolet light (3) (Step 2). An example of a UV curable polymer suitable for mask fabrication can be found in the class of UV-curable polyurethane epoxies. By shining ultraviolet light onto each hole that the artisan wishes to be blocked in a given step of adding reagent to a through-hole array, a mask (4) is built (Step 3). The resulting polymer is impervious to the fluids to which the mask is exposed. The through-holes to be blocked can be illuminated through an optically opaque mask or illuminated sequentially with focused light.

Another embodiment, shown in FIG. 5, uses an array of pins or posts to make a mask. The external dimensions of the static pin array are selected such that they have a precision fit into a matching through-hole. Viewed in cross-section, a pre-fabricated pin array (1) selectively blocks those through-holes from communicating with a reagent as part of a synthesis sequence. A through-hole array (2) is prepared with the inside surface of the through-hole derivatized with a linker molecule having a free functional group (Step 1). A pin array is inserted into the through-hole array (Step 2) and by the process of introducing reagent and optionally washing the array, a defined pattern of chemicals in the open through-holes is created attached to the linker molecules (Step 3). The pin array mask is removed and the process is repeated with a different mask and reagents resulting in a defined pattern of chemicals created in the through-hole array (3) attached to the linker molecules (Step 4).

Pins in the array are fabricated to precisely fit into each matching through-hole forming a hermetic seal. Polymer coatings (e.g., Teflon) can be applied to each pin to facilitate sealing. An advantage of this approach is that the post arrays are reusable and need only to be made once. The large contact area between the pin and through-hole interior surface ensures a viable hermetic seal. As opposed to the plate masks, only the pins contact the array plate, thereby facilitating decoupling of the mask from the array plate after completion of a synthesis cycle. A further advantage is gained by application of only one pin array to seal through-holes in an array. This is achieved by physical blockage of the hole by the inserted pin or by the pressure of air entrapped in the through-hole. The pin array can be manufactured by a variety of fabrication techniques. One example is to electro-spark discharge machine (EDM) a regular array of pins having the precision cross sections needed to hermetically seal a through-hole. With a die-sinking EDM, selected posts could be machined away with a die to form the spatial pattern of pins matching a particular mask configuration. A second example is to start with a plate having holes in the spatial pattern matching a mask configuration. The pins are fitted into each through-hole and simultaneously soldered in place.

Another embodiment uses an actuated pin array forming a mask to hermetically seal selected through-holes in an array. The actuated pin array is similar in design to the static pin array except that each pin can be extended or retracted such as to reconfigure the pin array to make a different mask. This is different from the static pin array in that each different mask requires a different pin array. Extended pins are inserted into through-holes whilst retracted pins are not. Individual pins in the array are electronically addressable to be actuated by one of several types of methods including: piezoelectric, electromagnetic (solenoid), magnetostrictive, shape memory alloy or conducting polymer. One advantage of this approach is a single pin array can be reconfigured to produce $n!/(n-2)!$ number of different masks where n is the number of pins in the array. A second advantage is generation of different masks in an automated manner. This is important when the processes requiring masking of the through-hole array are also automated.

In still another embodiment, the mask has holes that allow reagents to flow to selected positions in the through-hole plate. In other positions, the mask includes raised features (e.g., pins or bumps) that fit into the holes to be blocked. This approach aids in alignment of the mask and platen, allows a single mask to be used, and ensures a good seal between the mask and the platen.

The through-hole array can also be fabricated with valves on one side of the through-hole array. Each through-hole thus has a valve that either blocks or unblocks one end of the through-hole. Pressure of air entrapped in the through-hole prevents liquid from entering the open end of the blocked through-hole. The valve can be formed as a bilayer actuated by shape memory alloy, electrostrictive, electroporous, piezoelectric, magnetostrictive, or conducting polymer materials. Microsolenoid activated valves can also be used to perform a similar function.

Another method for producing a flow-mask is to laminate a platen on at least one side with a non-permeable membrane such as an adhesive tape. The mask is then created by selectively perforating the laminate material. Methods by which the laminate can be perforated are: by an actuated pin array, by laser machining, by contacting with a platen that allow heat to be applied in a localized manner, thus melting or burning a hole in the laminate. Serial dilutions can be performed during loading.

This operation can be performed to fill a series of through-holes with different concentrations of the same solute. In a typical example, a microsyringe, or other fluid transfer device, is positioned over the first through-hole and used to fill the first and second through-holes with a 16X solution of the solute. The outer surface of the syringe tip and the faces of the array must be nonwetting toward the solution being dispensed. For each hole, a sufficient volume of solution, referred to below as "Y nl," is dispensed to overfill the hole enough to create positive menisci. The microsyringe tip is then rinsed three times and filled with solvent. The syringe tip is positioned above the second through-hole and Y nl of solvent is expelled such that it forms a droplet at the end of the syringe tip. The syringe tip is lowered until the solvent droplet contacts the solution surface, causing the two liquids to mix and produce an 8X solution. The syringe plunger is then withdrawn to suck up Y nl of 8X solution and dispense it into the next through-hole. Another droplet of solvent is then formed and the process can be repeated to dispense 4X, 2X, 1X, etc. into individual array through-holes.

Serial Array of Masks on a Flexible Sheet

Since synthesis of an array of probes in through-holes can involve the use of many masks, a rapid and automated method for interchanging masks is desirable. One method involves creating the multiple masks in a single, flexible tape, such as a metal or plastic tape with a width greater than that of the array to be synthesized. The first mask can be aligned with the array and reagents can be transferred to the array. The tape can then be advanced to reveal the next mask prior to addition of the second reagent. This process can be repeated until the solid-phase synthesis is complete. For steps that require washing the entire array, a single large hole, or holes corresponding to each position in the array, can be produced on the tape. For additional through-put and customization of the synthesis, the tape can be produced concurrently with the synthesis, for example, by having an array of punches or a micro-positioned laser drilling system to create holes as the tape advances. A second tape or blotter can be used on the opposite side of the array (e.g., to prevent cross-talk). Various methods for aligning the masks with the arrays can be used, including placing precise alignment notches in the tape, and using optical or amperometric detection to determine mask position relative to the array.

Synthesis of Arrays Using Masks and a Membrane

The mask-synthesis methods described here can also be used with non-addressable porous membranes (e.g., a filter), instead of with the rigid platen.

Capillary Tube Array

Viewed in cross-section, a capillary tube array (FIG. 6) is constructed from capillary tubing (1) with an external diameter that fits precisely into the through-holes of a second array. The tubing array (3) is designed such that tubing at one end has a center-to-center spacing equal to the spacing between holes in a through-hole array and tubing at the opposite end has a center-to-center spacing equal to the center-to-center spacing of wells in a microtiter plate (2). Plates with through-holes having these separations serve as jigs (4) to hold the tubing in a regular array. Additional through-hole plates placed between the two ends are spacer jigs providing additional support for the tubing array as the center-to-center spacing is changed over the tubing length.

The internal volume of each tube in the array is slightly greater than the total volume of a column of aligned holes in the array stack. For example, if the through-hole dimensions in the array are 250 $\mu$m×250 $\mu$m×1000 $\mu$m giving a volume per through-hole equal to 62.5 nl, then the volume of one set of holes in a stack of 100 arrays is 6.25 $\mu$l (100×62.5 nl). Capillary tubing with an internal diameter of 200 $\mu$m and an external diameter of 245 $\mu$m is readily available; thus a minimum tube length of 200 mm stores the volume of fluid needed to fill this set of through-holes.

Figure 6:
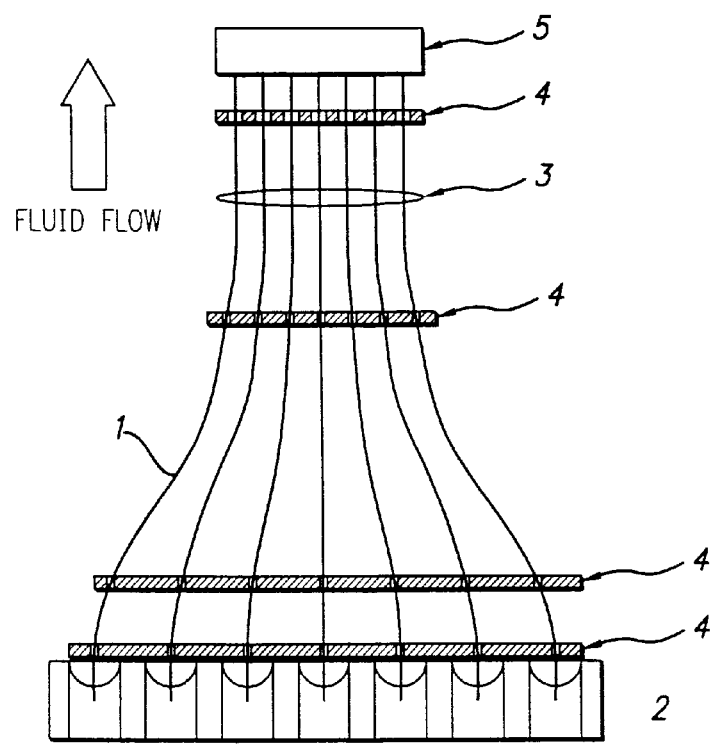
FIG. 6 is an illustration of a method for storing liquid from individual wells from a microtiter plate in a bundle of capillary tubing for transference into high-density through-hole arrays.

One end of the tubing array is inserted into the wells of a microtiter plate where each tube is inserted into a matching well. A negative pressure is applied across the length of tubing, drawing liquid from each well into its corresponding tube. Negative pressure can be applied to each tube individually or as shown in FIG. 6, the ends of the tube array can terminate in a chamber (5) that can be partially evacuated. After filling each tube of the array, the microtiter plate is removed. The liquid can be stored in the tubing array for an indefinite period of time, either frozen or in a humidified environment. Multiple tubing arrays can be filled from the same microtiter plate (assuming there is sufficient volume of liquid per well) or different tubing arrays can be filled from different microtiter plates.

Transfer from a Microtiter Plate with an Array of Flexible Members

Figure 7:
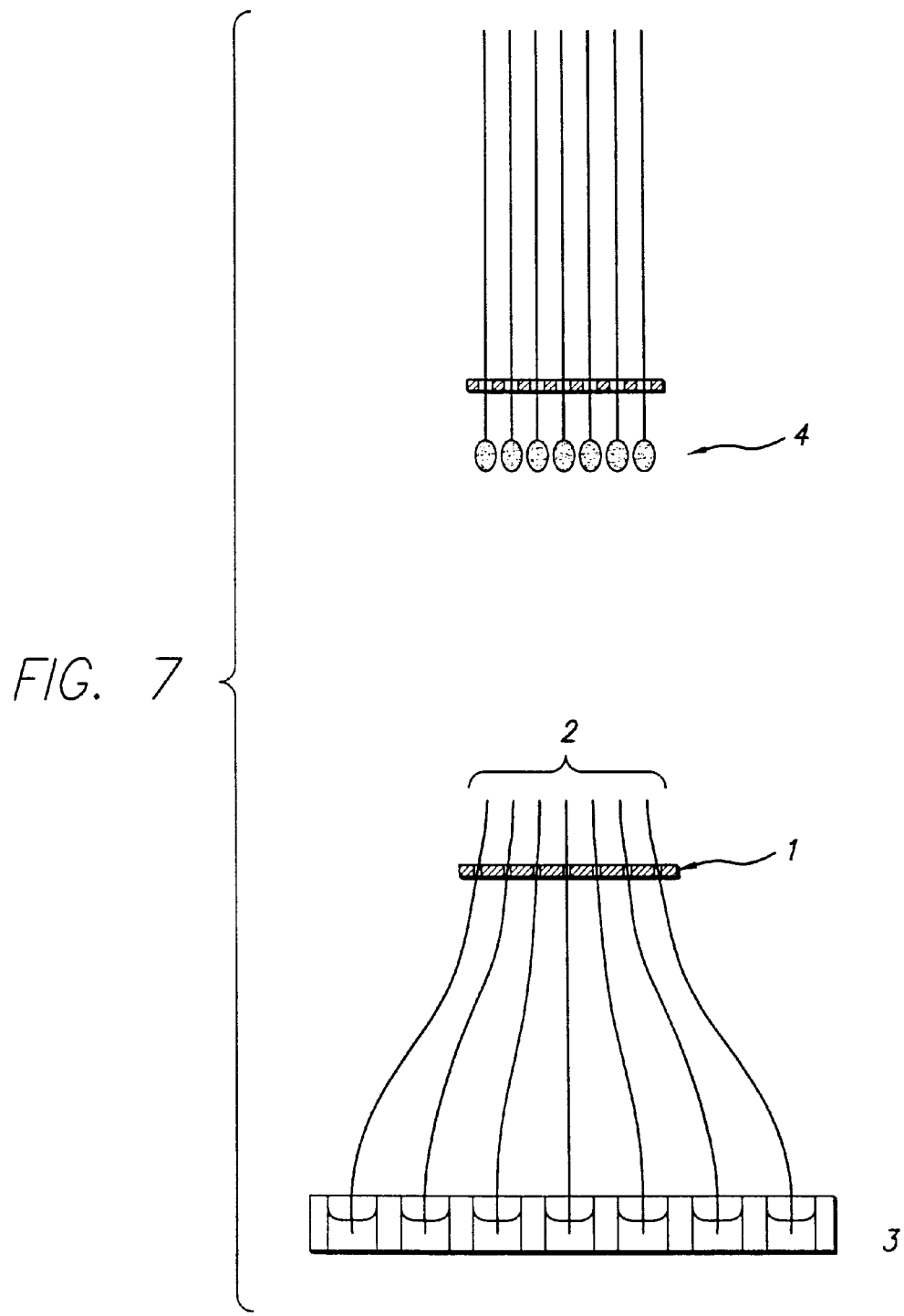
FIG. 7 is an illustration of a method for transferring fluid from wells in a microtiter plate to through-holes in an array using a flexible member.

As illustrated in FIG. 7, fluid can be transferred from individual wells of a microtiter plate (3) with an array of flexible members (2) (e.g., shape memory alloy fibers). The fiber diameter is equal to or less than the inside dimension of the through-holes in the array (1) into which fluid will be transferred. The number of fibers in the bundle can, for example, be equal to the number of wells in the microtiter plate. The ends of the fibers at one end of the bundle can have a center-to-center spacing equal to the spacing of the holes in the through-hole array, while the ends of the fibers at the opposite end can have a center-to-center spacing equal to the spacing of wells in the microtiter plate. The fibers can be held in place with a series of through-hole jigs designed to increase the spacing between fibers from one end of the bundle to another. Once fixed in place, shape memory alloy fibers can be heated above their critical transition temperature to make the imposed fiber curvature permanent. After they are cooled to room temperature, the fibers can be removed from the holding jig, with the change in fiber center-to-center spacing intact. The close packed end of the fiber bundle can then be inserted into the through-hole array into which fluid from each well in the plate is to be placed. The opposite end can be arranged such that each fiber is positioned above a well in the microtiter plate, and the ends of the fibers can be immersed in the fluid contained in each well. On retraction, a small volume drop (4) can remain attached (e.g., by surface tension) to the end of each fiber. A force can be applied to the opposite end of the fiber bundle to pull the bundle through the holes of the through-hole array, such that the fluid is brought into contact with the corresponding through-holes. As the fibers are pulled through the hole, surface tension can act to hold the liquid in the through-hole as the fiber is removed.

Pressure Loading

The array can also be loaded by applying a pressure across the platen, thereby causing a dilute solution of reagent and/or sample to flow through the array of through-holes. This method can be advantageous if the through-holes are already loaded with reagents, and a reaction with a second set of reagents is desired.

Bead Loading

Figure 8:
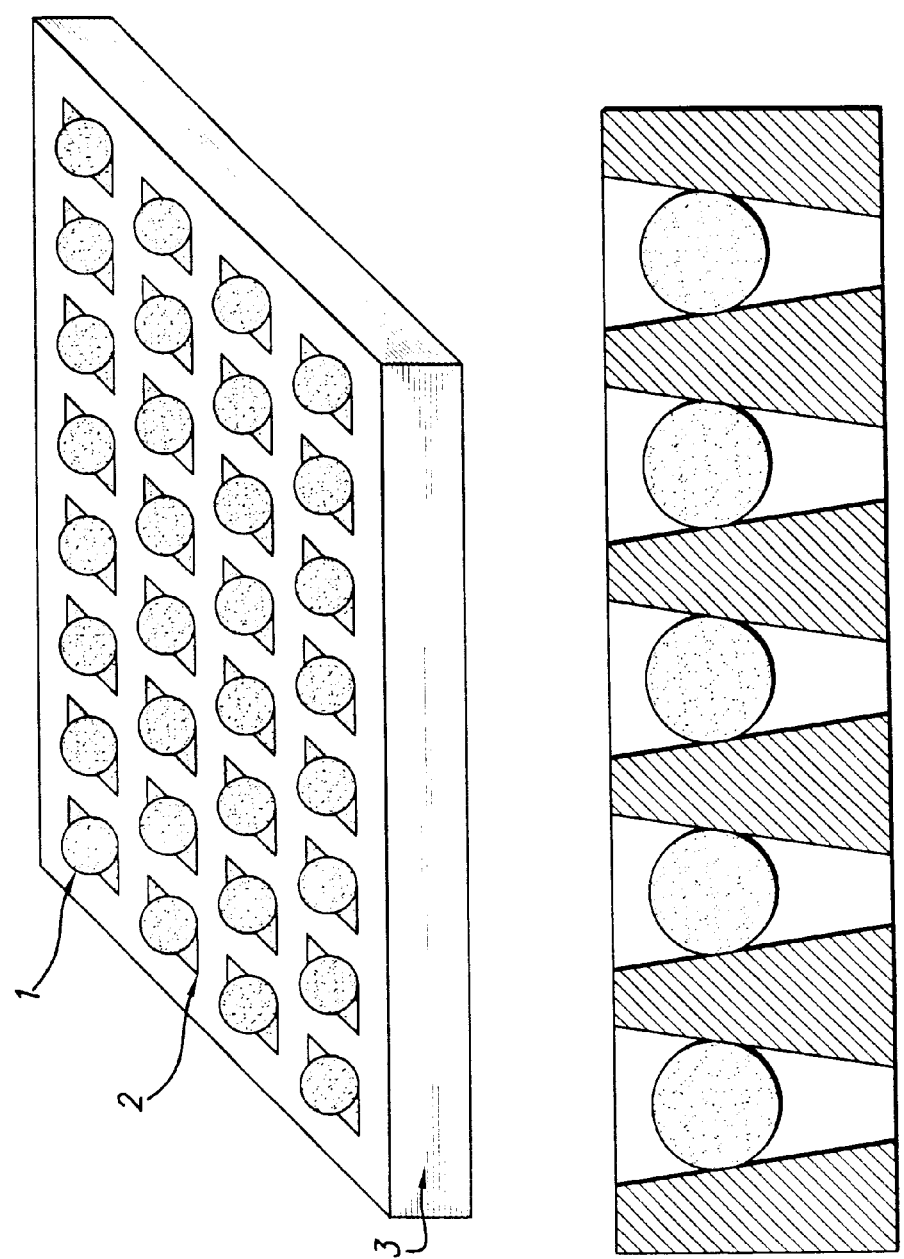
FIG. 8 is a drawing of an array in which the through-hole cross-sections are shaped to hold only one microsphere per through-hole, and the longitudinal cross-section is tapered such that the microsphere sits in the hole either at or below the array surface.

Bead loading can be used to load an entire combinatorial library immobilized on microscopic polymer spheres of uniform size (1). In this method, the through-holes (2) in an array (3) can be shaped so as to hold only one microsphere per through-hole. The through-holes can additionally have a tapered cross-section, such that the microspheres sits in the holes either at or below the array surface (FIG. 8).

Transferring Contents from a Second Array

Replicating a platen containing through-holes reproduce an array wherein each channel contains a colony of cells having a unique genetic profile. The master plate is prepared from a suspension of cells of diverse genetic characters. The suspension can be diluted such that when an array is loaded from the dilute solution, an average of one cell is transferred into each channel. The array is then incubated in an enclosed humidity chamber with the appropriate temperature and agitation for the cell type until the cells have reached mid log phase. The cell number density can be estimated by observing select channels under an optical microscope, measuring the amount of scattering when light is incident on the arrays, or if the cells also contain a gene for green fluorescence protein production, by measuring the intensity of fluorescence from each channel. Various methods can be used to transfer a portion of the cells from each channel into corresponding channels in a second array.

One method of transfer involves freeze-drying the contents of the through-holes. A master through-hole array is prepared from a suspension of cells of diverse genetic characters as described above. A second identical through-hole array is filled with growth media. The two through-hole arrays are aligned and stacked to mix contents of corresponding through-holes. The stacked through-hole arrays are freeze-dried and separated. The colonies are reconstituted by filling the array with media. In the case of robust cells such as bacteria and yeast cells, dehydration by evaporation can be sufficient to remove the liquid without significantly compromising cell viability. This method is also useful for storing compound libraries such as small molecule libraries in a dry form. For example, the crystalline compounds can adhere to the walls of the channels. Compounds can then be stored for long periods of time and reconstituted by the addition of solvent. Compound libraries can also be stored in a powdered or crystalline form while frozen in an inert matrix. A suspension of crystalline compounds can be made in a low molecular weight perfluorinated hydrocarbon and stored frozen. An example of a perfluorinated hydrocarbon that can be used for this purpose is perfluorohexane, which has a melting point of −4° C. and a boiling point of about 59° C. Upon retrieval of the sample, the hydrocarbon can readily evaporate at atmospheric pressure or under an applied vacuum; the samples can then be reconstituted with DMSO, water, or other solvent.

Transfering/Mixing Samples in a Through-Hole Array with Samples on a Flat Surface Liquid samples contained in a through-hole array can be transferred in part or in whole to a flat surface having a pattern of hydrophilic and hydrophobic regions. The hydrophilic regions must be spatially isolated from one another and must match the spacing of the through-holes such that when the array is contacted with the surface, the contents of each through-hole contacts at most one hydrophilic region. The hydrophobic regions on the surface also serve to isolate the transferred fluids from one another.

The surface may support an array of samples that can be registered with an array of probes contained in a through-hole array. The samples must be spatially isolated from one another and must match the spacing of the through-holes such that when the array is contacted with this surface, the contents of each through-hole contacts at most one sample. The surface can also contain a hydrophobic pattern matching the pattern of the through-hole array to prevent cross-contamination after the surface and array are contacted. If a hydrophobic pattern is not provided, the platen and surface can be pressed tightly against one another to form a hermetic seal and thus prevent mixing between adjacent samples.

Alternatively the flat surface can support an array of probes, such as fluorescently labeled oligonucleotides, chemical substrates, or cells, matched to a through-hole array containing samples. The probes can be attached to the surface in a variety of methods: they can be chemically or physically absorbed on the surface, trapped in a porous matrix, attached with an adhesion layer, or contained in a drop of liquid. The probes can be used to generate a change in a detectable physical property of the sample (such as fluorescence, optical absorption or mass) in response to a chemical or biological characteristic of the sample as binding activity or enzyme activity.

Plunger Sterilization

Plunger sterilization can be an important aspect of a serial sampling scheme. One approach is to have at least two plungers-while one plunger is sampling, the other is being sterilized. The two plungers can be located in a common mechanical housing, for example, mounted to rotate about an axis parallel to the plunger axis. Plunger sterilization can be accomplished by heat or exposure to sterilizing agent (e.g., 70% ethanol). A wire (e.g., platinum) loop inside a ceramic sheath is an example of a suitable plunger design. The ceramic sheath imparts mechanical rigidity and is an electrical insulator whereas the wire loop permits heating with an electrical current. As an example, assume that a platinum wire loop is used, having a specific heat of 4 J/kg−° C. To electrically heat a $10^{-4}$ kg wire to 1000° C. in 0.2 s requires a maximum current of 4.5 A, which is easily achieved with medium power thyristors. Rapid cooling can be achieved from the spray of a volatile sterilizing agent (e.g., ethanol), the high latent heat of vaporization of which can aid in cooling the heated wire. Alternatively, the wire can be rapidly cooled by a spray of gas or liquefied gas such as liquid nitrogen.

Sequential sampling with a single sampling device can be extended to a linear array of sampling devices as, for example, a linear array of mechanical plungers. There can be a substantial time saving (e.g., 1/M for an M×M array of through-holes), since motion along one orthogonal direction can be avoided. Similar time saving considerations are applied to two-dimensional sampling techniques. In an alternate approach, pressure generated by spatially localized jets of liquid, solid, or gas can be used in place of the plungers.

Loading with High Protein/Surfactant Media

Loading the platen by submerging the platen into a reagent of interest when the reagent or media is high in protein or surfactant and therefore low in surface tension, can be a challenge. Droplets of the low surface tension fluid can remain on the surface of the platen after removal from the fluid to be loaded. If droplets or a surface coating of protein rich media remains on the surface, it can result in contamination of the assay or crosstalk between through-holes. This problem is significantly lessened by pulling the platen up through a layer of a hydrophobic fluid that is immiscible with the fluid to be loaded. This provides a wiping or "liquid squeegee" effect, removing the proteins or surfactants adhering to the surface of the platen. The wiping fluid setup can be generated one of at least three methods.

Submerging the platen in the fluid to be loaded, ensuring the through-holes are filled. The platen is withdrawn from the fluid to be loaded, and submerged in a hydrophobic fluid that has a greater affinity for the proteins or surfactants than the protein or surfactant has for the surface of the platen. Such fluids can include but are not limited to perfluorodecalin, silicone oil and mineral oil.

Alternatively, the platen is first submerged into the fluid to be loaded. Then a small amount of a less dense, hydrophobic fluid such as but not limited to mineral oil and silicone oil is gently layered on the surface so that the surface of the loading fluid is completely covered with this wiping fluid. Then the platen is slowly removed from the loading fluid, up through the wiping fluid.

Figure 23:
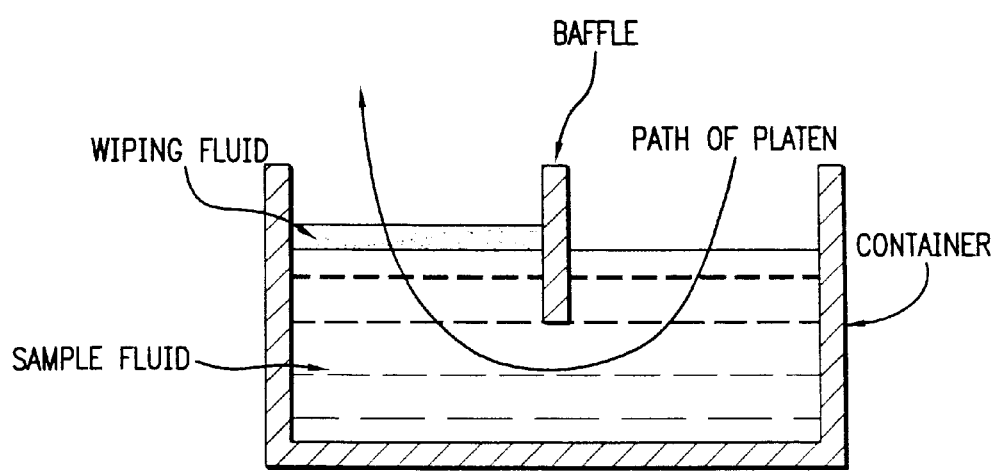
FIG. 23 depicts a method for wiping excess fluids from the surface of the platen. The device has enables a through-hole array to be loaded with sample and removed through a wiping fluid in an efficient manner.

Additionally, a container can be used as in FIG. 23. The container has a baffle that extends from one side if the container to another, but does not extend to the bottom of the container. The container is filled to a level midway up the baffle with the fluid to be loaded. This creates two open surfaces of loading fluid connected by a channel underneath. Wiping fluid is gently layered on one of the surfaces, and is kept from the other surface by the baffle. The platen is submerged into the fluid to be loaded, underneath the baffle, and removed through the wiping fluid. This method for employing the wiping fluid is well suited for high throughput and automation methods.

Synthesis of Arrays by Selective Loading of Fluids into Through-holes

Figure 3:
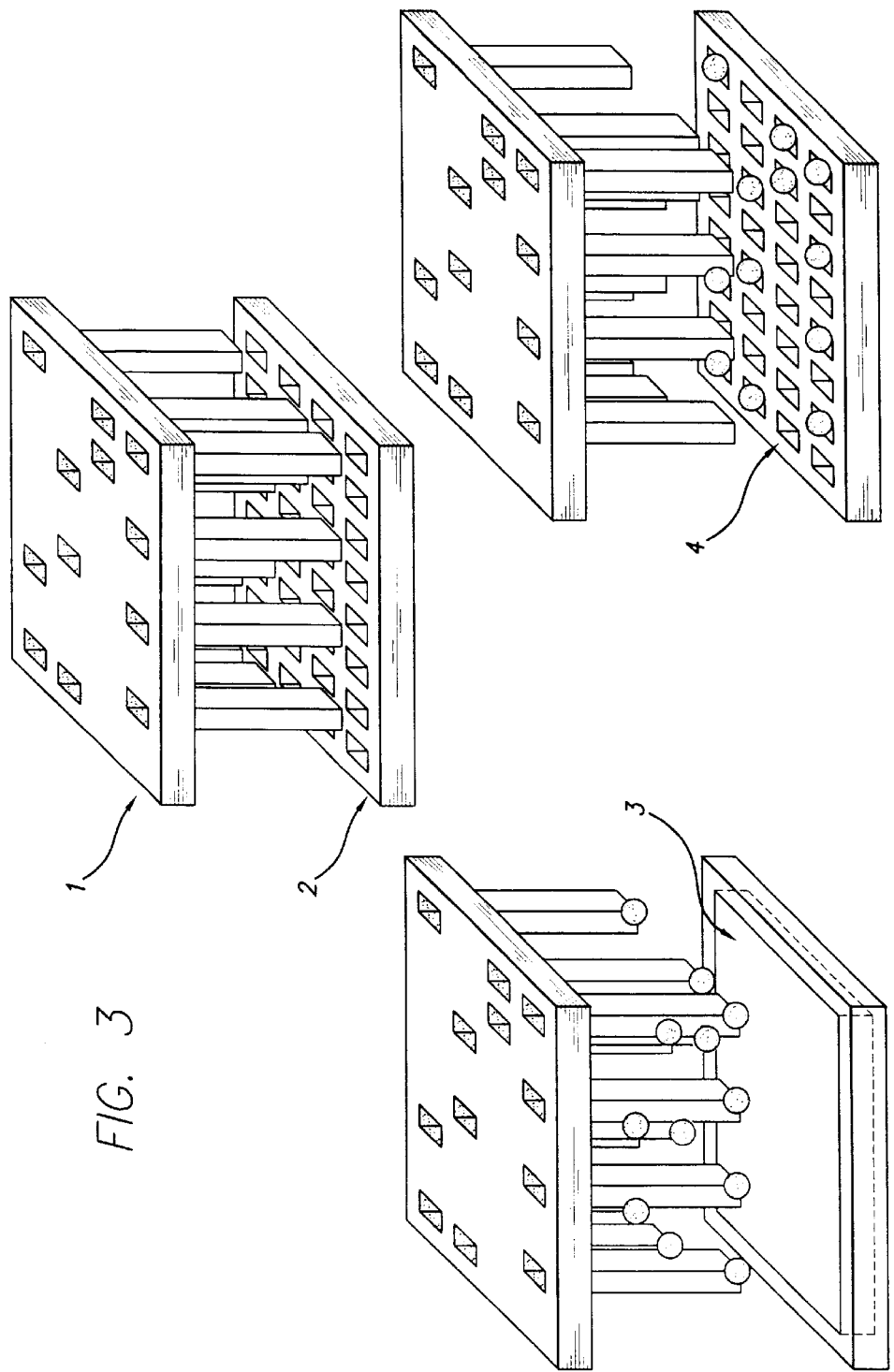
FIG. 3 is an illustration of a method for transferring small volume drops into specific through-holes in an array with a pin array.

An array of pins (1) can be fabricated with pins arranged to be co-registered and coaligned with a second regular array of through-holes (2) (FIG. 3). Each through-hole can be prepared such that linker molecules suitable for chemical synthesis are immobilized on the interior surface of each through-hole. The ends or tips of the pins can be made hydrophilic over a pre-determined surface area whilst the remainder of the array surface area is made hydrophobic. In one embodiment, the tips of the pins in the pin array are brought into contact with the fluid to be loaded into the through-holes of the through-hole array (3). When retracted, a small volume liquid drop adheres to the hydrophilic region of each pin (e.g., by virtue of surface tension). The volume of liquid adhering to the pin is determined by the relative surface energies between the liquid and solid surface and the depth of immersion of the pin into the liquid relative to the hydrophobic surface area. The pin array with the adherent liquid drops can be arranged relative to the through-hole array such that the through-holes into which liquid is to be placed are aligned relative to each pin with an adherent liquid drop. The two arrays can be brought into contact such that the drops enter into the corresponding through-holes (e.g., by capillary pressure). Removal of the pin array leaves behind the fluid placed into the through-holes of the array (4). A chemical reaction can thus be initiated between the linker molecules immobilized on the interior surface of the through-hole and the liquid placed in the through-hole. The chemical reaction rate can be increased by raising temperature and/or changing the partial pressure and/or composition of gas in the atmosphere surround the through-hole array. After the reaction is complete, the array can be washed to remove unreacted components, and dried to remove excess solvent. A second pin array with either the same or different pin configuration can be loaded with fluid and the synthesis process can be repeated. Because the array loading process can rely on simple mechanical motions, the array loading can be quite rapid. The rate-limiting step, therefore, would be the synthesis step itself.

An alternative embodiment features the use of a pin array sparsely populated with pins aligned with respect to the through-holes of a regular array. The pins can be fabricated such that their length is at least twice the thickness of the through-hole array platen. Each through-hole can be prepared such that linker molecules suitable for chemical synthesis can be immobilized onto the interior surface of each through-hole. The end of each pin can, for example, by made hydrophilic and the remainder of the array can be made hydrophobic. The lateral dimension of the pins can be set such that the pins can be inserted into the matching through-holes in a regular array. The pin array can then be inserted through the second through-hole array such that the pins extend through to the opposite side of the platen. This assembly can be arranged relative to the surface of a fluid that is to be placed into the through-holes through which pins have been inserted. The tips of the pins can be brought into contact with the fluid surface, and, on retraction, small volume drops can adhere to the end of each pin. As the pin array is retracted relative to the through-hole array, the liquid drops can come into contact with the through-hole into which the pin has been inserted. As the pin leaves the through-hole, surface tension can keep the fluid volume inside the through-hole.

An advantage of both embodiments is that they provide a rapid, simple, and precise method by which fluid can be loaded into through-holes of an array. Fluids containing surfactants can, for example, be easily transferred into the array with minimal contamination between adjacent through-holes because of the long path along the array surface separating the ends of adjacent pins.

Synthesis of a Stochastic Array

A stochastic array can be created using a nozzle moving randomly to different through-holes on the array. Loading the through-holes in a stochastic method, wherein one variable of the sample is varied in a random manner has many applications. For example, the stochastic loading can vary with respect to the concentration of a particular reagent in the sample loaded. The difference in concentration of the reagent allows simultaneous sampling, in a controlled manner, of many different reaction conditions. For example, this sort of application of samples can be used to optimize reaction conditions in chemical synthesis or can optimize parameters of a crystallization experiment.

IV. Reactions/Experiments in the Platens
Synthesis of Combinatorial Libraries

The present invention provides new methods for producing a combinatorial library in a platen. The types of combinatorial libraries that can be produced using the new methods include, but are not limited to, nucleic acid arrays, peptide arrays, protein arrays, polymer arrays, and arrays of small molecules.

Certain of the new methods include immobilizing a linker molecule on the inner walls of the platen's through-holes, or in a porous material located inside the through-holes, and sequentially flowing reagents through masks to build a pattern of chemicals. For example, to create a nucleic acid array, phosphoramidite monomers can be sequentially placed in the through-holes in defined patterns with activation, reaction, washing, and deprotection steps in between each addition of monomer. To create an array of small molecules using solid or liquid phase synthetic chemistry, linker molecules with, for example, protected amide groups can be sequentially placed in the through-holes in defined patterns with washing and deprotection steps between each synthetic reagent addition step. Chemical synthesis with solid phase chemistry can be carried out on core molecules linked to the interior surface of a through-hole, inside a porous material placed in a through-hole, or on a polymer bead placed in the through-hole. Core molecules with chemically active side groups can also be prepared in the through-holes using solution phase chemistry.

Chemical and Physical Process Optimization

Optimization of a chemical or physical process requires searching a multivariate space of experimental conditions for a subset of those parameters producing the desired outcome. The search strategy can be either systematic or stochastic; either or both strategies can be implemented as embodiments of the present invention. Systematic optimization is aided by producing an array of chemical or physical conditions from one through-hole to the next in a known and regular way.

Stochastic variation of reagent concentrations from one through-hole to the next can be accomplished, for example, by first uniformly loading an array with a first reagent. A container holding a second reagent can then be positioned above the array, for example, on a motorized two-axis mount, and the second reagent can be dispensed through a nozzle with an electronically controlled valve. The nozzle can be moved to different randomly selected array positions (or to positions determined by an algorithm), and the amount of liquid dispensed through the nozzle can be determined by a randomly selected (or algorithm-selected) time duration less than a pre-selected maximum. In this manner, different amounts of the second reagent are dispensed into through-holes containing the first reagent. This process can be repeated with additional reagents as needed. The reactions with optimal outcomes can be identified by analyzing the contents of the through-holes. If the second reagent is distributed randomly, rather than according to an algorithm, lack of specific knowledge regarding the starting conditions for these reactions can make duplication difficult. However, if one is interested in the reaction products alone, then a stochastic approach can provide a facile method for rapidly searching a large experimental parameter space for a desired reaction outcome. Moreover, the reaction conditions can sometimes be inferred, for example, by examining the contents of other through-holes in the array where little or no reaction occurred, and then combining the results in a multivariate plot. Optimal reaction conditions can be inferred from domains containing little or no data. Another approach to assess initial reaction conditions is to produce a replica plate using the same dispensing protocol but into an array uniformly loaded with solvent without any of the first reagent. Comparison of through-holes showing the desired chemical activity with the contents of the corresponding through-hole in the replica plate would provide information as to the most likely starting conditions of the observed reaction.

If large numbers of conditions need to be tested, the multiple reagents can be randomly sprayed onto the array until all of the through-holes have been filled. The surface can then be wiped with a rubber spatula to remove excess fluid. A reaction can be initiated by stacking the array with a second array, and the result can be probed optically. Because the contents of each address in the array will be unknown, one can either chose promising addresses, and then analyze the contents to determine what was in the hole, or else replicate the plate prior to initiating the reaction, and then use the replicate plate to determine the optimal conditions.

These examples also allow for physical parameters to be either systematically or randomly varied from one through-hole to the next. For example, a temperature gradient can be imposed across one or two-dimensions of an array fabricated from thermally conductive material, for example, by holding the edges at different temperatures. If the temperature of a heating/cooling source is changed with time, then the temperature distribution across the array can be varied. The rate of temperature change is generally proportional to temperature; thus, both the temperature and the rate of temperature change can vary from one through-hole to the next. Alternatively, a focused laser beam can be directed to heat each through-hole independently, thus enabling control of the liquid in each through-hole with time as described, for example, in U.S. Pat. No. 5,998,768, incorporated by reference in its entirety.

Protein Crystallization

X-ray diffraction from crystallized proteins is an important analytical tool for determination of protein structure and function. Proteins can be difficult to crystallize because they generally include a multiplicity of hydrophobic and hydrophilic molecular groups. As a consequence, proteins often crystallize only under a specific set of solvent, pH, salt concentration, and temperature conditions. A high throughput method for protein crystallization is enabled by the present invention.

Screening Methods

The parameters that determine whether or not a biochemically efficacious compound is suitable for further development as a pharmaceutical compound include absorption, distribution, metabolism, excretion, and toxicology ("ADMET"). As the number of potential drug leads increases due to advances in primary high throughput screening, ADMET testing can become increasingly rate limiting in the drug discovery process.

Adsorption

Oral administration is the preferred route of administration for small molecule drugs. For an orally administered drug to have biological efficacy it must be bio-available (i.e. it must have the ability to pass through the gut and into the bloodstream). The ability to assess the ability of a drug candidate to pass through the lining of the gut in an in vitro assay is highly desirable. Typically, such absorption assays utilize a monolayer of cells grown on a semipermeable membrane that separates two liquid-filled chambers. The drug candidate is added to one of the chambers and after sufficient time for diffusion or transport, the concentration of the molecule in the other chamber is quantitatively analyzed.

One such absorption assay commonly used in the biopharmaceutical industry is the CaCo-2 absorption assay. The CaCo-2 assay interrogates the ability of a molecule to pass through a single layer of a colon cell line, known as CaCo-2. Typically, the rate of both apical to basal and basal to apical diffusion across the cell layer is determined. The CaCo2 assay is usually performed in an apparatus that provides two chambers of fluid separated by a porous membrane. The membrane is permeable to cell growth products, but acts as a support and impermeable barrier for the cells. A monolayer of cells is grown across the surface of the membrane, and the active or passive transport of molecules from one chamber to the other across this cell barrier is assayed.

The platens containing arrays of through-holes can be configured several ways to provide an array of absorption assays (e.g. using CaCo-2 or other cells), thus increasing throughput and minimizing reagent volumes. In one embodiment, a isotropically porous membrane (such as, but not limited, to a PTFE filter) treated to provide a biologically compatible surface for growing adherent cells. The membrane has dimensions at least the dimensions of the array of through-holes, and is placed on one platen so that it covers the through-holes of the platen. A second platen with matching through-holes is placed on the membrane so that the membrane is sandwiched between the two platens. Pressure is applied to the platens so that the membrane is collapsed between adjacent through-holes and no chemical crosstalk may occur between non-opposing through-holes, but allowing chemical communication between opposing through-holes for the assay.

In a second embodiment, the membrane is anisotropically porous, consisting of parallel pores through the membrane. Examples of this type of membrane are Isopore and Nucleopore filters sold by Millipore Corporation. As in the previous embodiment, the membrane is sandwiched between two platens, and pressure is applied. In this embodiment, pressure is not required to collapse the membrane between adjacent through-holes, but only to seal between adjacent through-holes. The parallel pores of the membrane allow chemical communication between opposing through-holes but not adjacent or non-opposing through-holes.

In a third embodiment, the membrane is patterned with regions of porosity spaced and sized like the pattern of through-holes in the platen. The membrane is sandwiched between two platens so that the areas of porosity match up with the through-holes, allowing chemical communication between opposing through-holes but not adjacent or non-opposing through-holes.

In a fourth embodiment, the membrane is made from a platen of through-holes, in which the through-holes contain a porous material, such as but not limited to porous silica. In this embodiment, the membrane platen is sandwiched between two platens of though holes, allowing chemical communication between opposing through-holes but not adjacent or non-opposing through-holes.

Metabolism

For metabolism studies, compounds can be tested for their propensity to be degraded by various cytochrome P-450 (CYP-450) enzymes or by liver microsome preparations. Propensity for causing drug-drug interactions can be estimated by assaying inhibition of various CYP450 enzymes by each drug or drug candidate.

An embodiment of this invention provides for measurement of cellular metabolism of compounds from a library. As described above in connection with adsorption assays, the compounds can be small organic molecules, peptides, oligonucleotides, or oligosaccharides. The cells can either be suspended in liquid, or can be grown as a monolayer of cells inside the through-holes or on a membrane having high longitudinal permeability and low lateral permeability. The membrane can include, for example, polymerized monomers in the through-holes of a plate, or hydrophilic/hydrophobic domains in a flexible membrane with domain size and center-to-center spacing equal to that of the through-hole array. Volumes of known concentrations can be loaded from the compound library into one through-hole array. The cell array or layer can be placed in contact with the library array and incubated, and the array composition can be analyzed to determine the change in compound composition or amount with cellular metabolism.

Toxicity

An embodiment of this invention provides for measurement of cellular toxicity of compounds from a library. As described above in connection with adsorption and metabolism assays, the compounds can be small organic molecules, peptides, oligonucleotides or oligosaccharides, and can either be suspended in liquid or grown as a monolayer of cells inside the through-holes or on a membrane having high longitudinal permeability and low lateral permeability. The membrane can include, for example, polymerized monomers in the through-holes of a plate or hydrophilic/hydrophobic domains in a flexible membrane with domain size and center-to-center spacing equal to that of a through-hole array. Volumes of known concentrations are loaded from the compound library into one through-hole array. The cell layer can be placed in contact with the library array and incubated, and the cells in each through-hole can be analyzed for viability.

Ligand Screening by Affinity

It can be desirable to measure or rank the affinity of various members of a compound library toward a particular target macromolecule, or to measure the affinity of an analyte toward various members of a probe array. Such screening can be carried out using the new methods described herein. For example, affinity experiments can be carried out by immobilizing a target in many holes of the through-hole array and probing with a library of potential ligands, or by immobilizing a ligand library in an array and probing with a target.

Thermal Denaturation Ranking

As new drug targets are rapidly being discovered, methods are needed to find molecules with affinity to these targets in the absence of a functional assay. Fulfillment of this goal can be accomplished by immobilizing the target biomolecule on the inner surfaces of an array, incubating the holes of the array with a library of compounds, and detecting those members of the array that retain a compound. Bound compounds also stabilize target molecules to thermal denaturation to a degree that can correlates with the degree of affinity. By detecting unfolding of protein as a function of temperature or denaturing solvent condition, affinities can be ranked, as described, for example, in U.S. Pat. No. 6,020,141 to Pantoliano et al.

Gene Probes

An embodiment of the invention provides for the production of a through-hole array containing numerous, known nucleic acid sequences, adding a nucleic acid solution that has at least some unknown sequences to each of the holes in the array, providing sufficient time, temperature, and solution conditions for the unknown nucleic acid to bind specifically to complementary nucleic acids in the through-holes, and analyzing the degree of hybridization between the nucleic acids of known and unknown sequence in each through-hole. After binding, the array can be washed with a solution of the desired stringency. Often, the unknown nucleic acid has a fluorescent probe attached. An advantage of the invention is that amplification of the signal can be achieved by using an enzyme reaction that is associated with the hybridized nucleic acids. For example, the unknown nucleic acid can be labeled with horseradish peroxidase and incubated with a substrate that produces a luminescent, fluorescent or chromogenic signal upon reaction with the enzyme following the binding and washing steps. Such amplification techniques can be incompatible with conventional nucleic acid arrays on planar surfaces, since the activated substrate in solution generally cannot be assigned to a particular point on the array due to diffusion. PCR or other thermal-cycling reactions may be performed in the array by submerging the array in a water-immiscible liquid such as an oil, alkane, or perfluorinated solvent. The array and water-immiscible liquid may be contained in a thermally conducting container such as a metal box, and then inserted into a thermal cycler adapted to receive the box.

Long-Term or High Temperature Culture of Cells

In order to minimize evaporation, it is known in the art to layer a small amount of a low volatility, immiscible liquid on top of a small volume of aqueous reaction media. For example, a small amount of mineral oil can be layered on a reaction vial containing a PCR (Polymerase Chain Reaction) reaction, in order to minimize evaporation during heating cycles. It is also known that fluids with high oxygen solubility contents can be used to enable oxygen transport to systems that require oxygen. It is a novel aspect of this invention that an immiscible fluid with a high oxygen solubility content can be used to eliminate evaporation from the array of sub-microliter samples, while facilitating oxygen transport to maintain cell viability.

In order to culture non-adherent cells in a nano-volume format for long periods (e.g., greater than 12 hours), it can be desirable to reduce evaporation by containing the cells in a hydrophobic, low volatility fluid. To allow for aerobic respiration or other gas exchange process to occur, an oxygenated emulsion of perfluorinated compounds can be used. These compounds have been the subject of clinical testing as artificial blood substitutes. Examples include perfluorodecalin, which is sold as Fluosol-DA™ by Green Cross Corp. of Japan; Oxycyte™, which is being developed by Synthetic Blood International; and Oxygent™-brand perfluorooctylbromide, which is being tested by Alliance Pharmaceuticals. In a typical application of these methods and materials using the through-hole array, cells are grown in a platen that is submerged in perfluorodecalin, while oxygen or air is bubbled through the medium in a manner that does not disturb the cells.

Culture of cells that adhere to the walls of the through-holes or to porous substances immobilized in the through-holes is comparatively simpler, as oxygenated aqueous media can be perfused through or around the platen as required.

Culturing thermophilic organisms under aerobic conditions at low volumes and high temperature can be particularly problematic, since evaporation tends to act quickly at temperatures such as 90° C. By submerging the array of through-holes in an appropriate fluorinated solvent, these temperatures can be used without significant evaporation, while maintaining a supply of oxygen to the cells.

Often the act of assay detection or sample "picking" may require that a platen be exposed to non-humidified environments or bright lights for a period of time. These are conditions under which evaporation from the through-holes can be problematic. In a typical experiment, sample evaporation is minimized by performing operations under a layer of immiscible fluid such as but not limited to perfluorodecalin, and samples may be added to or removed from the through-holes with a microsyringe while submerged under such a fluid. Other operations, such as imaging and platen manipulation such as platen stacking may be performed under the immiscible fluid as well.

V. Methods of Analyzing and Manipulating Output from Array Devices

Methods of Transferring Samples from Through-holes

Still another method features transfer into microtiter plates. In order to recover samples giving a positive response to a test, there is often a need to transfer fluid from selected through-holes in a high-density array plate to a microtiter plate having a lower density of wells. Often, this transfer process must be performed with sterile technique. This will allow for sampling of materials held in through-holes with selected properties from a larger collection of samples. There are three general methods for transferring fluids from the high density array plate to the wells of a microtiter plate: transfer with a single sampling device, transfer with a linear array of sampling devices and transfer with a two-dimensional array of sampling devices. Samples from proscribed through-holes can be removed by spatially localized mechanical action. One general embodiment is to insert a member through the hole to mechanically displace the material out the opposite side and into a receptacle positioned beneath the hole. A second general embodiment is to apply a localized gas or liquid jet to cause material in the hole to be displaced out the opposite end and into a receptacle positioned beneath the hole. A third, but slower, method is to transfer liquid from the hole to a waiting receptacle by transferring liquid onto a pin or into a syringe, moving the pin or syringe to the receptacle and dispensing the liquid.

In order to maximize throughput of the transfer system, the number of times that the low-density plate is moved should be minimized. If the high-density array is imaged and the imaged stored on a computer, the coordinates of the desired through-holes is available for input into the transfer apparatus. By aligning the high-density array above the low-density plate, and calculating which desired samples sit above an empty well in the low-density plate, a maximum number of samples can be transferred without re-positioning the low-density plate. The low-density plate can then be moved to a position that allows the greatest possible number of samples to be transferred in the next step. In order to minimize the cost of the transfer apparatus, the high-density through-hole array should remain stationary to avoid use of a high-precision alignment system. Some high-throughput systems that can be used in this way are described below.

Figure 9:
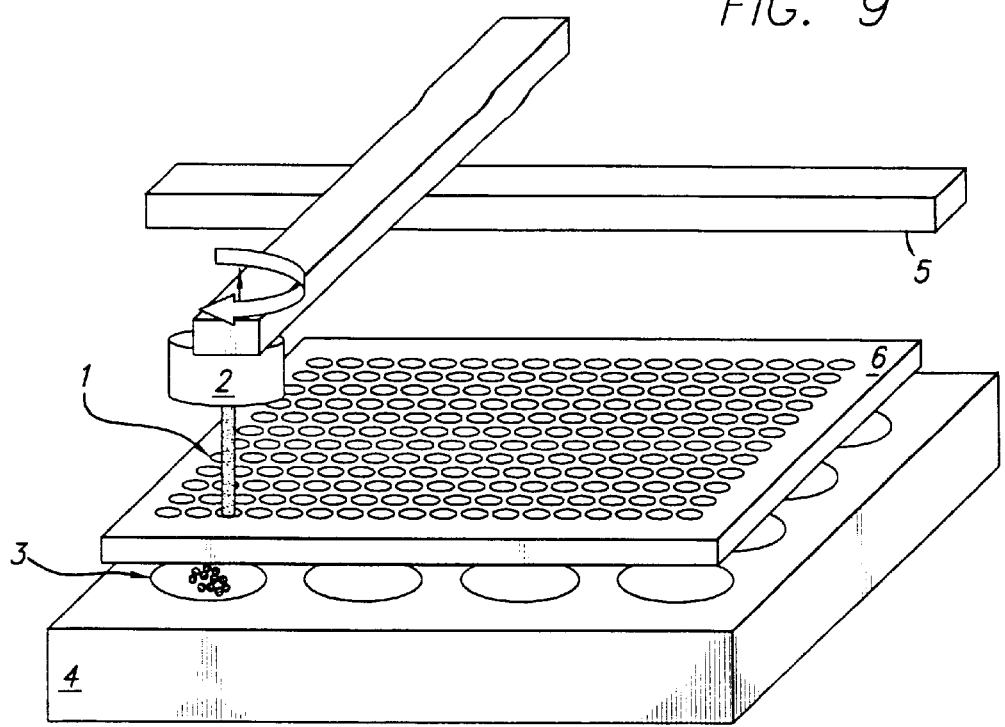
FIG. 9 is an illustration of a method for transfer with a single sampling device with a fast sequential positioning of a mechanical plunger over the through-holes to be sampled and pushing the plunger through the hole to transfer the hole's contents to the well of a microtiter plate located at a small distance below the through-hole array.

Another method features transfer with a single sampling device. This method can be accomplished, for example, by fast sequential positioning of a mechanical plunger over the through-holes to be sampled and pushing the plunger through the hole to transfer the hole's contents to the well of a microtiter plate located at a small distance below the through-hole array (6) (FIG. 9). The mechanical plunger (1) can be actuated by, for example, a linear electromagnetic motor (2). This process is repeated until each well (3) of the microtiter plate (4) contains the contents of a different through-hole. Once complete, the filled plate is replaced with an empty plate and the process is repeated. A servo-controlled, linear motor-actuated two axis stages (5) with magnetic or air bearings can position a mechanical plunger whose diameter is slightly less than a through-hole diameter to within <$\frac{1}{100}$ of a hole diameter (~1 $\mu$m) with velocities up to 1 m/s. Thus if 1% of a 100,000 hole array is to be transferred to microtiter plates and the time to sample each hole is on average 0.2 s, then 1% of the array can be sampled in about 200 s. This time excludes, of course, the time required to change microtiter plates, the time needed to sterilize the plunger between samples and, if needed, the time to position a well below the sampled through-hole.

Spatially Localized Gas, Liquid, or Solid Jets

Figure 10:
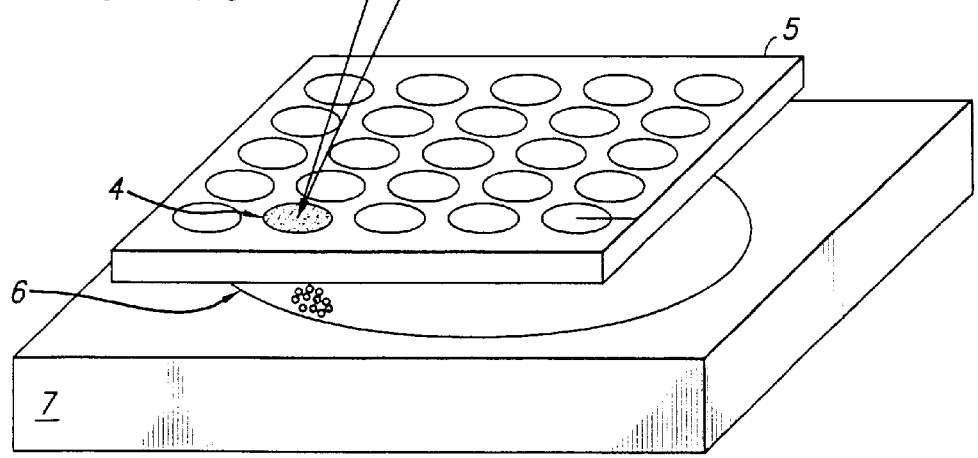
FIG. 10 is an illustration of a method for transferring materials from a through-hole in a through-hole array into a well of a microtiter plate using a gas jet generated by spatially localized heating with a focused laser beam.

With reference to FIG. 10, a beam from a laser (1) passes through a shutter (2) and can be directed by a beam scanning system (3) to be focused onto a specified through-hole (4) in a high-density array of through-holes (5). The laser wavelength can be chosen to coincide with an absorption band of a fluid in a targeted through-hole. The corresponding absorption coefficient can be such that a large percentage of the incident laser radiation is absorbed in a thin layer at the top of the liquid column. The shutter can control the length of time the liquid in the through-hole is exposed to laser radiation. When the shutter opens, laser light illuminates the liquid, and sufficient energy is absorbed during the exposure time to rapidly heat a thin liquid layer to vaporization, causing the rapid build-up of pressure at one end of the through-hole. The resulting force from the expanding vapor causes ejection of liquid from the opposite end of the hole (6) into a well of a microtiter plate located below the through-hole array (7). A further increase in force is possible if the volume above the heated surface is hermetically sealed thus increasing the pressure applied to the liquid. Rapid vaporization and expulsion of liquid from the column requires the laser energy to be deposited in a time less than the thermalization time. Rapid expulsion is needed to increase throughput and to prevent substantial degradation of the cells or reagents contained in the liquid.

The case of a water-filled through-hole provides an illustrative example. Indeed, in many cases, the analytical substance is in water. The absorption coefficient of water at 10.6 $\mu$m is ~1000 cm$^{-1}$ indicating 99% of the incident radiation will be absorbed within 46 $\mu$m of the surface—a small fraction of the water column's length assuming a length of 0.5 mm or greater. The thermalization time, $\tau$, is the time required for the water column to reach thermal equilibrium and is given by $\tau = l^2/4\alpha$ where l is the distance from the source of thermal energy and $\alpha$ is thermal diffusivity (=$\kappa/c\rho$) in which the thermal conductivity is $\kappa$, c is the specific heat and $\rho$ is the density. Inputting appropriate values for water, the thermalization time for a column of water 1 mm in length is 1.75 s while for a column 0.5 mm long, $\tau$ is 0.44 s. Adiabatic heating with the focused laser beam will take place if the laser pulse length $\Delta t$ is less than $\tau$.

The peak pressure generated by the instantaneous vaporization of a volume of water 46 $\mu$m thick by 200 $\mu$m in extent can be estimated assuming the water vapor is an ideal gas. The pressure, P, in this volume, V(=1.4×10$^{-12}$ m$^3$), when the liquid is vaporized is P=nRT/V where n is the moles of water (=88 nanomoles), T is the gas temperature (=373 K) and R is the ideal gas constant (=8.2 m$^3$-Pa/mole-° K). Inputting these values gives P$_{max}$=186×10$^6$ Pa equal to a force of 5.8 N on the water column; sufficient to expel the liquid from the through-hole.

The laser power to vaporize a 46 $\mu$m thick layer of water in a 200 $\mu$m diameter through-hole can be found by computing the energy, Q, to vaporize this volume of water: The thermal energy is found for Q=m (c$\Delta$T+$\Delta$H$_{vap}$) where m is the mass of the water in this volume (1.6×10$^{-9}$ kg), c is the specific heat of water (=4184 J/kg/° K), $\Delta$T is the temperature change (353° K) and $\Delta$H$_{vap}$ is water's latent heat of vaporization (=2.3 MJ/kg). Inputting these values gives Q equal to 6 mJ. Assuming 99% absorption of the incident laser energy, 6 mJ is deposited in the sample by a 10 W laser illuminating the liquid surface for 0.6 ms. For random-access scanning, typical settling times for galvanometer-steered mirrors is 10 ms and for 1000 through-holes in an array to be individually addressed, it will take approximately 10.6 seconds.

Figure 22:
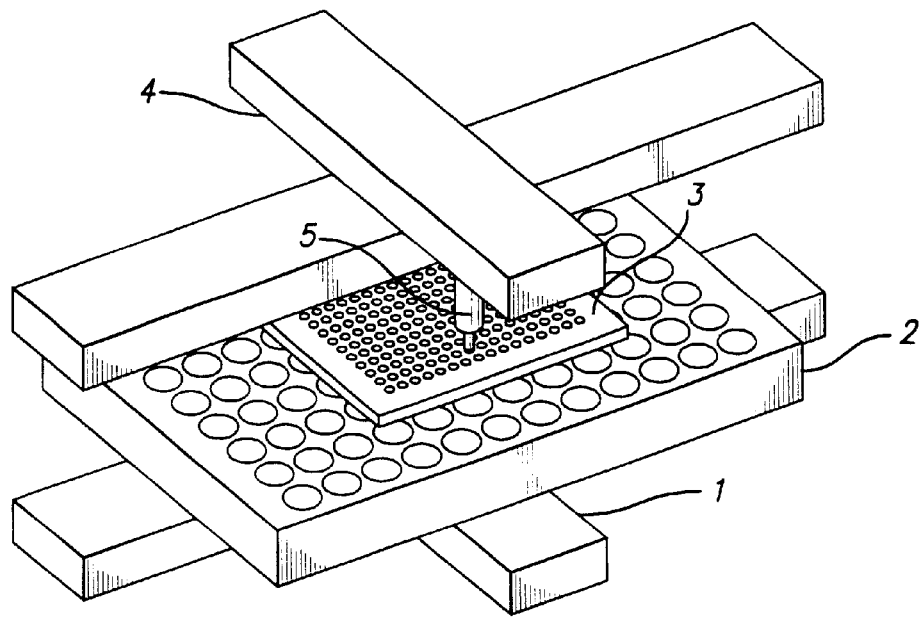
FIG. 22 depicts a device for removal of the contents of a through-hole array and transfer of those contents. The device has a nozzle, a stage for holding the through-hole array and a stage for holding a capture chamber. Movement in two dimensions of the nozzle or the through-hole array can be achieved.

In alternative embodiments, solids (e.g., powders) or liquids can be used to displace or force out (e.g., under pressure) the contents of specific through-holes or the contents of the through-holes in general. (See FIG. 22) Examples of liquids that can be used include liquids that are miscible with the contents of the through-holes (e.g., water when the contents of the through-holes are aqueous) or liquids that are immiscible with the contents of the through-holes (such as oils or organic solutions when the contents of the through-holes are aqueous). Application of pressurized liquid to an array can be used to wash contents of each hole into, for example, a common container.

Explosive charge

An extension of the previous embodiment is the expulsion of the liquid from a through-hole by a pressure wave generated by rapidly expanding gas on ignition of an explosive charge located in proximity to one end of the through-hole. With reference to FIG. 10, an array of discrete slow-burning explosive charges (1) is co-registered with respect to the through-hole array such that one charge is located above one through-hole. Each charge is placed in a chamber having a thin membrane as a common wall with the through-hole. The charge array is bonded (or tightly attached to) the through-hole array. Examples of explosive material for this application include plastic explosive sheets such as "C4", or trinitrotoluene (TNT) embedded in plastic. The charge array is addressable, for example, electrically or optically. An individual charge can be ignited by passing an electrical current through a resistive element (2) located in the chamber or by the thermal energy deposited in the chamber by a focused laser beam. Once ignited, the expanding gas from the explosion generates sufficient pressure to burst the separating membrane and drive liquid (3) from the through-hole (4) into the well (5) of a microtiter plate (6) located below the through-hole array (7).

Figure 11:
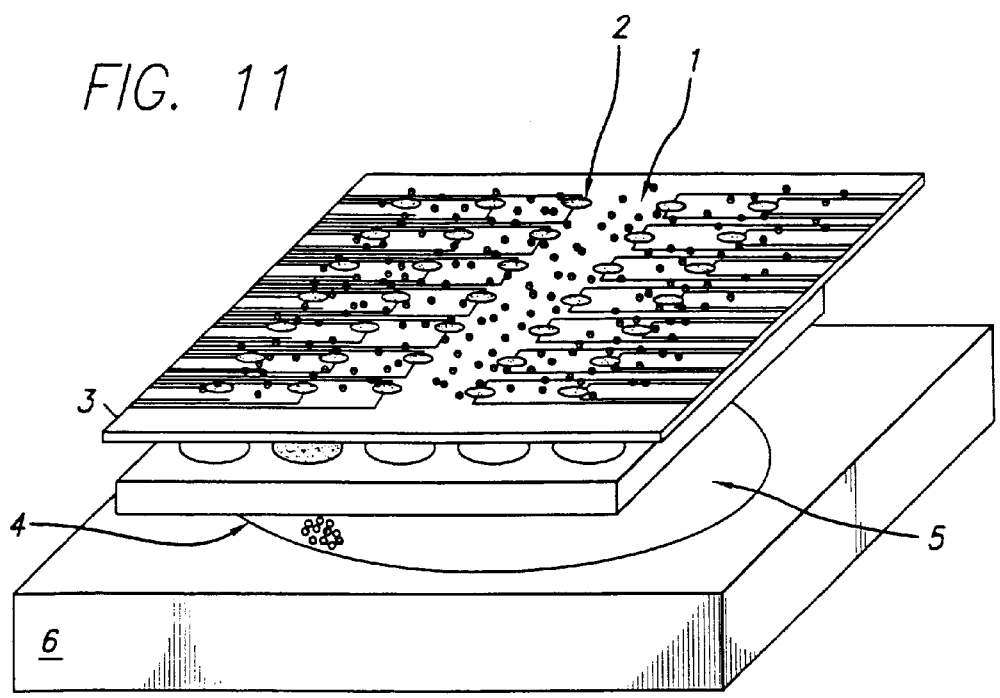
FIG. 11 is an illustration of the transfer of material from a through-hole in the array to a well in a microtiter plate with a gas jet caused by localized ignition of an explosive charge randomly distributed in a thin sheet overlaid on one surface of the through-hole array.
Figure 12:
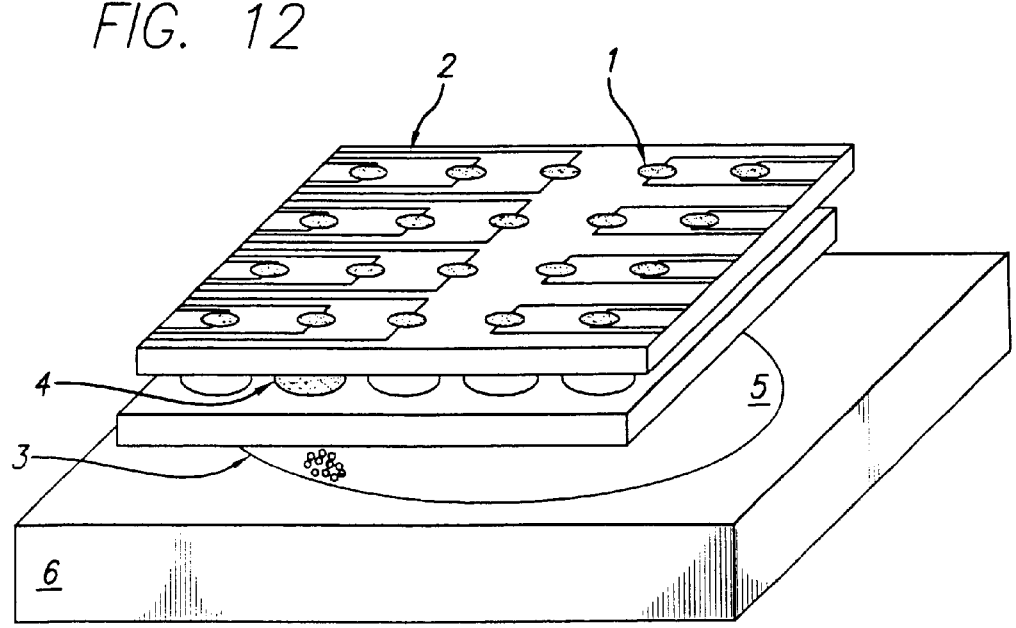
FIG. 12 is an illustration of a sheet with an explosive charge pattern matching the through-hole positions in the array.

Alternatively, as shown in FIG. 11, the explosive charge can be embedded as a uniform stochastic distribution in a thin plastic sheet (1). Conversely, the explosive chemicals could be printed onto the sheet in the same pattern as the through-hole array, as shown in FIG. 12. Printed onto the sheet are resistive elements (2) at discrete spatial locations with the same pattern as the through-hole array. Alternatively, spatial locations on the sheet are addressable by a focused laser beam providing the energy required to ignite the explosive chemicals. The sheet is bonded to the through-hole array (3) and the charges ignited above the through-holes whose contents (4) are to be transferred into a well (5) of a microtiter plate (6) located below the through-hole array.

To increase the inertia imparted to the liquid column from the expanding gas charge, metal or ceramic microspheres are mixed with the explosive charge and are accelerated by the explosion. Alternatively, a plug of material between the explosive charge and liquid column accelerated by the explosion will act as a mechanical plunger to expel liquid from the through-hole.

Forming the exit of the chamber containing the explosive charge into a nozzle will increase the spatial localization and inertia of the exiting gas before impacting the liquid column. The nozzle exit either is fluid with the chamber surface or protrudes slightly to insert into the opposing through-hole.

Sample Aspiration

Liquid samples in a through-hole or group of through-holes can be transferred out of the through-holes by aspiration into a tube or channel. The tip of a piece of flexible or rigid tubing, generally having an outer diameter narrower than the inner diameter of the through-hole, can be aligned within the through-hole. Application of negative pressure to the distal end of the tubing can then be used to aspirate fluid from the through-hole into the tubing. The amount of fluid to be aspirated can be accurately controlled by manipulating several variables. For example, the length and internal diameter of the tube can be determinative of the pressure drop across that piece of tubing, which can in turn affect the rate of flow through that piece of tubing for a given amount of applied negative pressure. A metered amount of fluid can be aspirated from the through-holes into a valve assembly, from which the fluid can be moved by positive or negative pressure to any type of fluidic circuit that is required by a given application. In one embodiment, fluid is aspirated from a through-hole into a fluidic valve. Actuation of that valve introduces the fluid via positive pressure to a mass spectrometer for analysis of that fluid. Alternatively, further sample preparation or characterization (e.g., chromatography, spectroscopy) can be performed on the fluid once it has been aspirated from the through-hole.

Electrophoresis and Electroblotting: The invention also provides methods for introducing an ionic sample into a through-hole array containing chemical probes, for modulating the stringency of the binding between the probes and certain ions in the sample, and for removing an ionic sample from the through-hole array. The method includes placing the through-hole array containing chemical probes localized in the holes into a buffer in an electrophoresis apparatus. A sample containing ions is introduced into the electrophoresis apparatus on one side of the planar through-hole array, such that when an electric field is applied, the ions of the appropriate charge will migrate in the direction of the through-hole array. If a particular ion does not bind to the array and the electric field is applied for sufficient time, that ion will migrate through the hole to the opposite side of the through-hole array. By periodically changing the direction of the electric field, approach to equilibrium in the binding between the charged species and the chemical probes in the through-holes can be accelerated. Partial purification of the sample to be analyzed can optionally be achieved by electrophoresis of the sample through a gel prior to its migration to the through-hole array. Once the analytes of interest in the sample have associated with the chemical probes, the field can be applied for sufficient time and with sufficient strength to dissociate non-specifically bound ions from the chemical probes. The through-hole array can then be taken from the electrophoresis apparatus, and the pattern of binding can be analyzed. The bound analytes can also be removed for further analysis, for example, by electroblotting onto a membrane, and then removing the membrane for further analysis.

Chromatic Analysis of Samples in an Array of Through-holes

For many applications, samples must be isolated, purified, or concentrated by a chromatographic step. Many different types of chromatography can be performed on liquid samples. Examples of well-known chromatographic methods include, but are not limited to, ion exchange, reversed phase, size exclusion, bio-affinity, and gel permeation chromatography. The chromatography matrix can be in the form of an insoluble bead, gel, resin, polymer, or slurry. The matrix can alternatively be a micro-machined structure. One embodiment of such a micromachined structure is a grouping of square through-holes or channels with sides of dimension on the order of 0.01 to 10 µm. The walls of these through-holes can be coated with a surface having a desired affinity such that a separation is achieved as sample is flowed through the group of through-holes. The analyte mixture of interest is then introduced to this matrix and selective binding of components of the analyte mixture to the matrix takes place. Analytes of interest or contaminants can then be selectively eluted from the matrix by changing the physical or chemical environment of the matrix.

Liquid chromatography is typically performed in a column in which the chromatography matrix is immobilized and the analyte is flowed through the column, allowing chemical and/or physical interaction between the sample and the chromatography medium to take place. The length and internal diameter of the array of capillaries generally determines the amount of chromatography matrix that can be loaded into each column and, therefore, is directly related to the loading capacity of each column.

Immobilizing a chromatography matrix inside an array of through-holes can create an array of miniature liquid chromatography columns. A suitable length-to-diameter ratio of the array of through-holes can be selected. Typically, a minimum length-to-diameter ratio of at least about 10 is required to form an effective chromatography column. In certain embodiments, the internal diameter of the columns formed in the through-holes is less than a millimeter, allowing for precise and accurate manipulation of very small amounts of sample. The chromatography matrix can be immobilized within the chromatography columns by positioning a porous frit at the exit end of the column or by chemically binding a porous polymeric ceramic or glass substrate to the inside of the column. The porous ceramic or glass substrate can either act as a frit to immobilize a bead or resin chromatography media or as a method to increase the total surface area within a column. In surface-effect driven chromatographic methods (e.g., ion exchange, affinity, or reversed phase chromatography), chemical derivatization of the interior surface of the columns can provide the necessary separation.

In one embodiment, samples are loaded into the array of columns with syringes. A submicroliter volume of sample can be drawn into the needle of the syringe or a bank of syringes with a spacing co-registered to the spacing of the array of columns, and then transferred to the array of columns. The barrels of the syringes can contain a larger quantity of liquid for performing wash and/or elution steps in the bundle of capillaries. The sample in the needle of the syringes and the liquid in the barrel of the syringes can be isolated from one another by drawing up a small amount of air into the syringes. The needles of syringes can be docked into the array of capillaries with a liquid-tight compression fitting. As the content of the syringes are ejected into the array of columns the samples in the needles of the syringes initially elute onto the column bed. The chromatography media used and buffer drawn into the barrel of the syringe will dictate the chromatographic separation. Once the samples have been loaded onto the columns, the syringes can be removed from their docking ports and a second aliquot of a similar or different buffer can be drawn into the syringes. As many wash and/or elution steps as necessary can be performed by re-docking the syringes to the array of capillaries by tightening the compression fitting and ejecting the liquid from the syringes. A first array of columns can also be mated to a second array of columns for further separation.

It is often desirable to analyze the eluate from a chromatography column in real time using a variety of spectroscopic methods. Spectroscopic devices for interrogating the eluate from a chromatography column are well known. If required by the specific application, the eluate from each column in a bundle of columns can be analyzed on-line in real time, spectroscopically (e.g., by absorption, fluorescence, or Raman spectroscopy), electrochemically, or otherwise. The light from the spectroscopic light source can be delivered to and recovered from the eluate of each column in a bundle of columns as it passes through an observation window machined into the exit capillary of that column with a fiber-optic cable.

Mating an Array of Through-holes to an Array of Liquid Chromatography Channels

A device can be manufactured to include an array of chromatography columns with a chromatography matrix immobilized within the array of columns, for example, with spacing such that it can be co-registered with the through-holes in an array of through-holes that do not contain a chromatography matrix. The physical size of the array of through-holes can determine the size of the array of columns. Preferably, the internal diameter of each column in an array of columns will be similar to the internal diameter of the corresponding co-registered through-hole in an array of through-holes.

The array of columns should be mated to the array of through-holes in a manner that allows the application of a positive or negative pressure across the device and does not result in cross talk between the individual samples. The number of columns need not be in a one-to-one ration with the through holes. Radial diffusion of samples between the layers of a stack of arrays of through-holes in response to an applied external pressure may result in cross talk and must be avoided. Inter-sample cross talk can be eliminated by forming a liquid-tight seal hermetic seal between the through-holes to eliminate radial diffusion. An elastomer sheet with holes co-registered with the through-holes in the array can be compressed between the layers of a stack to form such a seal. Alternatively, a thin, inert, porous polymer sheet can be placed between the two arrays such that, when the two columns are pressed together, liquid can flow through the pores in the sheet, but cannot flow laterally. Another approach entails manufacturing the array of through-holes such that one side of the immediate area around each through hole is raised relative to the rest of the array. An o-ring can then be placed around this raised area. When two or more arrays of through-holes are compressed together, the o-rings will form a hermetic seal, thereby eliminating radial diffusion and sample cross talk. The cross-section of any pair of mating arrays can also be fabricated to be interlocking with an elastomer gasket or coating between the mating surfaces, to provide a leak-tight fluidic seal.

Figure 14:
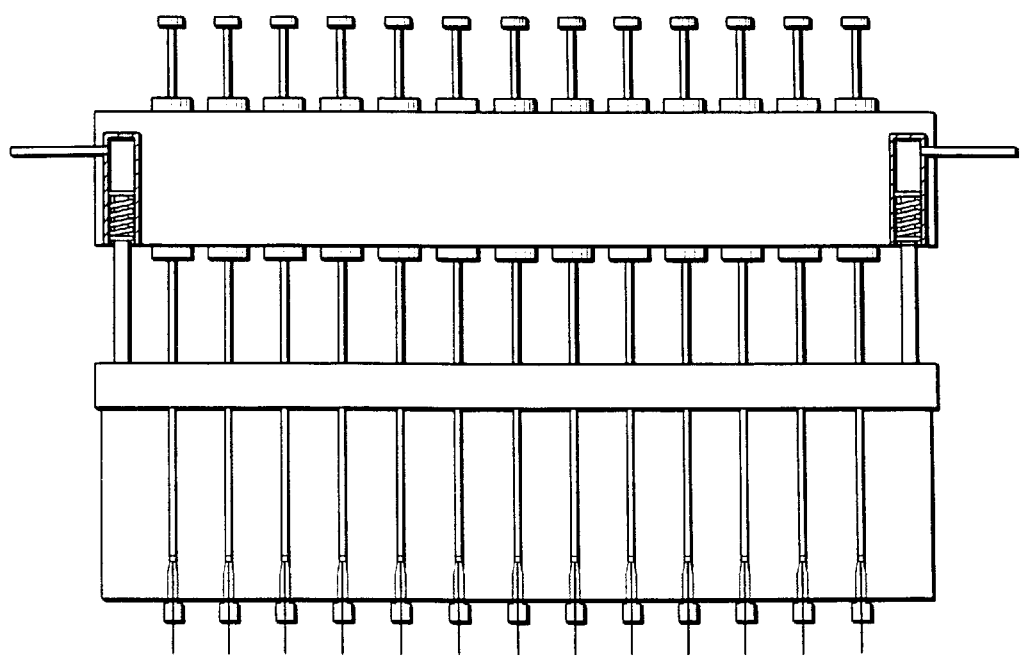
FIG. 14 is an illustration of a chromatographic device.

One or more arrays of through-holes can be mated to an array of columns in a similar manner. A top plate can then be affixed to the assembly that allows for the necessary chromatographic wash and/or elution buffers to be applied to the each through-hole. The liquid can be forced through the device in such a manner that the sample will be pushed through the array of through-holes into the array of columns upon which the chromatography will take place. If required by a specific application, the wash and/or elution buffers from the chromatography columns can be transferred via capillaries to another chromatography device, chromatographic fraction collector, or another array of through-holes. An illustration of such a device is shown in FIG. 14. The fluidic connections that lead to and from the device can be machined for easy coupling to standard fluidic connections using standard fluidic components such as ferules and compression fittings.

Device for Fraction Collection

Chromatography generally entails separation of a mixture of compounds on the basis of differential chemical and/or physical interactions of the individual components of that mixture with a chromatographic matrix. A sudden or gradual change in the physical and/or chemical environment can affect the interactions between the components of a mixture and the chromatographic matrix. Typically, each component of a mixture elutes individually from the chromatographic matrix as the physical and/or chemical conditions are varied. It can be desirable to isolate a given component of a mixture of compounds for further analysis or chromatography. In some cases, a component of interest can be identified by online spectroscopic analysis.

Devices for fractionating the eluant of a chromatographic column and storing individual fractions are well known. One embodiment of the present invention features a system for collecting chromatographic fractions from an array of columns. The column eluate can be spotted dropwise onto another array of through-holes. By controlling the speed at which the array of through-holes is moved with respect to the array of columns, the volume of each fraction can be controlled. A fluid bridge can be formed between the exit capillary from the array of columns and a through-hole in a through-holes array if the interior surface of the through-hole is coated with a material with the appropriate affinity for the eluant. The maximum number of fractions that can be collected from a given column will depend on the size of each fraction, on the speed at which the collection array of through-holes is moved, and on the density of the array of columns. If a large number of fractions must be collected from each column, a linear array of columns can be used, its output being collected in a two-dimensional array of through-holes. If the fraction collection array of through-holes is then moved perpendicularly to the linear array of columns, the number of fractions that can be collected is limited only by the physical size of the collection array.

For some applications, a single chromatographic separation can take several minutes or longer to complete. If long periods are required, it is possible that evaporation of liquid from the array of through-holes in the fraction collection device will occur. To avoid evaporative loss from the through-holes in the fraction collection device, the entire array of through-holes used to collect fractions can be placed within an environmentally controlled enclosure. If a high-humidity environment is maintained within the enclosure, evaporative losses can be minimized. Additionally, it can be desirable to maintain a certain temperature within the enclosure (e.g., 4° C.) to maintain compound stability. The elution capillaries from the array of columns can enter the enclosure through a series of precision-machined holes to maintain the integrity of the enclosure while allowing for introduction of the eluant from the array of columns. Elastomer gaskets may be used to ensure a good seal around the enclosure.

An array of through-holes containing the fractions collected from an array of columns can be stacked with another array of through-holes to initiate a second mixing operation to initiate a chemical reaction. A second chromatography application can be initiated by stacking the array of through-holes into which the fractions were collected with a second array of columns. Alternatively, further spectroscopic or spectrometric analyses can be performed on the collected fractions at this time.

Spectrometric Analysis of Compounds in an Array of Through-Holes

Atmospheric pressure ionization mass spectrometry (API-MS)

Samples in an array of through-holes can be analyzed by a spectrometric technique such as atmospheric pressure ionization mass spectrometry (API-MS). The spectrometric analyses are typically performed serially. Therefore, the chips should be environmentally isolated in a controlled temperature and humidity environment to avoid loss of sample due to evaporation. In API-MS, one simple method for introducing the sample to the mass spectrometer features aspirating a selected sample directly from a particular through-hole into a valve using a length of capillary tubing (e.g., as described herein). A metered volume of sample can then be introduced into a mass spectrometer using standard API-MS protocols.

Matrix Assisted Laser Desorption Ionization Time of Flight Mass Spectrometry (MALDI TOF-MS)

In MALDI TOF-MS analysis, a sample of interest is generally mixed with one or more matrix-forming compounds. Typically, a saturated solution of an organic matrix material (e.g., derivatives of hydroxycinnamic acid) is mixed with an equal volume of sample. In some applications of MALDI TOF-MS, the organic matrix compound is replaced by inorganic nanoparticles (e.g., colloidal gold, quantum dots, or porous silica). The mixture is then spotted in the form of a regular and addressable array on a flat plate and allowed to evaporate completely. The sample plate is then positioned in the mass spectrometer, and the samples are ionized by irradiation from a pulsed laser.

Samples in an array of through-holes are well suited for analysis using MALDI TOF-MS and related applications, since the necessary sample preparations steps can easily be accomplished in a parallel fashion. For example, a second array of through-holes can be loaded with a saturated solution of an organic matrix or a slurry of an inorganic matrix compound. The array of through-holes can either be dip-loaded uniformly, or, if desired, any number of different matrix compounds can be loaded into individual through-holes in an addressable fashion. The sample and matrix arrays of through-holes can be mixed together by bringing the chips together (e.g., as described herein). After allowing the solvent to completely evaporate, the array of through-holes can be placed in a slightly modified receptacle in most commercially available MALDI TOF mass spectrometers. The conventional flat metal MALDI plate can be machined down to compensate for the thickness of the array of through-holes. The array of through-holes can be affixed with a temporary adhesive within the recessed area of the standard sample holder.

The laser used for sample ionization in the MALDI TOF mass spectrometer can be focused within the through-hole to provide the necessary irradiance for sample ionization. Internal reflection of the laser beam within the through-hole can possibly increase the amount of laser energy absorbed by the matrix and transferred to the sample, thereby increasing the amount of sample ionization. Additionally, an array of through-holes can allow for a very high density of samples to be spatially located in a small footprint without inter-sample contamination.

Figure 15:
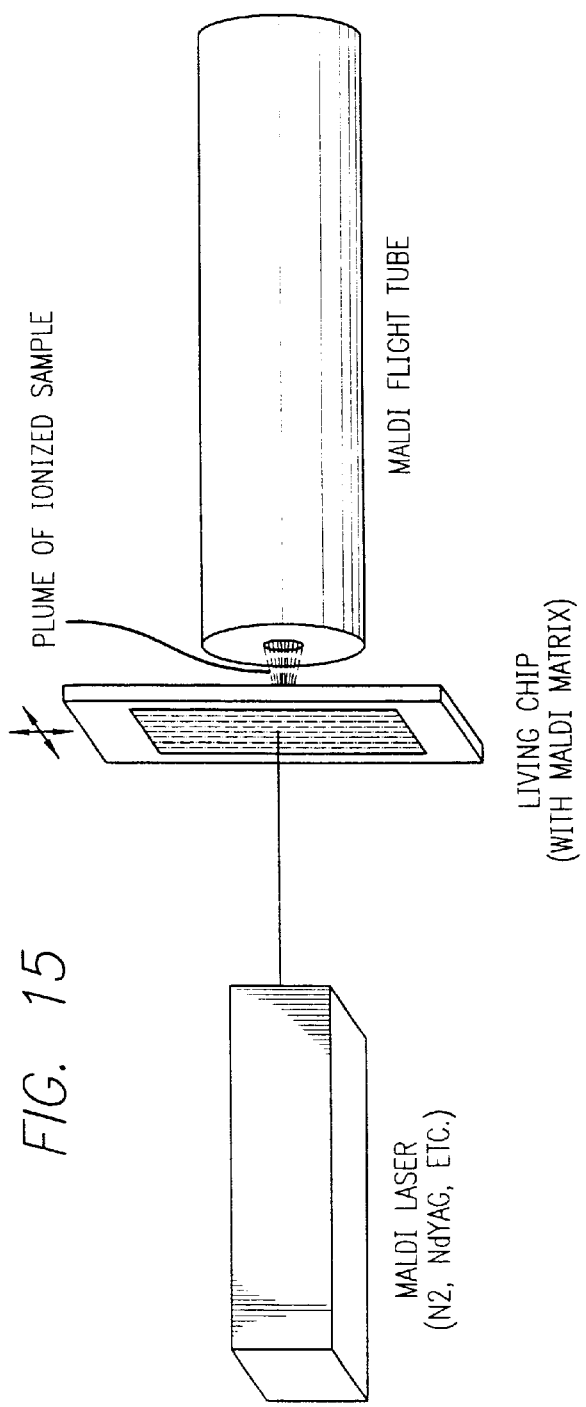
FIG. 15 is an illustration of a linear MALDI-TOF mass spectrometer.

Typical MALDI-MS sample plates are solid surfaces onto which samples are spotted. The laser used to ionize the samples must be on the same side of the plate as the inlet of the flight tube of the mass spectrometer, since the sample plate is opaque to the laser energy. The use of an array of through-holes as the sample plate allows for the source of laser irradiation and the inlet to the TOF mass spectrometer to be located on opposite faces of the sample plate. A scheme of this linear MALDI TOF mass spectrometer is shown in FIG. 15. Translocation of the sample plate in front of the inlet of the flight tube allows for the laser ionization of a selected sample.

Alternatively, an array of posts or pins, precision-machined to fit into an array of through-holes, can be coated with the MALDI matrix material by dipping the array into a bulk matrix solution. After the solvent has evaporated, the pin array can be inserted into the through-hole array. Fluid contained in each through-hole is transferred to the corresponding pin surface. After the solvent has evaporated, the pin array can be placed at the input to a TOF mass spectrometer and the pins can be illuminated sequentially with a focused laser beam. In such a pin array, a portion of the sample from each through-hole can be held isolated from its neighbor by the air gap between each pin.

Through-hole Array/Surface Method

When placed into an electric field or driven by pressure, the through-hole array can be used as a parallel capillary electrophoresis, electrokinetic chromatography or chromatography device. An array of samples in one through-hole array can be introduced into a second, typically longer, through-hole array. The second through-hole array can be filled with a gel (e.g. silica), a polymer (e.g., polyacrylamide) or a resin and can have a coating on its walls to prevent or enhance electro-osmosis or protein binding. However, if electrophoresis or chromatography is performed in such an array, it will be difficult to analyze the output of each column as molecules emerge from it. One way to alleviate this problem is to pass the output through a moving surface (e.g., nitrocellulose sheet) with an affinity for the analyte molecules and then move the web to an imaging detector. For example, fluorescently labeled DNA or protein could be eluted onto a moving nitrocellulose membrane and passed to a fluorescent imager to analyze. A continuously moving surface, moving in the manner of a tape, would cause smearing of the samples, therefore it is advantageous to reduce or reverse the polarity of the electric field or pressure during those periods of time when the surface is moving. An increase in sensitivity of the detection system is can be achieved by further delaying the movement of the surface and the voltage or pressure while the detector is acquiring an image. Alternately, the imager could be a line-scanner such as a fluorescence laser line-scanner. The surface could be fed from a long spool if desired (e.g., in a tape like manner). The surface can further be taken up on a second spool.

Readout Methods

A Method of Using Wetting Properties of the Array to Detect Chemical Binding to the Walls of the Through-holes The binding between two proteins, such as between an antibody and an antigen is detected via its affect on the surface energy of the channel interiors.

In a preferred embodiment, a library (e.g., a library of antibodies, receptors, macromolecules, or molecular probes) is bound to the interior walls of a through-hole array having hydrophilic channel walls and hydrophobic faces. The array is rinsed with a blocking agent, which binds to non-specific protein absorption sites on the channel walls but does not change the hydrophilic character of the wall surface. Such blocking agents include bovine serum albumin (BSA), powdered milk, and gelatin. The array is then immersed in a solution that contains antigen and is incubated for sufficient time to allow binding of antigen to complementary antibody. The arrays are then removed from the antigen solution and washed with buffer. The array is dried and dipped into an aqueous solution containing a chromophore or fluorophore. The presence of the antigen on the surfaces lowers the surface energy sufficiently such that the liquid is prevented from entering the through-holes. The empty through-holes can be identified by imaging the array. The empty through-holes then correspond to the antibodies in the library that effectively bind the ligand.

In another embodiment, the interior walls of a set of small array devices, each having roughly 1–100 through-holes, are coated such that each array has a different antibody. The arrays are placed together in a solution of antigen and incubated for sufficient time to allow binding of antigen to complementary antibody. The arrays are then removed from the antigen solution and washed with buffer. All arrays are then placed together in a separation bath that contains a liquid that is non-destructive to the proteins and can be adjusted in density in some manner (e.g., by addition of a higher density liquid, or by adding a thickening agent). When the holes remain empty, the density of the array in the bath is reduced and, under appropriate conditions, the array containing bound antigen can float to the surface. The presence of the antigen on the surfaces lowers the surface energy sufficiently such that the liquid is prevented from entering the through-holes. These floating arrays are removed and the identity of the antibody bound to each array is determined by mass spectroscopy, or from a code on each array, or by some other means such as a bar code or radio transponder built into the arrays. For this method the array can be a porous structure such as an aerogel or a porous bead.

A Device for the Analysis of an Array of Through-holes by Mass Spectrometry

Samples or aliquots of samples can be removed from an array of through-holes for analysis by mass spectrometry by one of several different methods. One such method features drawing the sample or an aliquot thereof into a tube with the application of negative pressure. In one example of this approach, the tip of a syringe is inserted into a selected through-hole in an array and a metered amount of sample is drawn into the syringe. Alternatively a vacuum could be used to aspirate the samples into a length of tubing, a valve, or a container for storage.

For certain applications, it can be desirable to assay each sample in an array of through-holes by a serial process such as mass spectrometry. Application of a serial process to a large number of samples in an array of through-holes, even if done very rapidly, can still require a significant amount of time. If humidity conditions and temperature are not strictly regulated during this time, evaporation of samples from the through-holes can occur and artificially bias assay results.

One approach to controlling evaporation and facilitating the aspirating of individual samples from an array of through-holes is to design an additional array of through-holes in which each of the through-holes is coregistered with a sample through-hole in the assay. This additional array of through-holes can be placed on top of the arrays of through-holes used in the assay to create a top plate. The through-holes in this top plate can be designed such that the diameter of each through-hole can be made to be much larger at the outer surface than the diameter in the surface that contacts the arrays of through-holes used in the assay. The conical shape formed by such a through-hole will act as a guide for a syringe needle into a selected through-hole and facilitate efficient sampling. The outer surface of this top plate can also be coated with a thin film of polymer similar to that used in lamination. The sealed surface will act to retard evaporation. The syringe needle used for aspirating the sample out of the through-holes can easily perforate this thin film and will not hinder efficient sampling.

Once the sample is aspirated into a syringe, it can be delivered into a mass spectrometer for analysis by any one of many techniques known by those skilled in the art. These can include atmospheric pressure ionization techniques such as electrospray ionization (ESI) or atmospheric pressure chemical ionization (APCI).

In another embodiment of the invention, a metal plate can be used as a bottom plate for the array of through-holes. The solvent used in the assay can be allowed to evaporate and a solid sample can form in a footprint on the bottom plate that corresponds to the internal diameter of the through-hole. If desired, a matrix can be added to the samples before complete evaporation. Alternatively, a matrix can be added to the surface of the metal bottom plate before it is stacked with the arrays of through-holes used in the assay. Once the samples have completely evaporated the metal bottom plate can be removed from the arrays of through-holes and each sample can be analyzed by matrix assisted laser-desorption ionization (MALDI) or a similar surface based ionization mass spectrometry technique generally practiced by those skilled in the art.

In another embodiment of the invention, an array of pins coregistered with the array of through-holes can be dipped into the array of through-holes and removed. Sample that is residually removed with the array of through-holes can be allowed to evaporate on the tips of the array of pins. As in the previous embodiment, this evaporated sample can be used for a surface based mass spectrometry method.

Time-gated Fluorescence Imaging of a Through-hole Array

Many biological assays are configured to give a fluorescent readout that can be acquired from an array of through-holes by fluorescence imaging. Typically, light from an excitation lamp or laser is passed through an excitation filter, through the array, through an emission filter and then to a CCD camera. In many cases, the sensitivity of the signal is limited by background light due to imperfect performance of the filters, and by inelastic and elastic scattering of light by the sample and optical components. Whereas the fluorophores of interest have fluorescence lifetimes of about 1 ns to 1 ms, scattering occurs at much shorter timescales. Thus removal of background light can be accomplished by the technique of time-gating. Time-gating the process of illuminating the sample while preventing the camera from acquiring data, quickly removing the excitation light, then waiting for a delay time before acquiring the fluorescence emission image. By not collecting photons emitted during the first 1 to 100 ps of after excitation, background noise is significantly reduced and signal to noise is improved. A similar apparatus can be used to repeat the data acquisition with varying delay times, thus yielding fluorescence lifetime information for each of the through-holes in the array.

Various strategies can be used to construct a time-gated fluorescence imaging system. A pulsed excitation source is needed and can be either a flash lamp or laser such as a passive or active mode-locked or Q-switched laser. If a laser is used, a beam expander and diffuser plate will give uniform irradiation of the platen. A continuous excitation source can also be used with a means for rapidly blocking and un-blocking the light such as an electro-optical, an acousto-optical cell or a rapidly rotating disk with slits. A pulse generator can be used to trigger the illumination source and detector at a given delay. The CCD camera can be electronically shuttered or physically shuttered as with a rotating disk with slits that is out of phase with the excitation pulsing.

Figure 21:
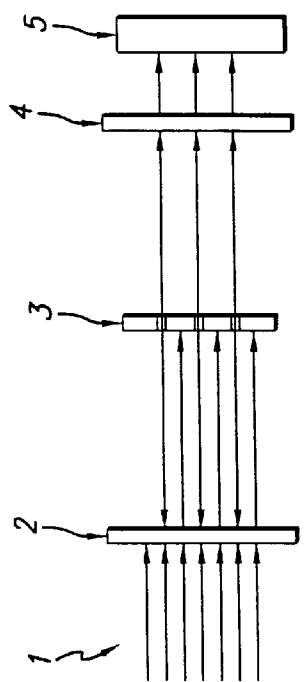
FIG. 21 depicts an array positioned inside an optical resonator featuring a source of illumination and two partially reflective surfaces.

Optical Readout Based on Insertion of a Through-Hole Array into an Optical Resonator or Interferometer A through-hole array can be inserted into either an optical resonator or an optical interferometer for simultaneous and parallel interaction of an optical field with material contained in each through-hole. (See FIG. 21) Such a method can be advantageous when the through-hole array (4) is placed in an optical resonator (Irradiation (1) is shined and amplified between mirrors (2) and (3).) so that the optical path length is increased over the length of the through-hole array, to increase absorption (5). The optical path length is increased as a multiple of the through-length, to increase optical absorption. For example, for simultaneous initiation of chemical reactions by the enhanced optical field characteristic of an optical resonator. It can also be advantageous as a means for simultaneous analysis of materials and interactions between materials contained within the through-holes, for example, by recording changes in incident optical field intensity, phase, polarization, or frequency, or by recording of these parameters, of light emitted from as a result of interaction between an incident optical field (e.g. fluorescence, phosphorescence), the materials contained in a through-hole, or a change in the material itself (e.g. luminescence).

One advantage of measuring these parameters with the chip as part of an optical resonator is that the resonator's resonance condition will change on interaction of the optical field contained within the resonator structure with the materials contained within each through-hole. These changes (e.g., phase, intensity, polarization, frequency) are intimately related to the composition and physical state of the material contained in the through-hole. The change in optical field parameters changes the resonant condition of the cavity, which, in turn, changes the intensity of light passed through or reflected from the resonator.

One can also take advantage of the increased optical field strength characteristic of optical resonant structures, for example, to initiate photochemical reactions or non-linear optical effects (multi photon absorption, harmonic conversion, etc.) as a probe to measure properties of the materials contained in the through-holes. The optical field incident on the resonator can be either continuous in time or it can vary with time as in an optical pulse.

Examples of optical resonator structures that can be used in this embodiment include Fabry-Perot-style interferometers with two planar mirrors and confocal Fabry-Perot-style interferometers having two curved mirrors or one planar and one curved mirror.

The through-hole array can either be part of or be inserted into a two-beam interferometer. Examples of such interferometers are many, and include Michelson, Twyman-Green, Sagnac, and Mach-Zhender-type interferometers. In the embodiment where the array is inserted into one of the optical paths of a two-beam interferometer, the phase of the light is delayed according to the complex refractive index (refractive index and absorption) as a function of wavelength. The interferometer can be illuminated with a beam of white light of sufficient width to also illuminate the through-hole array. For each optical path length difference between the two arms of the interferometer, a camera at the interferometer output can record the pattern of light exiting the interferometer and corresponding to light that has passed through each hole in the array. A series of images can thus be acquired for each optical path length difference, and taking the Fourier transform of each pixel of the image as a function of optical path length can generate an optical absorption or emission spectrum for the materials in each through-hole of the array.

Another embodiment uses a two-beam interferometer to analyze light passed through or emitted from a through-hole array. A camera records the light pattern from the interferometer for each optical path length difference imposed between the two plane mirrors that make up the interferometer. After recording a sequence of images corresponding to each path length difference, individual interferograms can be generated from each set of pixels coregistered across the image sequence. Application of the Fourier transform to each interferogram can generate an absorption or emission spectrum at each spatial position in the image. In this way, the spectral content of light interacting with material contained in each through-hole of the array can be determined.

Application of the approach described in U.S. Pat. No. 6,088,100, incorporated herein by reference in its entirety, adapted for full-field imaging, can also allow for capture of absorption spectroscopic information from each through-hole in a stack of through-hole arrays.

Image Center of Array as a Function of Thermal Perturbation

The invention is compatible with many systems for detecting the output of the arrays of chemical probes. Commercially available fluorescence scanners can be used if desired. Because each position in the array has two apertures (i.e., on the top and bottom faces of the platens), the array can be exposed to electromagnetic radiation on one face of the platen, and the optical properties of the samples in the array can be measured via detection at the opposite face of the platen. The positions of the array can be imaged in parallel or by serial scanning techniques. Both static and kinetic analysis of reactions can be utilized.

One method of detecting binding between an analyte and probes immobilized in the walls of the through-holes includes observing the distribution of analyte within each through-hole as a function of a perturbation. For example, a ligand of interest can be covalently attached to the inner walls of each of 10,000 through-holes in a 2 sq cm. platen. The chip can then be stacked with another chip containing, for example, a peptide library such that each member of the library occupies its own through-hole and has a fluorescent tag. After allowing sufficient time for non-covalent binding reactions to reach equilibrium, the chip can be rinsed with buffer to remove unbound material. By observing the fluorescence distribution in each hole as a function of a perturbation such as increasing temperature or increasing formamide concentration, the members of the library can be ranked as to binding energy. Binding kinetics can be determined by following the fluorescence distribution as a function of time following a rapid perturbation such as a temperature jump. The sensitivity of the assay can be improved by using a mask that includes of an array of through-holes complementary to the chip, but of smaller diameter, that spatially filters the light such that only the interior of each through-hole is observed. Another method of increasing signal-to-noise ratio includes applying a periodic or stochastic perturbation such as temperature, and then observing only signal correlated with the perturbation.

An increasingly common technique in drug discovery is millisecond time-scale fluorescence analysis of cell populations. Existing commercially available devices utilize a bank of syringes that add reagents from one 384-well microplate containing drug candidates to a second 384-well microplate containing cells loaded with a fluorescent indicator of calcium such as Fura-2, followed by laser scanning of the underside of the second plate to generate millisecond kinetic measurements of calcium release from the endoplasmic reticulum of the cells. It would be advantageous to use a white-light excitation source and a digital camera to acquire such kinetic data due to lower cost and greater choice of excitation wavelengths. This was previously difficult because the syringe bank would obstruct the light path in such a system and would haved to be moved on a millisecond time scale, which is not typically possible. Use of a white-light source is possible by initiating mixing of samples stored in an array of through-holes with cells growing in a second array, both arrays being in the camera system. An additional benefit of this method is that the throughput of samples collected is greatly increased by the use of through-hole arrays containing as many as 20,000 or more samples. Typically, the system is automated and will collect data that begins at the moment of mixing or otherwise indexes the times associated with collected data points to the moment of stacking. The types of assays possible with this method are not limited to cell or fluorescence assays, any assay with an optical read-out that occurs on a time scale of less than minutes can benefit from the invention.

Figure 24A:
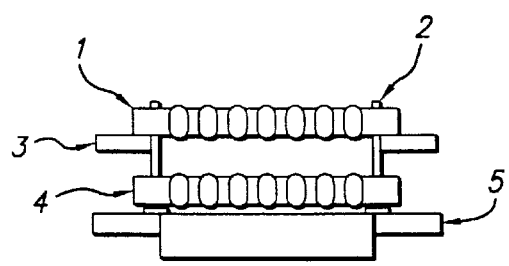
FIG. 24 depicts a device for aligning platens having a plurality of through-holes inside a detection device, wherein the platens are held in place through device comprising two pins attached to a flat base.
Figure 24B:
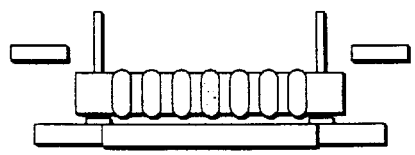

A preferred embodiment of the invention includes at least two stacked and co-aligned platens containing through-hole arrays consists of (i) a detection device; (ii) a means for introducing platens into the detection device (iii) a means to register the platens to cause fluid to communicate between at least some of the co-registered through-holes and (iv) a means of contacting the platens to initiate mixing of reagents simultaneously in at least some of the through-holes. The detection device (FIG. 24) can be an imaging device, such as a CCD camera, with optical filters and a light source for illumination. Light from an optical source (1) illuminates parabolic collimation mirrors (3) after passage through a flexible, bifurcated fiber bundle (2). The light then illuminates the stack of arrays at an oblique angle such that light rays transmitted through the array through-holes does not enter into the camera lens (5). This optical arrangement is desirable as a simple means to decrease optical background for increased optical sensitivity.

Separation Methods

A Method of Separating a Stack of Two or More Arrays Filled with Liquid

It can be desirable to separate arrays once the contents of individual through-holes have been combined by stacking. For example, in order to perform a dilution by two an array filled with a chemical library is stacked onto an array containing solvent buffer. After sufficient time for mixing of the two sets of liquids (approximately 15 seconds for 100 nl), the plates are separated to produce two identical arrays of libraries members at half the initial concentration. This process can be repeated to produce a dilution series.

When two through-hole arrays are stacked such that their contents mix, the two plates are not readily separated without cross-contamination between neighboring throughholes. Pulling one plate against the additive surface tension created by many microscopic columns of fluid invariably introduces shear forces that mixes the contents of individual through-holes together as the chips are separated.

A method is proposed to separate each fluid column into two shorter columns separated by a small vapor phase. Small electrodes at the interface between the two stacked arrays produce a small volume of gas in each through-hole. As the bubble grows it recreates the liquid vapor interfaces between the two arrays. After each column is cleaved in two the arrays are separated mechanically.

Alternatively an inert, humid gas is introduced into the atmosphere above and/or below the stacked arrays and nucleated at the interface between the two stacked arrays.

Alternatively the gas can be pumped into the center of each through a matching array of very fine hollow tubes.

Centrifuging (Performing Gravimetric Separation in) an Array of Through-holes

Many biological or chemical assays require centrifugation and/or filtration of samples. In many it can be desirable to filter or centrifuge samples in a biological or chemical assay that is performed in array of through-holes. The following invention pertains to a device for the centrifugation and or filtration of an array of through-holes.

A metal jig with two flat surfaces larger than the array of through-holes can be built. A single or a stack of arrays of through-holes are placed between the two flat surfaces and evenly compressed together with the application of force on the metal plates. The metal jig will be machined such that the amount of compression can be adjusted as desired, preferably by a simple tightening of several screws holding the jig together.

In some applications the filtrate or pellet will need to be recovered from the centrifuged sample. In other cases the pellet formed after centrifugation will need to be removed. A simple solution for this is to machine a plate that contains an array of wells or dimples of a metered volume that are coregistered to the array of through-holes. The array(s) of through-holes can be stacked atop this bottom plate with coregistered wells. If desired, a filter can be placed between the bottom plate and the array(s) of through-holes. After the centrifugation is complete, the bottom plate can be removed and the filtrate or contaminating precipitate can be removed. Alternatively, if the supernatant is the desired fraction, it can be aspirated directly from the array of through-holes without the need for removal of the bottom plate.

In certain applications a large centrifugal force can need to be applied to the array(s) of through-holes. Even with a bottom plate and/or a filter application of large amounts of centrifugal force a stack of arrays of through-holes can result in a lateral displacement of samples that are forced into the spaces between the individual layers of the arrays of through-holes. Coating of the contacting surfaces of the array of through-holes with a hydrophobic material will inhibit lateral diffusion between layers at relatively low centrifugal forces. When high levels of centrifugal forces are required a material can be stacked within each individual array of through-holes such that when the array of through-holes are compressed together by the metal jig a leak-tight seal will be formed between the two arrays of through-holes. If the material used to form the seal is porous it will not impede the flow of liquid between the layers of through-holes, yet it will form a tight seal against lateral flow.

VI. Miscellaneous Uses

To fully realize the potential of reagent volume savings and increased throughput provided by nanoliter volume fluid handling, means and methods of storing chemical and biological samples at high density in low volumes are necessary. These storage systems must be easily access by microfluidic screening instrumentation.

One embodiment of the invention provides the a method to store chemical or biochemical samples at high density and in low volumes. Additionally, samples stored using the devices and methods of the invention can be assayed with a minimum of liquid handling steps or other manipulations. The method includes placing a small volume of compounds dissolved in a solvent in an array of through-holes and adding a second solvent to the array of through-holes without causing substantial migration of the compounds out of the through-holes. The result is an array of compounds dissolved in a liquid that is primarily comprised of the second solvent.

The invention further provides a method of storing compounds in a manner wherein the samples can be readily introduced into aqueous medium for performance of an assay. The step include dispensing a volume of compound in a solvent that is much less than the volume of the container that it is dispensed in, storing for some time, and adding an aqueous medium to fill the remaining volume of the container in preparation for an assay.

In a preferred embodiment, integration of low-volume compound library storage and screening includes the following steps: (1) Dispensing volumes of compound dissolved in a non-aqueous solvent that are smaller than the total volume of the containers to be used for screening. Usually, the volume dispensed will be less than half and could be $\frac{1}{10}$th of, $\frac{1}{40}$th of, or less than the total capacity of the container. Usually, the containers will be part of an array of containers. The container is preferably a hydrophilic area surrounded by hydrophobic areas, such as a channel of a through-hole array, or a spot on a glass slide with spots of hydrophobic areas in a hydrophilic background. (2) Storing the compounds for some period of time. Storage conditions may consist of a low temperature such as 4° C., −20° C., −80° C., submerged in liquid nitrogen, or a lower temperature. Desiccation is usually desirable. (3) Removing the compounds from storage, and elevating them to above the freezing point of the aqueous media to be loaded into the containers, but above the freezing. (4) Adding aqueous medium to the containers. Preferably, the aqueous medium is chilled to above its freezing point and below the freezing point of the non-aqueous medium. The addition could be done by dispensers, but is more rapidly and inexpensively done by dipping the containers into a bath of the aqueous medium. It is advantageous to have the non-aqueous solvent be in the solid form so as to minimize loss of the compounds into the aqueous medium and to prevent communication of compounds in adjacent or nearby channels. (5) Waiting for a time sufficient to allow mixing of the compound with the aqueous medium. And (6) Performing an assay or measurement upon the samples.

Methods for Dispensing Small Volumes into Large Holes

It is advantageous to screen samples such as drug candidates in very small volumes in order to conserve reagents and increase through-put. A typical through-hole array format will have channels that hold 60 nl of fluid and a typical assay will be done with two stacked chips, holding a total of 120 nl. If the maximum concentration of DMSO acceptable in the assay is 2%, then a total of 2.4 nl must be dispensed into one of the channels and this is extremely difficult to do with conventional liquid handling systems. One way to solve this problem is to dissolve the compounds in a volatile solvent such as ethanol, DMSO, water, dispense the compounds and allow the solvent to evaporate, leaving a spot of dried compound in the container. This has some major disadvantages in that the compound may crystallize into a form that does not easily re-solubalize, and is not sufficiently immobilized. Another approach would be to dispense the compound in a volatile solvent such as DMSO and allow the DMSO to evaporate to leave the desired compound in a lower volume of DMSO. In this case, it may be difficult to evenly evaporate the solvent, which may interfere with the assay to be performed on the samples.

A more robust approach is to dissolve the compound in a first volatile solvent such as DMSO and a second, more volatile solvent, such as ethanol or methanol, dispense the mixture into the containers and allow the second solvent to evaporate, leaving compound dissolved in to first solvent. Ethanol and methanol are good choices since they will dissolve most drug-like compounds and are hydrophilic enough to remain contained in a hydrophilic container surrounded by hydrophobic barriers, although other solvents could be used. DMSO is a good solvent for use as the first solvent since it dissolves most compounds, will stay in place due to its hydrophilicity and is not very volatile, evaporating more slowly than water.

The invention also features a method for storing compounds dry in an array of sub-microliter containers separated by hydrophobic barrier. Compounds are dissolved in a volatile solvent or combination of solvents, introduced into the array of containers and the solvent is allowed to dry, leaving a thin film of solid compound. If necessary, a biocompatible adhesive is added to keep the film attached to the walls of the container. A solvent mixture containing a first volatile solvent and a second less-volatile solvent is added to substantially all of the containers in the array. In a preferred embodiment, the solvent mixture comprises an alcohol such as ethanol and DMSO. The more volatile solvent is allowed to evaporate, leaving a residue of the less-volatile solvent that dissolves at least most of the compounds in the array. Typically, the less-volatile solvent will comprise the minority of the solvent mixture, is usually less than 20%, and is often less than 5% of the solvent mixture. The array is then prepared for assay by introducing an aqueous media that is compatible with the assay such as water or a buffer. The aqueous media may be dispensed by the methods described above.

EXAMPLES

The invention is further described in the following examples, which do not limit the scope of the invention described in the claims.

Example 1

DNA Probe Array

A 50,000-channel through-hole array is fabricated from silicon. Using the gene database, series of 80 spatial filter top masks with another 80 identical bottom masks are fabricated. Arrays are aligned and derivatized with 3-glycidoxypropyltrimethoxysilane in order to provide a free functional group coating on the interior surfaces of the through-holes.

A stack of ten coated platens is aligned. Alignment is verified by observing the optical transmission of the various channels. Mask #1 is aligned with the top of the stack and an identical mask aligned in the same orientation and the bottom of the stack. Mask #1 is constructed such that the positions in the mask that corresponded to a gene in the database with an adenosine in the first position are open and allow flow through the through-holes in those addressable positions. The stack is rinsed with dry acetonitrile. A phosphoramidite monomer at a concentration of 0.1 M acetonitrile and tetrazole is added by a pressurized flow against the mask. The coupling reaction is allowed to proceed for 3 minutes. An oxidizing solution of iodine/lutidine/acetonitrile/water is introduced into the chip stack and incubated for 2 minutes, followed by rinses with acetonitrile and dichloromethane. The chip is dried by vacuum.

The masks are removed and replaced with a top and bottom Mask #2 corresponding to positions to which a T monomer is to be added. A deprotection agent is added, and the T coupling reaction is commenced.

This process is repeated with Mask #3 for G in the first position, and Mask #4 for C in the first position. Mask #5 corresponds to A in the second position, and so on. After the synthesis is complete the chip is stored in 30% ammonia for 12 hours.

To test the array, a fluorescein end-labeled 20-mer corresponding to one of the intended probes in the array is synthesized by standard methods, dissolved in a hybridizing solution of 6×SSC/0.5% SDS, and introduced into all through-holes of the array simultaneously. The array is washed with 0.5×SSC and the chip is imaged fluorescently. Only the position in the array corresponding to the probe complementary to the test oligonucleotide shows a significant increase in fluorescent intensity over the background level determined by averaging the signal from the remaining positions in the array.

Example 2

Catalyst Screening

A recombinant enzyme library is screened in a dense array of through-holes against a fluorogenic substrate. Genetically diverse *E. coli* containing the gene for the protease subtilisin with a poly histidine tag is created by mutagenesis. A dilute solution of the bacteria is added to a nickel-coated array such that there is an average of 1 to 2 bacteria per through-hole. The bacteria are allowed to grow to the log phase and replicate plated (as described above). The bacteria in the array are lysed by heating, allowing the tagged subtilisin to attach to the nickel coated walls of the array. Another array containing the fluorogenic substrate and reaction buffer (Boehringer) in each well is stacked with the first array. The stack is immediately placed in a CCD camera-based fluorescent imaging system, and the rate of increase in fluorescence intensity is measured for each through-hole. The enzyme with the fastest rate is selected and the corresponding bacteria in the replica plate are grown for further studies.

Example 3

High Throughput Screening with Beads

A 100,000 member combinatorial library immobilized via a photocleavable linker on 10 micron diameter beads is purchased from Affymax. A platen is prepared with 100,000 through-holes of a diameter such that only one bead fits in each hole. The beads are washed in PBS, suspended in a solution containing a fluorogenic substrate for the enzyme to be screened, and spread over the platen with a rubber spatula. An ultraviolet lamp is used to decouple the members of the library from the beads. A second platen filled with a solution of the enzyme in a reaction buffer is aligned and stacked on top of the first chip. The stack is immediately imaged by epi-fluorescence to determine the rate of increase in fluorescence intensity as a function of channel position. Those holes that exhibit decreased enzyme rates are selected for further analysis as drug leads.

Example 4

Absorption Assay

A single-cell layer of CaCo-2 cells is grown on two identical anisotropic membranes coated with collagen slightly larger than the array of through-holes. The cell culture conditions, media, and membrane coatings used in the in vitro growth and maintenance of CaCo-2 cells are well known by those skilled in the art. Once a uniform layer of cells is established, each membrane is sandwiched between two identical arrays of through holes dip-loaded with culture maintenance media. The array and membrane assemblies are cultured an additional day to allow for the CaCo-2 cells to equilibrate and form an intact layer within the through-holes. Two additional arrays with through-holes co-registered with the CaCo-2 arrays are loaded with a chemical diversity library of small molecules. A compound known not to pass through CaCo-2 cells (e.g. mannitol) is used as a negative control to assess the integrity of the CaCo-2 cell monolayer, while a compound known to easily diffuse through CaCo-2 cell monolayers is used as a positive control. One of the arrays containing the chemical library is stacked on the apical side of one of the CaCo-2 cell monolayer arrays to assess apical to basal absorption while the second identical chemical library array is placed on the basal side of the other CaCo-2 cell monolayer array to assess basal to apical absorption. The completed arrays are incubated for 1 hour, allowing time for transport or permeation of the library compounds. The oral bio-availability of the chemical library is assessed by quantifying the amount of library compound diffused through the CaCo-2 cell monolayer (e.g. by mass spectrometry).

Example 5

Ligand Fishing by Blotting from a 2-D Gel

Cellular proteins exhibiting an affinity for a ligand are identified using a 2-D gel. A platen having 500,000 through-holes is derivatized in order to covalently link a segment of the human epidermal growth factor receptor to the inside of each through-hole. Each hole is filled with a buffer solution. A cellular extract of a human cell line is then separated on a 2-D gel of a size similar to that of the platen, and then aligned with the platen. The proteins in the 2-D gel are then blotted onto the chip by applying a buffer above the chip and drawing fluid through the chip by placing the chip on a blotter. The proteins are thus transferred through the chip and those that have an affinity for the epidermal growth factor receptor are retained in the chip. A denaturing solution composed of 1M formamide in 100 mM Tris buffer at pH 8 is used to blot the contents of the chip onto a platen for mass spectrometric analysis. The location of those holes that contain a protein with affinity for the receptor and the mass of the proteins contained in those holes are used to determine the identity of the binding proteins. These proteins can be targets for drugs that block the EGF signaling pathway as a treatment for certain cancers.

Example 6

Screening for Antibiotics

A 500,000 member combinatorial peptide library is prepared in a platen that includes 500,000 through-holes such that the peptides are dissolved in a sterile cell culture medium within the holes. The library is prepared such that the identity of the peptide present in each through-hole is known. A dilute culture of Enterococcus faecium bacteria is prepared such that each through-hole will receive on average 10 bacteria in cell culture medium. The bacteria platen is stacked with the peptide library platen to achieve mixing then incubated at 30° C. for 5 hours. The stacked platens are then imaged by light scattering measurement to determine the degree of bacterial growth in each through-hole.

The holes showing a greater than 99% reduction in growth are identified, and larger quantities of the corresponding peptides are synthesized for further analysis.

Example 7

Finding the Peptide Target of a Kinase by Radiolabeling

A protein suspected of being a protein kinase is isolated. The protein is incubated with radiolabeled ATP substrate in the presence of 100,000 different proteins, all occupying unique positions in a platen having through-holes. After incubation for a sufficient time (e.g., about 20 minutes), the platen containing through-holes is washed with water and the presence of radiolabeled proteins is detected by a phosphor-imaging system. The protein target for the kinase is thus identified.

Example 8

Cytochrome P450 inhibition Assays by Fluorescence

The purpose of this experiment is to examine the potential of a library of compounds to inhibit a specific CYP450 enzyme. The protocol is adapted from Crespi et al., *Anal. Biochem.* 248:188–190, 1997. The fluorometric substrate is 3-cyano-7-ethoxycoumarin for CYP1A2, CYP2C9, CYP2C19 and CYP2D6, and resoufin benzyl ether (BzRes) for CYP3A4. These reagents are obtained from Pharmazyme. A compound library is loaded into one platen array device for each of the CYP450 enzymes to be tested at a concentration equivalent to the Km of each enzyme. The appropriate substrate containing reaction mixture is added to a second platen array device and the enzyme is added to a third platen array device. The chips are stacked to initiate the reaction, and the increase in fluorescent signal is monitored continuously by fluorescent imaging. The relative rates of P450 inhibition are used to select a drug lead from the candidate compound library.

Example 9

High Throughput Protein Crystallization

A protein in a solvent is uniformly loaded into a through-hole array. The array through-holes are randomly filled with solutions containing different salts, randomly changing the concentration and relative abundance of the salts. Acidic and basic solutions are subsequently loaded into the through-holes, varying the pH. A temperature gradient is applied to the array device (or the array can alternatively be held at a constant temperature), causing the solvent to evaporate at a given rate. Additionally, the partial pressure of solvent can also be changed in the container in which the array is placed to change the evaporation rate. Those through-holes in which protein crystallization is observed are exposed to a beam of X-rays or electrons and the diffraction pattern recorded for analysis. An important benefit is the rapid and efficient discovery of experimental conditions leading to crystallization. Furthermore, protein crystals can be analyzed directly in the through-hole array.

Sixteen different crystallant solutions, and eleven different buffers, are obtained from Emerald Biostructures (Bainbridge Island, Wash.), and randomly loaded into the platen through-holes together with lysozyme. A temperature gradient is applied across the platen, and the excess liquid is removed with a rubber spatula. The system is sealed in a container with 20 ml of precipitant solution. Optimal solution conditions are determined for crystallization using LC-MS (liquid chromatography-mass spectrometry).

Example 10

Ultra High Throughput Mixture Separation and Screening in Dense Arrays of Through-Holes In many situations such as screening of natural products for pharmacologically active molecules, complex mixtures need to be rapidly and efficiently separated and screened against protein targets. The purpose of this experiment is to separate and screen in a dense array of through-holes a complex mixture of natural products against a fluorogenic substrate. The natural product sample is first prepared in the normal manner for high pressure liquid chromatography (HPLC). As liquid elutes from the chromatographic column, equi-volume samples are acquired and stored sequentially in the array through-holes. A replicate plate can be generated simultaneously. Fluorogenic substrate is then loaded uniformly into a second through-hole array. After completion of chromatographic separation, each sample in the array is exposed to the substrate by stacking the sample plate onto the substrate plate. Optical monitoring the fluorescence signal from the assayed fractions selects samples for further evaluation either from the assayed plate or the replicate plate.

An extension of this method to applications where multiple mixtures are stored in a dense array of through-holes is also described (e.g., separation and identification of the active component in a mixture). In one embodiment, a capillary tube array having the same center-to-center spacing as through-holes in the platen is brought into contact with the sample array. Each tube is located to spatially address one hole in the array. The opposite end of the tubing array is inserted into a stack of arrays where each capillary tube addresses a single column of through-holes on spatially co-registered arrays. The number of stacked arrays equals the number of elution samples to be captured and analyzed. Each tube is pre-filled with a porous gel suitable for chromatographic separation of the mixtures. An array plate filled with buffer is stacked onto the sample plate and a pressure is applied to drive the buffer through each through-hole and into the corresponding capillary tube. As liquid exits from each tube, the through-hole in which the tube resides is filled. As the tube array is slowly withdrawn from the array stack the liquid sample is retained in the through-hole. One advantage of this scheme is that fractions eluted from the array of capillary tubes are simultaneously collected. Once an array is filled, it can be removed from the stack and assayed, (e.g., contacting with a platen array containing a fluorogenic substrate). Active compounds revealed by fluorescence emission are then removed from the plate for analysis. Alternatively, the flow rate of liquid from the tubing array and withdrawal velocity can be chosen such that two plates are filled with essentially the same fraction eluted from the column. The two plates are removed; one is assayed while the other serves as a replicate plate.

Figure 13:
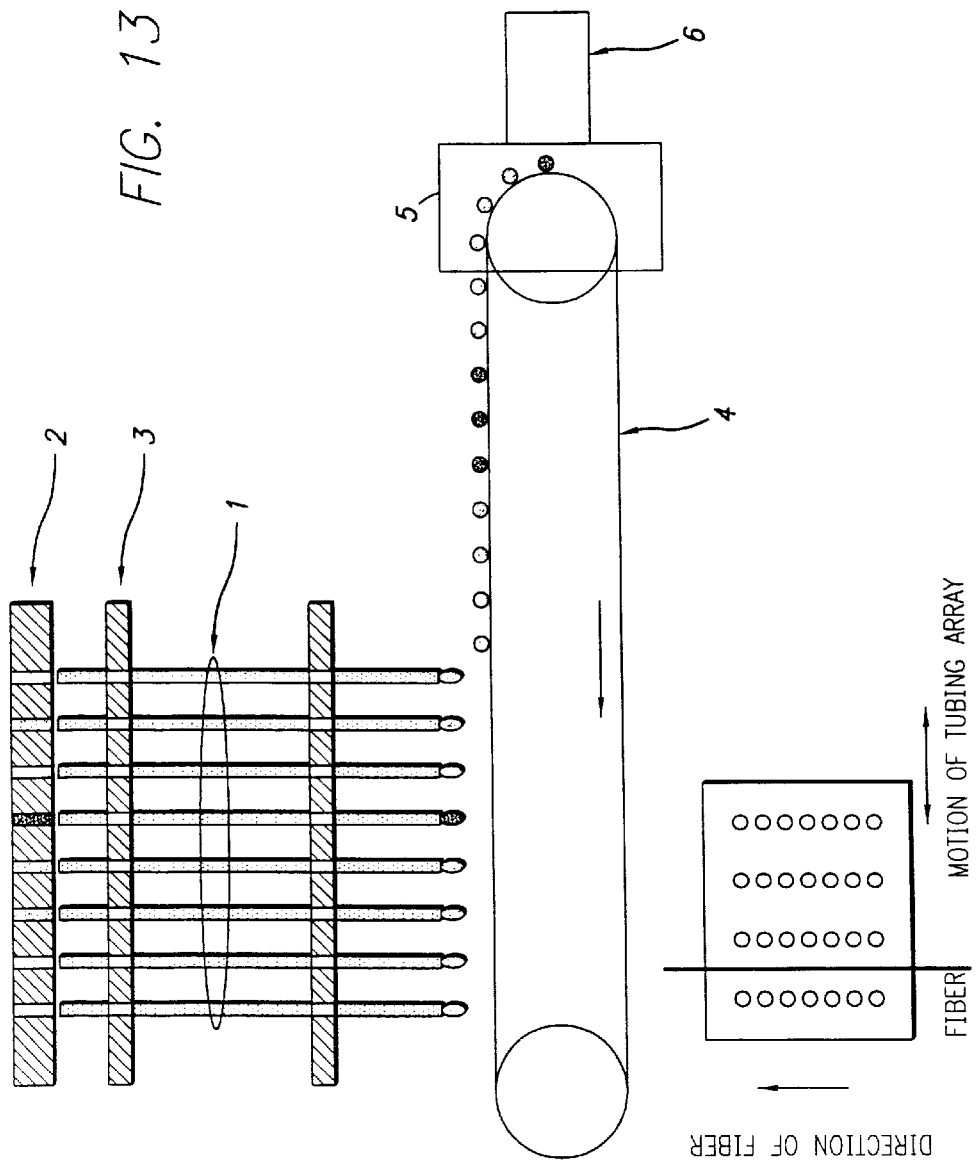
FIG. 13 is an illustration of a method to interface massively parallel HPLC separation with inherently serial analytical methods such as mass spectrometry.

A further extension of this method to interface parallel HPLC separation with inherently serial analytical methods such as mass spectrometry is now described. FIG. 13 depicts, an array of capillary tubing (1) is interfaced with a sample filled through-hole array (2). However the opposite end of the tubing array is splayed in such a manner so as to increase the distance between consecutive rows (or columns) of the array whilst keeping the others intact. A series of spacers (3) through which the tubing is inserted to form the array provides structural integrity. The sample array is brought into contact and co-registered with the capillary tubing array. Each capillary tube in the array is pre-filled with porous gel suitable for chromatographic separation of the mixtures contained in the array through-holes. Pressurized carrier solvent is forced through the holes in the array and carries one sample into one capillary tube. Lengths of the tubing in the array are chosen so as to give the desired separation efficiency for the components in the mixtures analyzed. A fiber or thin tape runs just below and parallel to a row or column of the capillary tubing array. Lateral motion of the tubing array relative to the fiber brings the tubing ends in one column/row in the array into contact with the fiber (or tape) (4). Fluid from each tube is transferred to discrete spatial locations along the fiber. After the fluid is transferred, the fiber is advanced through a vacuum interface (5) and the fluid drops are sequentially presented to the mass spectrometer (6) for analysis. After one set of drops is deposited, the surface (e.g., nitrocellulose fiber) is advanced a distance sufficient for next set of drops to be deposited. Note there are only two displacements required, the surface in one direction and the array in the orthogonal direction.

With a combined time to make a mass spectral measurement and move the fiber of about 300 ms, a row of 100 drops is transported and analyzed in 30 seconds. The entire 10,000-tube array is analyzed in 3000 seconds (50 minutes). As shown in U.S. Pat. No. 6,005,664, stochastic sampling can substantially reduce the number of data points (by up to a factor of 10) needed to reconstruct a signal compared with equi-spaced sampling. Implementation of a stochastic sampling protocol could greatly reduce the analysis time.

Example 11

Optimization of Chemical Synthesis Conditions

Optimization of a chemical synthesis by changing one or more process parameters and recording the amount of material synthesized for a set of reaction conditions. Modified process parameters include types of reagents, reagent concentration, sequence of addition/mixing, temperature, and time.

A series of hydantoin compounds, pharmaceutical drugs useful for treatment of epilepsy, are prepared using the new methods in solid-phase synthesis. Each step in the synthesis process consists of reaction with a solvated reagent under a given set of time and temperature conditions and then a wash to remove the excess (unreacted) reagents. Microspheres made from resins having different functional groups (e.g., hydrogen, phenyl, methyl, benzyl, and s-butyl) and a protected amide group are either purchased or synthesized. An array is manufactured with tapered holes such that as the beads are spread across the surface, only one resin bead fits into each through-hole. Microspheres made from different resins are mixed together and spread across the array in a dilute solution such that all the holes are filled, each with a microsphere made from a different resin. Next, a mask is placed over the regular array of through-holes and the amine groups of the exposed resin beads are deprotected by exposure to a strong acid (e.g. trifluoroacetic acid) or base. After a wash step to remove the acid or base, the same resins are exposed to one member from an isocyanate group library consisting of different chemical and structural moieties. Reaction between the isocyanates and amide groups from a urea with a variable moiety. Such chemical units include hydrogen, butyl, allyl, 2-trifluorotoyl and 4-methoxyphenyl. The reaction proceeds at an elevated temperature for a certain time after which the exposed holes are washed to remove unreacted reagents. This process is repeated with a new mask exposing some of the original holes as well as new ones to expose these microspheres to a new isocyanate library group. Upon completion, the hydantoins are screened against targets to find those potent compounds. Varying the reagents, their concentrations, the reagent sequences, the reaction temperature and reaction time provides a rapid and efficient method to optimize the synthetic rout.

Example 12

Selection of Phage Antibody Libraries (Multi-Chip Method)

A library of phage antibodies against a target antigen in a dense array of through-holes is screened. The protocol was adapted from (Winter, http://aximtl.imt.uni-marburg.de/~rek/AEPStart.html).

Through application of recombinant DNA technology a large ($10^8$ to $10^{10}$) and diverse monoclonal antibody library is produced and stored as DNA plasmids in bacterial (*E. coli*) colonies. A single round of conventional affinity selection is performed in an immunotube coated with the target antigen. After incubating, blocking, and washing, the specifically bound phage are eluted and used to reinfect additional *E. coli*.

Two 10,000-through-hole silicon arrays are fabricated. Both array devices are loaded with a solution of purified target antigen. The array devices are then incubated at 4° C. for approximately 12 hours, washed and filled with a blocking solution consisting of 4% dry milk powder in phosphate buffered saline (PBS). After one hour the blocking solution is removed, the array devices are rinsed and refilled with a buffered solution of IPTG to induce phage expression in the bacteria.

A sufficiently dilute solution of the phage-infected bacteria is added to a third 10,000 through-hole array such that there is an average of 1–10 bacteria per through-hole. The resulting through-hole array, henceforth referred to as the Library Expression Chip, is incubated until the bacteria reach log phase. The Library Expression Chip is stacked between the two antigen coated through-hole arrays. The stack is then incubated for two hours in a high humidity chamber to allow binding of the phage antibodies to the antigen. The antigen through-hole arrays are washed to remove bacteria and unbound phage and separated from the Library Expression Chip.

The bound phage from one of the two antigen through-hole arrays, henceforth referred to as the Phage Inoculation Chip, is eluted by filling the through-holes with a solution of 100 mM triethylamine, incubated for approximately 10 minutes, then neutralized by stacking onto another 10,000 through-hole array containing 2×Tris-HCl buffer. The eluted phage is used to inoculate uninfected bacteria contained in a fourth 10,000 channel array. This array, henceforth referred to as the Positive Expression Chip, is grown to log phase and stored.

Meanwhile, the second antigen-phage chip, the Antibody Selection Chip, is analyzed for bound phage antibody via an indirect ELISA assay. The protocol is adapted from *Current Protocols in Immunology*, Supplement 15, pages 11.2.2–11.2.5. This protocol is an indirect ELISA to detect specific antibodies. Other forms of ELISA assays, such as direct competitive ELISA assays can be implemented in the through-hole arrays with minor modifications to the procedure described in this example.

The Antibody Selection Chip is filled with a solution of the developing reagent, an-M13 conjugated to horseradish peroxidase in blocking solution. After incubating for thirty minutes at room temperature, the array is washed, blocked, and washed again. The array is then filled with a solution of fluorescent substrate, and incubated for 30 minutes at room temperature. A fluorescent image is then collected every 5 minutes for one hour. All positive through-holes are identified by an increase in fluorescent intensity with time. Each corresponding bacterial culture is then extracted from the Positive Expression Chip and dispersed onto agar (containing ampicilin) in a separate cell culture well. These selected bacterial cultures constitute a source of additional phage antibody for subsequent analysis.

In an alternative method, the Library Expression plate, rather than the chip is replica plated. Only a single antigen through-hole array is exposed to the antibody library. After identifying positive interactions in the Antigen Selection chip, the bacteria from the corresponding through-holes of the replicated Library Expression plate are diluted and dispersed across another 10,000 through-hole array. The assay is repeated until to ensure that all selected bacterial colonies are monocultures.

Example 13

Selection of Phage Antibodies (Single Plate Method)

A library of phage display antibodies is screened against a target antigen using a single 10,000 channel array of through-holes. By performing the selection in a single array simplifies the screening process, the phage must be reconstructed from their DNA, ecause the ELISA assay renders selected phage incapable of reinfecting bacteria.

The target antigen is immobilized on the walls of the through-holes by filling an array with antigen solution and incubating in the environmental chamber. Non-specific binding sites are blocked by washing the array with blocking solution.

A solution of the phage-infected bacteria is added to all through-holes in the array such that there is an average of 1–10 bacteria per through-hole. The assay device is then incubated in a humidified chamber until the bacteria reach log phase. The assay device is submerged in a solution of IPTG for a period of time sufficient for diffusion of IPTG into through-holes, but insufficient to permit bacteria to diffuse out of the array. The assay device is incubated to allow expression of phage antibody, and antibody-antigen binding. The expression of phage antibody in the presence of the target antibody is counter to current methods in the art, and can reduce the number of antibodies selected in the screen.

Next, the array is washed to remove bacteria, supernatant, and unbound phage from through-holes. Bound phage antibody is then detected by an indirect ELISA assay. After collecting a fluorescent image, the plate is washed and filled with elution reagent to elute bound phage. Solutions in through-holes that are identified corresponding to all positive through-holes by cherry picking to individual wells of a 96-well or higher density microtiter plate. Phage DNA is then amplified by PCR and sequenced. The DNA sequences are used to identify the structure of selected antibodies and to reproduce more phage antibody for further experimentation.

Example 14

Protein Chip

One hundred thousand protein-binding probes are produced using phage display technology according to the methods described in Sheets et al., *Proc. Natl. Acad. Sci. USA*, 95:6157–6162, 1998, incorporated by reference in its entirety, such that each probe selectively binds a particular human protein with high affinity and specificity. The probes are transferred into a platen, such that different protein-binding probe in each of its through-holes. The platen has a TEFLON (R) surface to prevent wetting and protein absorption.

Tissue samples are homogenized, and the protein portions are extracted and equilibrated with the platen. The platen is washed to remove non-specifically bound molecules. The contents of each through-holes are analyzed by heating the platen from ambient temperature to 100° C. over a two minute period while using Raman imaging to detect protein desorption from the walls of the through-holes into the centers of the through-holes.

Example 15

Construction of an Array of Micro-HPLC Columns for Rapid Parallel Sample Separation and Purification An array of twelve through-holes in a linear arrangement is machined in a block of material (e.g., metal, ceramic, or plastic). The through-holes have a diameter of 250 µm, a total length of 20 mm, and a center-to-center spacing of 9 millimeters. The internal diameter of the distal end of the array of through-holes is increased and threaded to accept standard 1/16" outer diameter HPLC tubing using a standard nut-and-ferule compression fitting. A 2 cm long piece of 50 µm internal diameter, 1/16" outer diameter tubing is mated to each of the through-holes in the array through machined compression fittings. A 1/16" outer diameter stainless steel frit is placed inside the through-hole and is held in place with the compression fitting. Chromatography media is then packed into the each through-hole in the array in the form of a slurry. The chromatography media is immobilized within the through-hole due to the stainless steel frit at the distal end, and creates a micro-HPLC column. When pressurized, sample, wash, and elution buffers will flow through the chromatography media and the frit, and elute from the through-holes through the mated 50 µm internal diameter tubing at the distal end.

Samples are loaded onto the array of micro-HPLC columns by mating a bank of syringes to the micro-HPLC array as detailed in examples 2 and 3. Wash and elution buffers are flowed through the micro-column array using the same syringe bank. A flow rate of 1 to 20 µl of liquid per minute is used to wash and elute the samples from the micro-columns. The use of narrow bore tubing at the distal end of micro-HPLC columns results in the liquid eluting from the column to form small droplets. The column eluate is collected in an array of wells (e.g., a microtiter plate). The eluate is fractionated by collecting individual droplets as they elute from the micro-HPLC columns in different wells of the microtiter plate. Chemical and physical analysis (e.g., spectroscopy or spectrometry) of the samples can be performed on the samples within the wells.

Example 16

Fluidic Seals for Parallel HPLC in Microcapillary Channels

Figure 16:
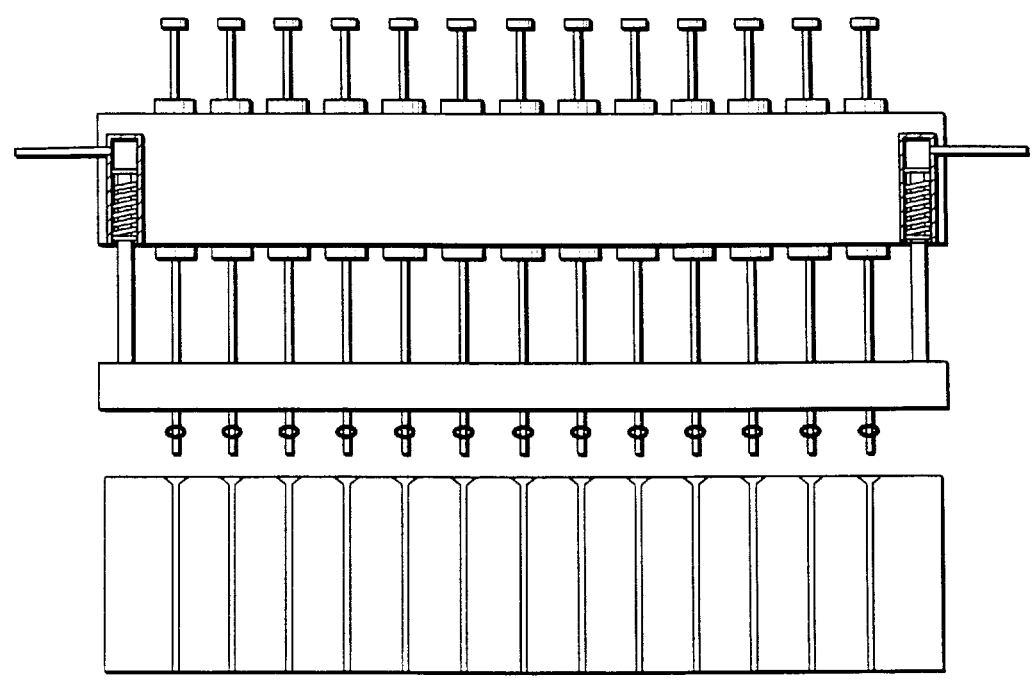
FIG. 16 is an illustration of an array of chamfered through-holes machined in a block of material, a syringe bank with the same center-to-center spacing as the through-hole array, wherein the syringe needles pass through a metal block that is attached to the syringe bank holder by pneumatically-actuated, spring-loaded pins.
Figure 17:
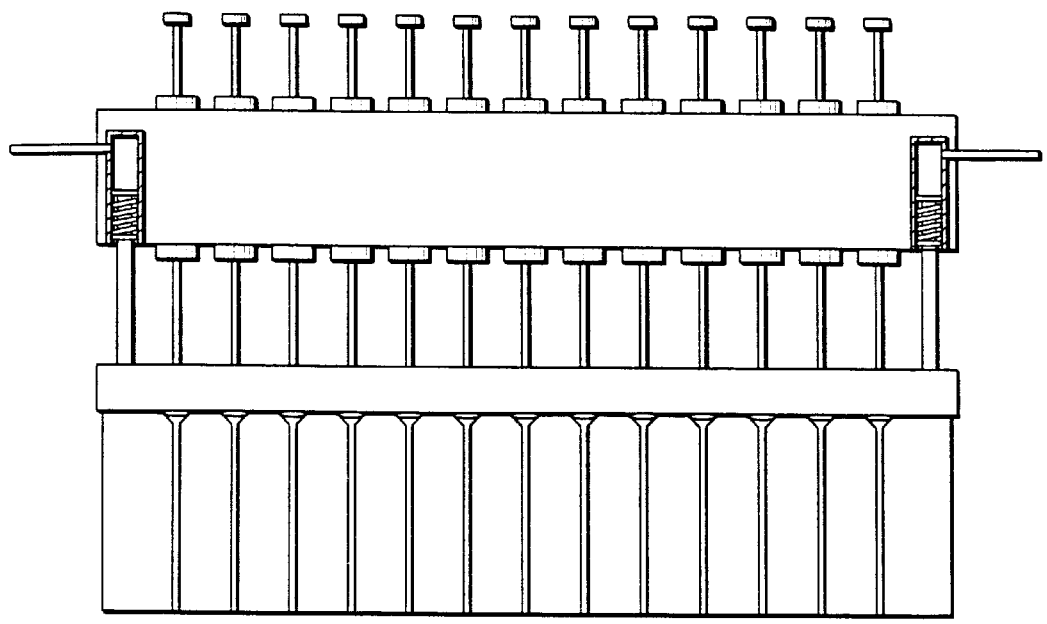
FIG. 17 is an illustration of the array of FIG. 16, wherein the capillary channels are pressurized by the syringes.
Figure 18:
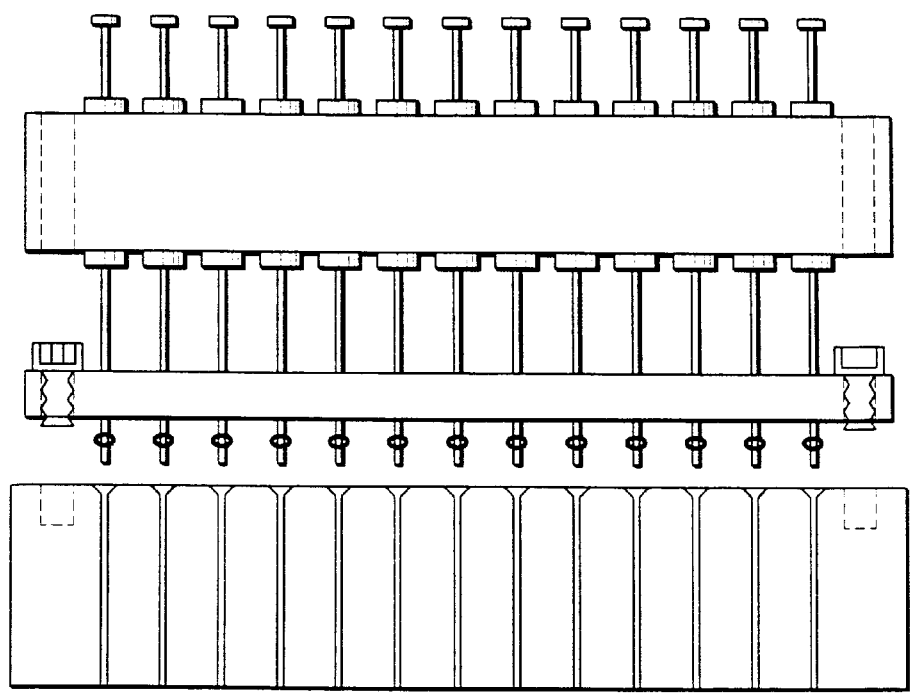
FIG. 18 is an illustration of an array similar to that of FIG. 17, with the exception that the syringe bank is bolted to the capillary tube array.
Figure 19:
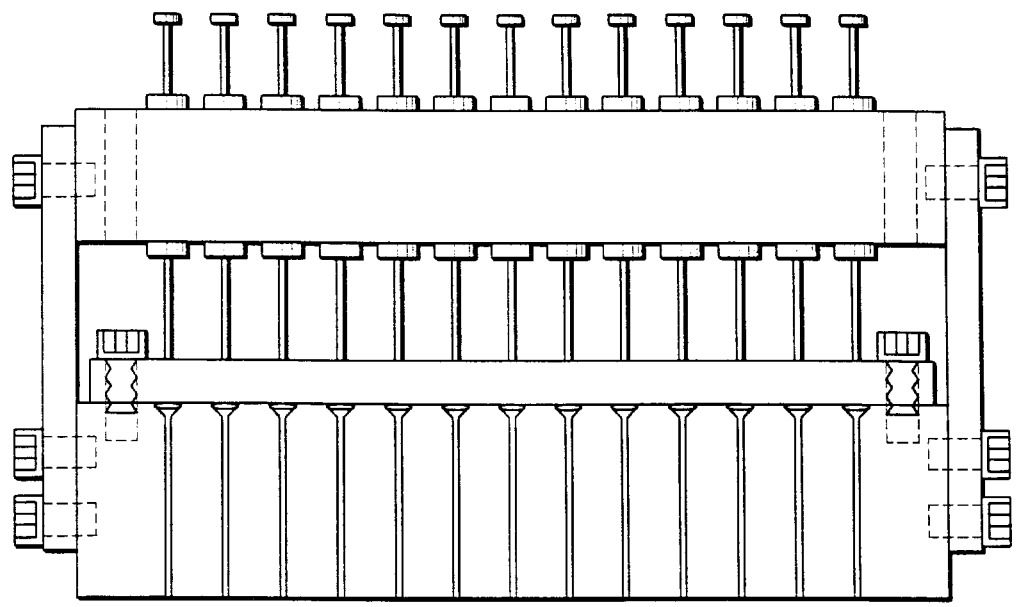
FIG. 19 is an illustration of an array similar to that of FIG. 18, with the exception that the syringe bank is bolted to the capillary tube array.

With reference to FIG. 16, an array of through-holes is machined in a block of material (e.g., metal, ceramic, or plastic). The through-holes have a diameter of less than 1 mm and an aspect ratio greater than 10. The through-holes are chamfered to accept an o-ring gasket. A syringe bank is fabricated with the same center-to-center spacing as the through-hole array. The syringe needles pass through a metal block that is attached to the syringe bank holder by pneumatically actuated, spring-loaded pins. O-ring gaskets are placed onto the syringe needles protruding through the block. The syringes are loaded with fluid and inserted into the capillary tubes. The pins are pneumatically actuated to bring the metal block in contact with the top surface of the capillary tube block and press the o-ring gaskets into the hole chamber and around the syringe needle. This makes a leak tight seal between the needle and capillary channel thus allowing the capillary channels to be pressurized by the syringes (FIG. 17). FIGS. 18 and 19 illustrate a similar approach, except that the syringe bank in those figures is shown bolted to the capillary tube array to result in a rigid structure for easy handling.

Example 17

Identifying a Ligand to a Biomolecular Target

The purpose of this experiment is to use low volume chromatography using through-hole arrays to identify ligands in a chemical, biochemical or biological mixture that bind to a biomolecular target, in this case a protein. Two linear through-hole arrays are constructed such that each through-hole holds 50 nl of liquid when filled. The exterior surfaces of the arrays are treated to be hydrophobic and the interiors are treated to be hydrophilic. A center to center spacing of 9 mm between each of the through-holes is used and registration holes are includes to ensure alignment and co-registration of the through-holes upon stacking of the arrays using pins on a precision jig. A bank of syringes is used to dispense 50 nl of target protein solution into the first array and 50 nl of different compound libraries into each through-hole of a second array. The arrays are stacked using a precision jig and the fluids are allowed to mix in each of the co-registered through-hole positions. A bank of syringes with compression fittings is filled with 1 ml of eluant, followed by a small air bubble and the used to draw up the 100 nl of the protein-library reaction mixture. The reaction mixture is held in the tip of the syringe and kept separate from the eluant reservoir by the air gap. The syringe tips are the placed into the orifice of an array of size exclusion columns and the compression fittings are tightened to ensure a seal. The samples are dispensed into the column, followed by the eluant. By monitoring the UV absorbance of the sample exiting at least one column, one may determine when protein bound to ligand is exiting the column. This protein is then recovered onto an array of reverse phase columns by coupling the two column arrays. The ligands are removed from the protein by reverse phase chromatography, recovered, and analyzed to determine their identity.

Example 18

Protection of Through-holes by Coating with Wax

Paraffin wax with a melting point of 54° C. is heated above its melting point. A through-hole array is submerged in a thin layer of molten poly(ethylene glycol) wax with an average molecular weight of 1500. The through-hole array and wax are cooled to cause the wax to harden. Excess wax is removed from the surface by scraping with a sharp blade and then polishing. The wax-filled array is then exposed for 10 seconds to vapor from a solution of (tridecafluoro-1,1,2,2-tetrahydrooctyl)-1-trichlorosilane diluted 1:20 in xylenes. The coating is then cured by baking the platen at 110° C. for 30 minutes while allowing the wax to melt and drip out of the platen. Wax residues can be removed from the channel interiors by washing with water. The platen is then rinsed for 10 seconds in sulfuric acid/hydrogen peroxide (2:1), and then with water, to remove residues and ensure oxidation of the channel interiors. The resulting through-hole array has a hydrophobic exterior and a hydrophilic interior.

Example 19

Photo-initiation Method of Fiberglass Through-hole Array Production

A sheet of fiberglass filter such as that available from Millipore (Bedford, Mass.) is soaked in a polymerizable solution (e.g., a solution containing methyl methacylate monomer and a photoinitiator such as benzoin methyl ether) and placed between two quartz plates, each having an array of dots that serve to mask the areas that will remain open and porous Polymerization of the monomer solution is effected by illuminating the photomasks with ultraviolet light.

Example 20

Application of an Assay to an Array of Through-holes

A common assay used in drug discovery efforts is the cytochrome P450 inhibition assay. Compounds that inhibit the activity of P450 enzymes are generally undesirable as pharmaceuticals as they have the potential to cause serious side-effects and have the potential for negative reactions if taken in conjunction with other pharmaceuticals. A common assay that is used to screen compounds that are potential candidates for becoming pharmaceuticals is to incubate the compounds in a cellular, extra-cellular, or recombinant system than expresses P450 enzymes and to assay the activity of the enzymes in the presence of the candidate compound. Such an assay could be modified for analysis in a massively parallel manner in an array of through-holes.

Four co-registered arrays of through-holes in which the through-holes are used. The enzyme or cellular compartment (e.g., microsomal compartment of a liver cell) that expresses P450 enzymes can be loaded into one array of through-holes such that each through-hole contains an equivalent volume and concentration of P450s. A known substrate for a chosen P450 enzyme along with a source of NADPH (a source of energy) can be loaded onto a second array of through-holes such that each through-hole contains an equivalent volume and concentration of substrate and NADPH. A third plate can be loaded with known concentrations (e.g., serial dilutions) of the compounds that are to be assayed along with positive and negative controls. An invention for the rapid loading of multiple arrays of through-holes has been described elsewhere in this document. The assay is started when these 3 arrays of through-holes are brought in to contact with one another. As has been described elsewhere in this document, by controlling the size, density, and surface chemistry of the through-holes and the arrays themselves the contents of the 3 arrays can be made to rapidly mix with one another while inter-through-hole contamination between two or more adjacent through-holes can be avoided.

The stacked array of through-holes is then incubated at 37° C. in a controlled humidity environment to allow the reaction to proceed. By maintaining a high humidity environment during this incubation evaporative loss from the through-holes can be minimized. After 30 minutes a stop solution (e.g., organic solvent, urea, high salt solution etc.) is added to the each through-hole by stacking a fourth array filled with the stop solution with the assay arrays. The stop solution works to stop the assay by causing the P450 enzymes to denature and/or precipitate out of solution. This precipitate can be pelleted by centrifugation using an invention described elsewhere in this document. The top array of through-holes can then be removed from the others and used for analysis. In many assays, when the substrate is metabolized by the P450 enzymes it is transformed from a non-fluorescent compound into a fluorescent one. The amount of fluorescence will be directly proportional to the amount of P450 activity. If the compound being assayed inhibits the P450 enzyme, the less the metabolism that will occur and less fluorescent material will be generated. The concentration at which the P450 enzyme is inhibited by 50% ($IC_{50}$) can be determined if multiple concentrations of inhibitors were used in the assay. Fluorometric and/or mass spectrometric analysis of the samples can be performed using inventions described elsewhere in this document.

Example 21

Washing Protein From a Surface of a Through-hole Array

A through-hole array is prepared from silicon with a fluoro-chloro-alkane coating on its surface and is treated with an oxidizing solution that renders the interiors of the holes hydrophilic. The array is dipped in water and frozen to −80° C., then quickly dipped into a solution of the fluoropolymer FluoroPel® (Cytonix Corp., Beltsville, Md.). The array is baked at 200° C. for 20 minutes, and then dipped into cell media containing 10% fetal calf serum. Dipping the through-hole array into the medium fills the holes in the array and wets the surface. By then dipping the through-hole array into perfluorooctane and withdrawing slowly, the surface is cleaned of all aqueous media.

Example 22

DNA Sequencing

Fluorescently labeled DNA fragments are prepared by Sanger sequencing and arrayed in an array of 2500 through-holes in a platen of 0.5 mm thickness. This platen is then stacked on a second platen of 80 mm thickness containing a gel and inserted into an actively cooled electrophoresis tank. As fluorescent oligos emerge from the column array they bind to a nitrocellulose membrane unwound from a spool. A computer controls both the movement of the membrane and turns off the electric field while the nitrocellulose membrane (in the form of a tape) is moving. The membrane is then moved to cause exposure to a light source and CCD camera, analyzing the images and creating elution profiles for each of the through-holes. This achieves reconstruction of the DNA sequence.

Example 23

Method of Manufacturing a Platen Using a Plurality of Grooved Plates

Platens having through-holes are to be manufactured from silicon plates having parallel grooves. See FIG. 20. The resulting array has 5000 through-holes, wherein the through-holes are approximately square with each side 0.25 mm in length and the platens are about 1 mm deep.

Nine inch silicon wafers (0.5 millimeter thickness) are used. The circular wafers are precisely cut to yield rectangular pieces (60 in total) that are 55×160 millimeters (a total of three surfaces per wafer are obtained). Grooves of 250 microns width and 250 micron depth are then etched lengthwise into each piece of silicon. A total of 100 grooves are etched into 50 of the silicon pieces and the distance between each groove is adjusted to about 250 microns. The remaining 10 pieces of silicon are not etched. Chemical etching of silicon is a process known to those skilled in the art, and involves the masking the appropriate areas of silicon and treating with acid. The unmasked areas are then etched away in a controlled manner. A total of 25 millimeters from each side is not etched, providing a solid border to the finished platens.

Once the chemical etching of the surfaces is complete, the mask used in the etching process is removed and the non-grooved surface of each piece of silicon is sputter-coated with a thin layer of gold. The pieces of silicon are then stacked together in a jig having a flat surface with a right-angle bracket. Five pieces of silicon without grooves are first stacked, followed by the 50 grooved surfaces, and another 5 pieces without grooves. The entire jig containing the pieces of silicon is moved to a press and pressure is applied to the stacked pieces of silicon. The assembly is heated and allowed to remain under elevated pressure and temperature for about 16 hours. This treatment results in permanent bonding of the platens into a single large piece of silicon with 55×30×160 mm dimensions having 5000 through-holes (in a 100×50 array) and a 25 mm solid border of silicon around the through-holes. A wire saw is used to cut the individual platens to a thickness of 0.5 millimeter. The platens are cut by slicing in the plane orthogonal to the through-holes. See FIG. 20. The wire used in the saw has a thickness of 150 microns and as a result this amount of material is lost during the sawing process. Including the removal of uneven platens created at either end, a total of 230 platens fitting the required specifications are cut from this large piece of silicon.

Both surfaces of the platens are polished in a lapping machine to ensure a flat surface, resulting in an insignificant amount of silicon being removed. Finally, surface chemistry is applied to the platens to provide the finished product, having the desired physical characteristics.

Example 24

Storing and Screening a Nonoliter Volume Compound Library

Compounds are reformatted from 96 well plates into a through-hole array as follows: Compounds in 96 well plates are dissolved in DMSO to 100 times the concentration that they willed be assayed at—for example, 100 uM for a 1 uM final concentration in the assay. The total volume of DMSO sample solution in each well of the 96 well plate is 10 ul. An additional 90 ul of ethanol is mixed into each well and the samples are immediately drawn into a syringe bank for dispensing. The automated syringe bank the dispensed 60 nl volume into each stack of a through-hole array having the same footprint as a 96 well plate. This process is repeated with new 96-well plates until the through-hole arrays are substantially full. The alcohol is then allowed to evaporate, leaving a residue of approximately 600 pl of DMSO dissolved compound in each channel of each through-hole array. After storage of the compounds for the desired time under desiccation at $-80°$ C., a through-hole array containing the arrayed compounds is removed, brought to $10°$ C. so that the DMSO remains frozen and dipped into a beaker containing aqueous assay solution that has been chilled to $10°$ C. Removal of the through-hole array from the beaker under a humidified environment results in the through-holes of the chip being filled with the aqueous medium. The through-hole array is warmed to ambient temperature to allow mixing of the solvents. A second through-hole array is uniformly filled with a freshly prepared, chilled assay buffer containing an enzyme and a fluorogenic substrate; in this case a Matrix Metalloprotease assay. Stacking of the two chips, warming to ambient temperature and fluorescent imaging at several time points over 30 minutes gives a primary screen for enzyme inhibition.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of maintaining the viability of a cell of an aerobic organism in a platen having a plurality of through-holes, the method comprising:
   a) providing a cell of an aerobic organism in an aqueous medium;
   b) loading the cell of the aerobic organism in the aqueous medium into at least some of the through-holes of the platen, wherein the aqueous medium is held in the through-holes by surface tension, and
   c) submerging the platen into a gas permeable liquid, wherein the gas permeable liquid facilitates oxygen transport to the cell and wherein the gas permeable liquid is immiscible with the aqueous medium, thereby maintaining the viability of the cell.

2. The method of claim 1, further comprising assaying one or more physical properties of the cell of the aerobic organism.

3. The method of claim 1, wherein the gas permeable liquid is a fluorocarbon or a silicone polymer.

4. The method of claim 1, wherein the cell is attached to a wall of a through-hole.

5. The method of claim 1, wherein the aqueous media is held in the through-holes by capillary action.

6. The method of claim 1, wherein the cell is attached to or contained within a porous medium inside the through-hole.

7. The method of claim 1, wherein the aqueous medium is a cell culture medium.

8. The method of claim 1, wherein the cell is an embryo.

9. The method of claim 1, wherein the cell is a CaCo-2 cell.

10. The method of claim 3, wherein the gas permeable liquid is perfluorodecalin or perfluorooctylbromide.

* * * * *

UNITED STATES PATENT AND TRADEMARK OFFICE
CERTIFICATE OF CORRECTION

PATENT NO. : 6,716,629 B2
APPLICATION NO. : 09/975496
DATED : April 6, 2004
INVENTOR(S) : Robert Hess et al.

Page 1 of 1

It is certified that error appears in the above-identified patent and that said Letters Patent is hereby corrected as shown below:

After the paragraph entitled "CROSS-REFERENCE TO RELATED APPLICATIONS": insert

--STATEMENT OF RIGHTS TO INVENTIONS MADE UNDER FEDERALLY SPONSORED RESEARCH

This invention was made with government support under Advanced Technology Program Award Number 70NANB1H3003 awarded by the National Institute of Standards and Technology. The government has certain rights in the invention.--

Signed and Sealed this

Seventeenth Day of November, 2009

David J. Kappos
*Director of the United States Patent and Trademark Office*